(12) United States Patent
Zhang et al.

(10) Patent No.: US 7,550,453 B2
(45) Date of Patent: Jun. 23, 2009

(54) 2-ALKOXY-3,4,5-TRIHYDROXY-ALKYLAMIDES, PREPARATION THEREOF, COMPOSITIONS CONTAINING THEM AND USE THEREOF

(75) Inventors: Jidong Zhang, Paris (FR); Neerja Bhatnagar, Neshanic Station, NJ (US); Jean-Marie Ruxer, Issy les Moulineaux (FR)

(73) Assignee: Aventis Pharma SA, Antony (FR)

( * ) Notice: Subject to any disclaimer, the term of this patent is extended or adjusted under 35 U.S.C. 154(b) by 9 days.

(21) Appl. No.: 11/753,160

(22) Filed: May 24, 2007

(65) Prior Publication Data

US 2007/0244087 A1 Oct. 18, 2007

Related U.S. Application Data

(63) Continuation of application No. PCT/FR2005/002932, filed on Nov. 25, 2005.

(30) Foreign Application Priority Data

Nov. 29, 2004 (FR) .................................. 04 12645

(51) Int. Cl.
*C07D 223/10* (2006.01)
*C07D 223/12* (2006.01)
*C07D 215/16* (2006.01)
*C07D 211/72* (2006.01)
*C07D 207/00* (2006.01)
*C07D 207/12* (2006.01)
*A61K 31/55* (2006.01)
*A61K 31/47* (2006.01)
*A61K 31/40* (2006.01)
*A61P 35/00* (2006.01)

(52) U.S. Cl. ............................ 514/210.02; 514/211.03; 514/211.07; 514/212.04; 514/212.07; 514/218; 514/312; 514/349; 514/423; 514/424; 540/363; 540/488; 540/491; 540/492; 540/522; 540/523; 546/158; 546/297; 548/534; 548/550

(58) Field of Classification Search ............ 514/210.02, 514/211.03, 211.07, 212.04, 212.07, 218, 514/312, 349, 423, 424; 540/363, 488, 491, 540/492, 522, 523; 546/158, 297; 548/534, 548/550
See application file for complete search history.

(56) References Cited

U.S. PATENT DOCUMENTS

| | | | |
|---|---|---|---|
| 4,692,522 A | 9/1987 | Parsons et al. |
| 4,831,135 A | 5/1989 | Crews et al. |
| 5,283,241 A | 2/1994 | Bochis et al. |
| 6,239,127 B1 | 5/2001 | Kinder, Jr. et al. |
| 7,153,846 B2 | 12/2006 | Hoffmann |
| 2002/0128474 A1 | 9/2002 | Xu et al. |
| 2007/0065929 A1 | 3/2007 | Hoffmann et al. |
| 2007/0065932 A1 | 3/2007 | Hoffmann et al. |
| 2007/0249584 A1 | 10/2007 | Zhang |

FOREIGN PATENT DOCUMENTS

| | | |
|---|---|---|
| EP | 0 687 673 A1 | 12/1995 |
| JP | 2004262793 | 9/2004 |
| WO | WO 98/35941 | 8/1998 |
| WO | WO 00/29382 | 5/2000 |
| WO | WO 01/85697 | 11/2001 |
| WO | WO 02/39990 | 5/2002 |
| WO | WO 2005/014574 | 2/2005 |
| WO | WO 2005/044803 | 5/2005 |
| WO | WO 2007/135293 | 11/2007 |
| WO | WO 2007/135294 A2 | 11/2007 |
| WO | WO 2007/135295 | 11/2007 |

OTHER PUBLICATIONS

Adamczeski, et al., Novel Sponge-Derived Amino Acids. 5. Structures, Stereochemistry, and Synthesis of Several New Heterocycles, J. Am. Chem. Soc., 1989, 111, pp. 647-654.
Thale, et al., Bengamides Revisited: New Structures and Antitumor Studies, J. Org. Chem.; 2001; 66; pp. 1733-1741.
Groweiss, et al., Cytotoxic Metabolites from an Australian Collection of the Sponge, J. Nat. Prod.; 1999; 62; pp. 1691-1693.
Kinder, et al., Synthesis and Antitumor Activity of Ester-Modified Analogues of Bengamide B, J. Med. Chem.; 2001; 44, pp. 3691-3699.
U.S. Appl. No. 12/267,689, filed Nov. 10, 2008, Zhang et al.
U.S. Appl. No. 12/267,691, filed Nov. 10, 2008, Zhang et al.
U.S. Appl. No. 12/267,692, filed Nov. 10, 2008, Zhang et al.
Chang et al, Synthesis of optically active alpha-aminobenzolactam via an oxidative-cyclization reaction, Tetrahedron: Asymmetry 14 (2003) pp. 2081-2085.
Morton et al, Novel Solid-Phase Synthesis of 1,5-benzothiazepine-4-one Derivatives, Tetrahedron Letters 41 (2000) pp. 3029-3033.
Parsons et al, Cholecystokinin Antagonists. Synthesis and Biological Evaluation of a 3-Substituted Benzolactams, J. Med. Chem. 1989, 32, pp. 1681-1685.
Quinoa et al, Bengamides, Heterocyclic Anthelminthics from a Jaspidae Marine Sponge, J. Org. Chem. (1986) 51, pp. 4494-4497.
Ramana et al, A Carbohydrate-Based Approach for the Total Synthesis of 1,3-Polyol/alpha-Pyrone Antifungal Natural Products, J. Org. Chem. 2005, 70, pp. 8216-8219.
Slade et al, Angiotensin Converting Enzyme Inhibitors: 1,5-Benzothiazepine Derivatives, J. Med. Chem., 1985, 28, pp. 1517-1521.

*Primary Examiner*—Bruck Kifle
(74) *Attorney, Agent, or Firm*—Paul Darkes; Jim Bolcsak

(57) ABSTRACT

The invention relates particularly to 2-alkoxy-3,4,5-trihydroxy-alkylamides, preparation thereof, compositions containing them and use thereof as a medicament, particularly as anti-cancer agents.

11 Claims, No Drawings

2-ALKOXY-3,4,5-TRIHYDROXY-ALKYLAMIDES, PREPARATION THEREOF, COMPOSITIONS CONTAINING THEM AND USE THEREOF

The present invention relates especially to 2-alkoxy-3,4,5-trihydroxy-alkylamides, to their preparation, to compositions containing them and to their use as medicinal products. More particularly, and according to a first aspect, the invention relates to 2-alkoxy-3,4,5-trihydroxy-alkylamides that are useful as anticancer agents.

2-Methoxy-3,4,5-trihydroxy-alkylamides have been described in U.S. Pat. No. 6,239,127, US 2001/0044433 A1, WO 01/85697, WO 00/29382, U.S. Pat. No. 4,831,135, EP 687 673 and US 2002/128474 A1. These documents essentially disclose analogs and derivatives of bengamide, a natural product isolated from a marine sponge, *Jaspis coriacea*.

These same products have been described in the literature: J. Org. Chem. (1986), 51(23), 4494-7; J. Org. Chem. (2001), 66(5), 1733-41; J. Med. Chem. 2001, 44, 3692-9.

Kinder et al., in J. Med. Chem. 2001, 44, 3692-9, show the activity of various bengamides. In this study, the authors explain that the presence of a lipophilic ester on the caprolactam is essential for their in vitro anticancer activity, and that N-substitution of the lactam with a methyl has no effect on the abovementioned activity.

Against all expectation, it has been found that it is possible to obtain products with significant anticancer activity by modifying the substituents borne by the nitrogen of the caprolactam. Products with significant anticancer activity have also been found by modifying the substituents borne by the carbon atoms of the caprolactam, especially by substituting the carbons with a ring. Furthermore, it has been found that it is possible to obtain products in which the caprolactam has been replaced with another heterocycle, while at the same time maintaining satisfactory activity, the substituents being otherwise identical.

These products correspond to formula (I) below:

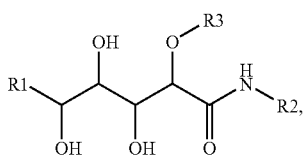

in which:
(i) R1 is independently selected from the group consisting of alkyl, cycloalkyl, heterocycloalkyl, alkylene, heterocycloalkylene, aryl, heteroaryl, arylalkyl, heteroaralkyl, arylalkylene, heteroarylalkylene, —C(R4)=N—O(R5), in which R4 and R5 are independently selected from the group consisting of H, —(C1-C6)alkyl, —(C1-C6)alkylaryl, —(C1-C6)alkylheteroaryl,
(ii) R2 is independently selected from the group consisting of:

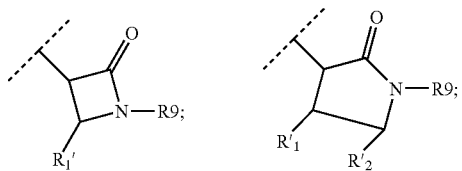

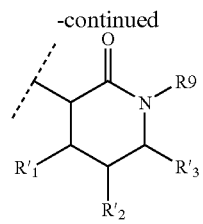

R9 is selected from the group consisting of H, COO(R10), CONH(R10), CO(R10), O(R10) and R10, in which each R10 is independently chosen from a nonbonding electron pair, H, -alkyl, -alkylene, -alkynyl, -haloalkyl, -cycloalkyl, in which each R10 is optionally substituted with at least one substituent chosen from OH, halogen, —(C1-C4)alkyl, —O—(C1-C4)alkyl, —(C1-C4)alkylaryl, aryl, —(C1-C4)alkylheteroaryl, -heteroaryl, —N(CH$_3$)$_2$, —NH$_2$ and —CONH$_2$,

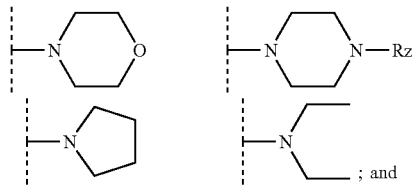

each of the Rz is independently selected from the group consisting of H, COO(R10), CONH(R10), CO(R10) and R10, in which each R10 is independently chosen from —(C1-C4)alkyl, —(C1-C4)haloalkyl, —(C1-C4)alkylaryl and —(C1-C4)alkyl-heteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkylheteroaryl and -heteroaryl;

and R'$_1$, R'$_2$ and R'$_3$ are independently chosen from H and R9 or may together form, along with R9, a 5- to 7-membered aliphatic or aromatic ring containing from 0 to 3 heteroatoms independently chosen from O, S and N.

(iii) R3 is selected from the group consisting of —(C1-C6)alkyl, —(C1-C6)alkylaryl, —(C1-C6)alkylheteroaryl, -aryl, -heteroaryl, -arylalkylene, -heteroarylalkylene.

R2 is preferably chosen from the heterocycles of general formula (II) below:

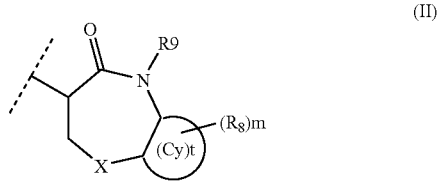

in which:
R9 is selected from the group consisting of H, COO(R10), CONH(R10), CO(R10), O(R10) and R10;
X is chosen from CH$_2$, O, S, SO, SO$_2$, NO and N(Ry) in which Ry is independently selected from the group consisting of R9;

Cy is (i) a bond or (ii) a 5- to 7-membered aliphatic or aromatic ring containing from 0 to 3 heteroatoms independently chosen from O, S and N;

t takes the value 0 or 1;

each R8 is independently selected from the group consisting of H, F, Cl, Br, N(R10)$_2$, NO$_2$, CN, COO(R10), CONH(R10), O(R10) and R10, and m takes the value 0, 1, 2, 3 or 4;

each R10 is independently chosen from a nonbonding electron pair, H, -alkyl, -alkylene, -alkynyl, -haloalkyl, -alkylaryl, -alkylheteroaryl, -alkylarylheteroaryl, -aryl, -heteroaryl and -cycloalkyl, in which each R10 is optionally substituted with at least one substituent chosen from OH, halogen, —(C1-C4)alkyl, —O—(C1-C4)alkyl, —(C1-C4)alkylaryl, aryl, —(C1-C4)alkylheteroaryl, -heteroaryl, —N(CH$_3$)$_2$, —NH$_2$, —CONH$_2$,

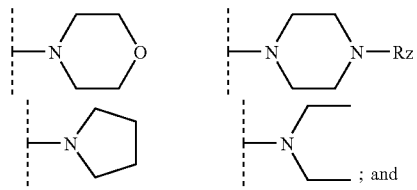

each of the Rz is independently selected from the group consisting of H, COO(R10), CONH(R10), CO(R10), and R10, in which each R10 is independently chosen from —(C1-C4)alkyl, —(C1-C4)haloalkyl, —(C1-C4)alkylaryl and —(C1-C4)alkylheteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkylheteroaryl and -heteroaryl;

with the proviso that:

1) when R3 is methyl and when R1 is CH═C(R4)(R5), with R4═H and R5═C1-C4 alkyl, then R2 is not:

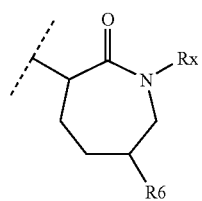

in which Rx is chosen from H, alkyl, cycloalkyl and acyl, and in which R6 is chosen from H, OH, OCO-G, OCO-G-O-G-alkyl, with G chosen from alkyl, alkylene, aryl and heteroaryl;

2) when R2 is:

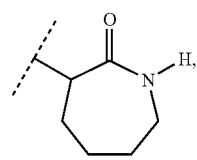

then R1 is not:
(i) 3,3-dimethylbutenyl,
(ii) 3-methylbut-1-enyl;

3) when R3 is methyl, X is —CH$_2$—, t is 0, and R1 is —CH═CH—C(CH$_3$)$_3$, then R9 is not —(CH$_2$)-phenyl, —(CH$_2$)-pyridine or —(C1-C6)alkyl-OH;

4) when R3 is methyl, X is —CH$_2$—, t is 0, and R9 is H, then R1 is not —CH═CH-phenyl, —CH═CH-cyclohexane, —CH═CH-alkyl, -cyclopropane-C(CH$_3$)$_3$, -phenyl-C(CH$_3$)$_3$, —CH$_2$—CH$_2$—C(CH$_3$)$_3$, —C(CH$_3$)═CH—C(CH$_3$)$_3$ or -cyclohexene.

Advantageously, R1 may be chosen from —CH═C(R11)(R12), —CH═N—O(R4), —CH═N(R4); in which R11 and R12 are independently selected from H and (C1-C6)alkyl; and R2 may be a lactam. More particularly, R1 is —CH═C(R11)(R12), in which R11 is H and R12 is (C1-C6)alkyl. Very preferentially, R1 is chosen from (E) —CH═CH—CH(CH$_3$)(C$_2$H$_5$), (E) —CH═CH—CH(CH$_3$)$_2$ and (E) —CH═CH—C(CH$_3$)$_3$.

A preferred substituent R3 is a methyl.

Other products in accordance with the present invention are characterized in that R1 is chosen from —CH═C(R11)(R12), —CH═N—O(R4) and —CH═N(R4); in which R11 and R12 are independently selected from H and (C1-C6) alkyl; and in that R2 is a lactam of general formula (III) below:

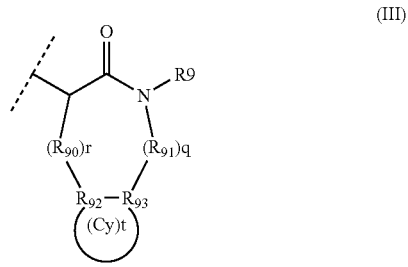

in which:

R9 is selected from the group consisting of H, COO(R10), CONH(R10), CO(R10), R10, in which each R10 is independently chosen from —(C1-C4)alkyl, halogenated —(C1-C4)alkyl, —(C1-C4)alkylaryl, —(C1-C4)alkylheteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkyl-heteroaryl, -heteroaryl,

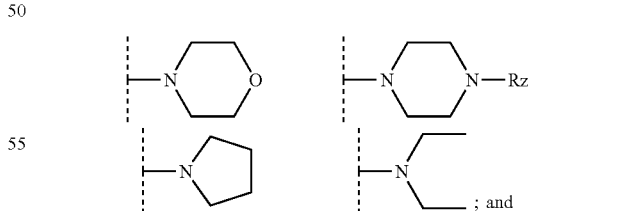

each of the Rz is independently selected from the group consisting of H, COO(R10), CONH(R10), CO(R10) and R10, in which each R10 is independently chosen from —(C1-C4)alkyl, halogenated —(C1-C4)alkyl, —(C1-C4)alkylaryl, —(C1-C4)alkyl-heteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkyl-heteroaryl, -heteroaryl;

$R_{90}$ and $R_{91}$ are each —$CH_2$—;

q and r each independently take a value selected from 0, 1, 2, 3 and 4;

Cy is (i) a bond or (ii) a 5- to 7-membered aliphatic or aromatic ring containing from 0 to 3 heteroatoms independently chosen from O, S and N;

t takes the value 0 or 1;

$R_{92}$ and $R_{93}$ are each chosen from C, CH, N, NH, O and S, it being understood that when one from among $R_{92}$ and $R_{93}$ is NH, O or S, then t=0.

A preferred substituent R2 may be selected from the group consisting of:

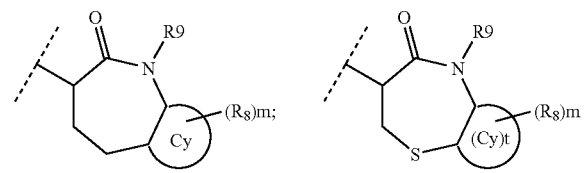

in which R9, Cy, t, R8 and m are as defined in claim 2.

A more preferred substituent R2 is selected from the group consisting of:

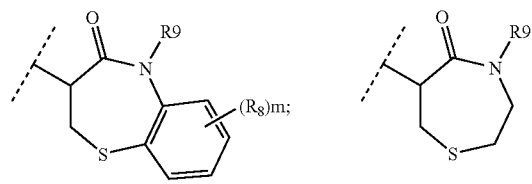

in which:

R9 is selected from the group formed by H, alkene, —(C1-C6)alkylphenyl, —(C1-C6)haloalkylphenyl, —(C1-C6)-alkylphenyl-O-alkyl, —(C1-C6)alkylpyridine, —(C1-C6)-haloalkylpyridine, —(C1-C6)alkylnaphthyl and —(C1-C6)alkyl-N(CH$_3$)$_2$, and R8 and m are as defined in claim 2.

Products in accordance with the present invention are characterized in that R2 is selected from the group consisting of:

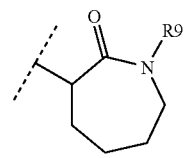

in which R9 is an alkene or a phenyl substituted with 4 or 5 substituents independently chosen from R8 as defined in claim 2.

Another group of more preferred substituents R2 may be selected from the group consisting of:

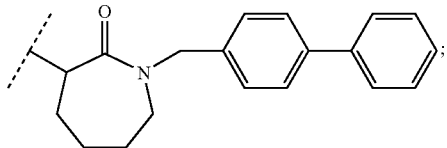

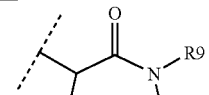

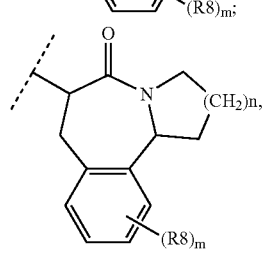

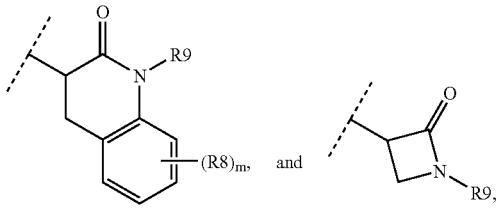

in which:

(i) m takes the values 0, 1, 2, 3 or 4;

(ii) n takes the values 0, 1, 2 or 3;

(iii) each of the R8 is independently selected from the group consisting of H, F, Cl, Br, N(R10)$_2$, NO$_2$, COO(R10), CONH(R10), O(R10) and R10, in which each R10 is independently chosen from H, —(C1-C4)alkyl, halogenated —(C1-C4)alkyl, —(C1-C4)alkylaryl, —(C1-C4)alkylheteroaryl, in which each R10 is optionally substituted with a substituent chosen from halogen, —(C1-C4)alkyl, —O—(C1-C4)alkyl, —(C1-C4)alkylaryl, aryl, —(C1-C4)alkyl-heteroaryl, -heteroaryl,

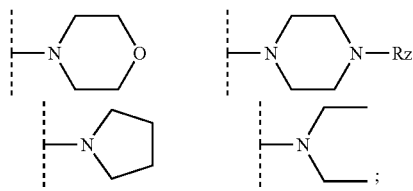

(iv) each of the R9 and Ry is independently selected from the group consisting of H, COO(R10), CONH(R10), CO(R10) and R10, in which each R10 is independently chosen from —(C1-C4)alkyl, halogenated —(C1-C4)alkyl, —(C1-C4)alkylaryl and —(C1-C4)alkyl-heteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkyl-heteroaryl and -heteroaryl,

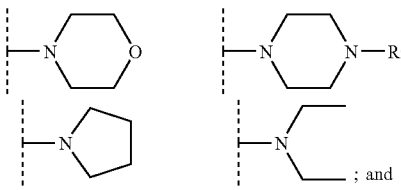

; and (v) each of the Rz is independently selected from the group consisting of H, COO(R10), CONH(R10), CO(R10) and R10, in which each R10 is independently chosen from —(C1-C4)alkyl, halogenated —(C1-C4)alkyl, —(C1-C4)alkylaryl and —(C1-C4)alkyl-heteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkyl-heteroaryl and -heteroaryl.

These substituents R2 that are more preferred may be advantageously substituted with amines, and these amines may be advantageously salified.

Preferably, the invention relates to the products illustrated in tables 1 and 2. Products advantageously prepared according to the present invention are:

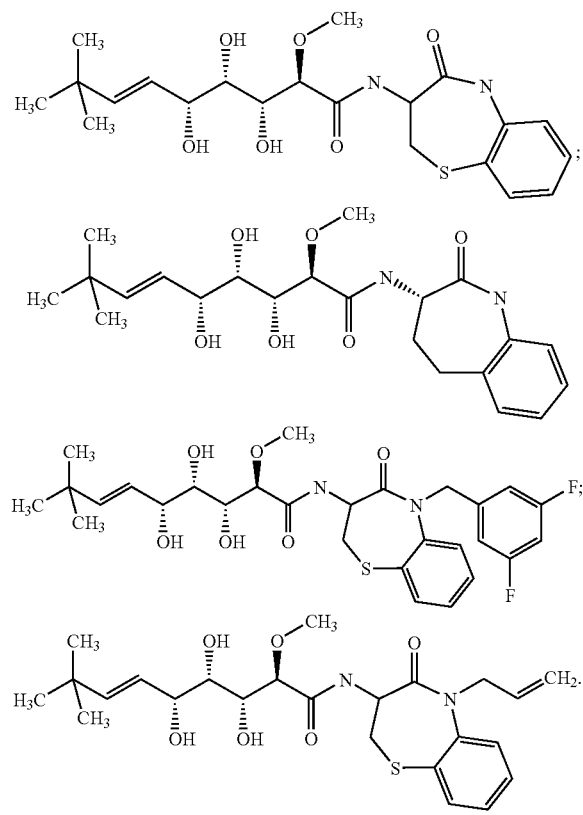

The products according to the present invention may exist in the form of bases, acid-addition salts, solvates, hydrates or prodrugs.

The products in accordance with the invention will preferentially have a polyhydroxylated chain whose absolute conformation is:

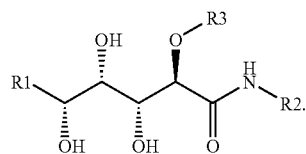

The products according to the invention may be in non-chiral, or racemic, form, or in a form enriched in one stereoisomer, or in a form enriched in one enantiomer; and may optionally be salified.

A product in accordance with the invention may be used for the manufacture of a medicinal product that is useful for treating a pathological condition, in particular a cancer.

The present invention also relates to therapeutic compositions containing a compound according to the invention, in combination with an excipient that is pharmaceutically acceptable according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected against the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and solvents or of complexing agents and solvents.

The liquid forms will preferably be injectable, and, as a result, will have a formulation that is acceptable for such a use.

Acceptable routes of administration by injection include the intravenous, intraperitoneal, intramuscular and subcutaneous routes, the intravenous route being preferred.

The administered dose of the compounds of the invention will be adapted by the practitioner depending on the route of administration to the patient and said patient's condition.

The compounds of the present invention may be administered alone or as a mixture with other anticancer agents. Among the possible combinations that may be mentioned are:
 alkylating agents and especially cyclophosphamide, melphalan, ifosfamide, chlorambucil, busulfan, thiotepa, prednimustine, carmustin, lomustin, semustin, streptozotocin, decarbazin, temozolomide, procarbazin and hexamethylmelamine
 platinum derivatives especially such as cisplatin, carboplatin or oxaliplatin
 antibiotics especially such as bleomycin, mitomycin and dactinomycin
 antimicrotubule agents especially such as vinblastine, vincristine, vindesine, vinorelbine and taxoids (paclitaxel and docetaxel)
 anthracyclines especially such as doxorubicin, daunorubicin, idarubicin, epirubicin, mitoxantrone and losoxantrone
 topoisomerases of groups I and II, such as etoposide, teniposide, amsacrine, irinotecan, topotecan and tomudex fluoropyrimidines such as 5-fluorouracil, UFT and floxuridine cytidine analogs such as 5-azacytidine, cytarabine, gemcitabine, 6-mercaptomurine and 6-thioguanine adenosine analogs such as pentostatin, cytarabine or fludarabine phosphate methotrexate and folinic acid enzymes and various compounds such as L-asparaginase, hydroxyurea, trans-retinoic acid, suramine, dexrazoxane, amifostine and herceptin, and also estrogenic and androgenic hormones antivascular agents such as combretastatin or colchicine derivatives, and prodrugs thereof.

It is also possible to combine the compounds of the present invention with a radiation treatment. These treatments may be administered simultaneously, separately or sequentially. The treatment will be adapted by the practitioner according to the patient to be treated.

Definitions

The term "halogen" refers to an element chosen from F, Cl, Br and I.

The term "alkyl" refers to a saturated, linear or branched hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkylene" refers to a linear or branched hydrocarbon-based substituent containing one or more unsaturations, and containing from 2 to 12 carbon atoms. The ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkylene substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "heteroatom" refers herein to an at least divalent atom, other than carbon. N; O; S; and Se are examples of heteroatoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of cycloalkyl substituents.

The term "heterocyclyl" refers to a saturated or partially unsaturated cyclic hydrocarbon-based substituent containing from 1 to 13 carbon atoms and from 1 to 4 heteroatoms. Preferably, the saturated or partially unsaturated cyclic hydrocarbon-based substituent will be monocyclic and will contain 4 or 5 carbon atoms and 1 to 3 heteroatoms.

The advantages of the invention will be illustrated more particularly by the following examples:

Abbreviations:

Ac acetate; Bn benzyl; ° C. degrees Celsius; cat. catalyst; TLC thin-layer chromatography; PCC preparative column chromatography; cm centimeter; δ chemical shift; d doublet; dd doublet of doublets; DMF dimethylformamide; DMSO-d$^6$ deuterated dimethyl sulfoxide; dt doublet of triplets; eq. equivalent; ES+/− electrospray (positive/negative modes); Et ethyl; g gram; h hour; Hz hertz; IC$_{50}$ inhibition constant at 50% of activity; iPr isopropyl; d. day; J coupling constant; LCMS liquid chromatography coupled to mass spectrometry; m multiplet; Me methyl; mg milligram; MHz megahertz; ml milliliter; μl microliter; mm millimeter; μm micrometer; mmol millimole; min minute; N mol.L$^{-1}$; m.p. melting point; Ph phenyl; ppm parts per million; q quartet; Yld yield; Rf frontal ratio; $^1$H NMR proton nuclear magnetic resonance; s singlet; bs broad singlet; t triplet; r.t. room temperature; tBu tert-butyl; TFA trifluoroacetic acid; THF tetrahydrofuran; t$_R$ retention time; UV ultraviolet; V volt.

EXAMPLE 1

N-(2-Methyl-3-oxo-2,3,4,5-tetrahydro-1H-2-benzazepin-4-yl)-(E)-(2R,3R,4S,5R)-3,4,5-trihydroxy-2-methoxy-8,8-dimethylnon-6-enamide

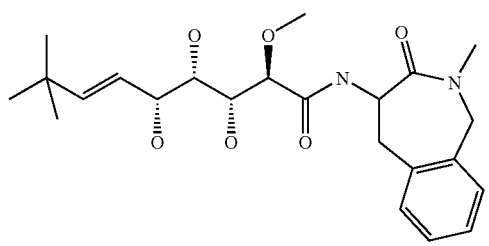

a) Step 1: preparation of methyl (2-methyl-3-oxo-2, 3,4,5-tetrahydro-1H-2-benzazepin-4-yl)carbamate (2)

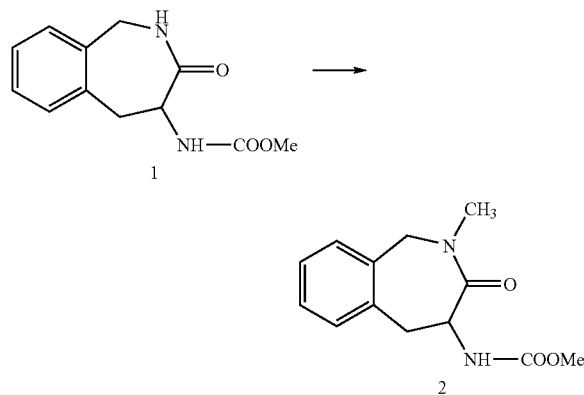

A solution of 176 mg (0.75 mmol) of product 1 (methyl (3-oxo-2,3,4,5-tetrahydro-1-H-2-benzazepin-4-yl)carbamate, which can be prepared according to WO 02/057257 and the content of the description of which is incorporated herein by reference), dissolved in a mixture of 2 ml of dry THF and 2 ml of dry DMF is added dropwise at room temperature to a suspension of 36 mg (0.9 mmol) of 60% NaH dispersed in oil, suspended in 2 ml of anhydrous THF, under an inert atmosphere. At the end of the addition, 159 mg (1.5 eq.) of methyl iodide are added. The reaction mixture is then stirred at room temperature for 2 hours, and 10 ml of saturated ammonium chloride solution are then added, while cooling the reaction medium in an ice bath. The mixture is extracted with 3×10 ml of ethyl acetate. The organic phases are combined, washed with 2×10 ml of saturated NaCl solution, dried over magnesium sulfate and evaporated to dryness under reduced pressure. The oily residue obtained is chromatographed on silica gel, eluting with a 90/10 dichloromethane/methanol mixture. 82 mg (44%) of the expected product 2 are obtained in the form of an oil.

(TLC: Rf=0.7, 90/10 dichloromethane/methanol). $^1$H NMR (CDCl3): δ (ppm) 2.85-3.05 (m, 1H), 3.10 (s, 3H), 3.45-3.60 (m, 1H), 3.65 (s, 3H), 3.83 (d, 1H), 5.15-5.25 (m, 2H), 6.13 (dl, 1H), 7.05-7.25 (m, 4H)

b) Step 2: Preparation of 4-amino-2-methyl-1,2,4,5-tetrahydro-2-benzazepin-3-one (3)

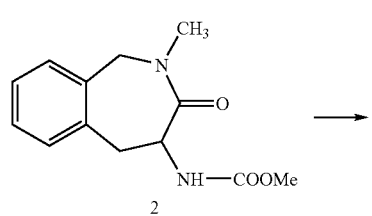

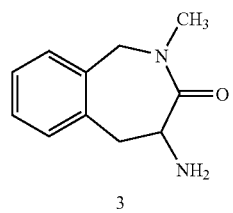

0.6 ml of trimethylsilyl iodide is added to a solution of 203 mg (0.93 mmol) of product 2 in 10 ml of dichloromethane, and the mixture is then refluxed for 3 hours. After cooling to room temperature and adding 50 ml of ethyl acetate, the organic phase is extracted with 2×25 ml of 1N hydrochloric acid solution. The aqueous phases are combined, cooled and then basified by addition of 5N sodium hydroxide. The basic aqueous phases are then saturated with NaCl, and then extracted with 3×25 ml of ethyl acetate. The organic phases are combined, dried over magnesium sulfate and evaporated under reduced pressure to give an oily residue. This residue is chromatographed on silica gel, eluting with a 90/10 dichloromethane/methanol mixture. 100 mg (57%) of the expected product 3 are obtained in the form of an oil.

TLC: Rf: 0.2 (90/10 dichloromethane/methanol). $^1$H NMR (CDCl3): δ (ppm) 2.35 (sl, 2H), 2.95-3.15 (m, 1H), 3.10 (s, 3H), 3.35-3.45 (dd, 1H), 3.77-3.87 (d, 1H), 4.45-4.55 (broad d, 1H), 5.15-5.25 (d, 1H), 7.05-7.27 (m, 4H).

c) Step 3: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-(2-methyl-3-oxo-2,3,4,5-tetrahydro-1H-2-benzazepin-4-yl)acetamide (5)

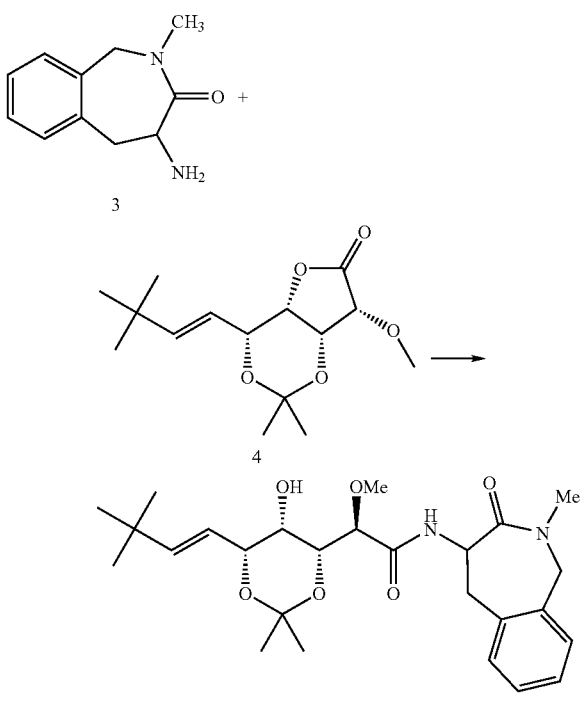

A mixture of 25 mg (0.13 mmol) of product 3, 22 mg (0.13 mmol) of sodium 2-ethylhexanoate and 25 mg (0.088 mmol) of lactone 4 (which may be prepared according to the procedures described in J. Med. Chem, 2001, 44, 3692-3699, starting with the γ-lactone of α-glucoheptonic acid, and the content of which is incorporated herein by reference) in 2 ml of THF are stirred at room temperature under nitrogen. The reaction is continued until the amine 3 has disappeared (about 92 hours), the presence of which is monitored by TLC (90/10 v/v dichloromethane/methanol). After addition of 20 ml of ethyl acetate, the organic phase is washed with 20 ml of saturated aqueous NaCl solution, dried over magnesium sulfate and filtered, and the solvents are then evaporated off under reduced pressure. The residue is purified by chromatography on silica gel, eluting with a 97.5/2.5 v/v dichloromethane/methanol mixture to give a resin. This resin is dissolved in 20 ml of $CH_2Cl_2$, washed with 15 ml of 1N NaOH, 15 ml of saturated NaCl solution, dried over $MgSO_4$, filtered and evaporated under reduced pressure to give 24 mg (59%) of the expected product 5 in the form of a resin (2 diastereoisomers).

ES+/−: 475(+)=(M+H)(+); 949(+)=(2M+H)(+) $^1$H NMR (CDCl3): δ (ppm) 1.02 (m, 9H); 1.46 (m, 6H); 2.80-3.10 (m, 4H); 3.45-4.55 (m, 9H); 5.20-5.90 (m, 4H); 7.05-8.10 (m, 5H).

d) Step 4: Preparation of N-(2-methyl-3-oxo-2,3,4,5-tetrahydro-1H-2-benzazepin-4-yl)-(E)-(2R,3R,4S,5R)-3,4,5-trihydroxy-2-methoxy-8,8-dimethylnon-6-enamide (Example 1)

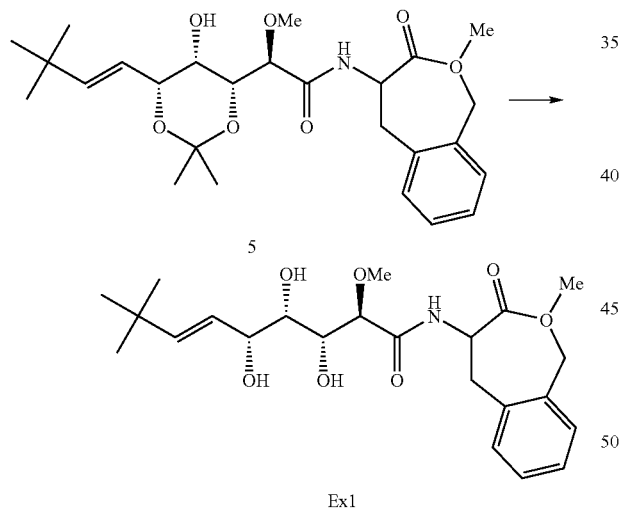

Ex1

24 mg (50 μmol) of product 5, and then 2 ml of a cold trifluoroacetic acid/tetrahydrofuran/water mixture (1.6/1.6/1.0 v/v/v) are successively introduced, at 0° C., into a round-bottomed flask equipped with a magnetic stirrer. This mixture is maintained at 0° C. until the starting material has disappeared on TLC (1 hour) (90/10 v/v dichloromethane/methanol). The solvent is evaporated off under reduced pressure and 2 ml of methanol are added to the residue, which is reevaporated under reduced pressure. This last step is repeated a second time and the residue is dissolved in 5 ml of water in a minimum volume of methanol (0.5 ml). The solution is freeze-dried, giving the expected product Example 1 quantitatively in the form of a foam.

ES+/−; 435(+)=(M+H)(+); 869(+)=(2M+H)(+); 417(+)=(M+H)(+)−H2O $^1$H NMR (CDCl3): δ (ppm) 1.05 (s, 9H); 2.95-3.10 (m, 4H); 3.45-3.90 (m, 8H); 4.27 (m, 1H); 5.25 (broad d, J=16.0 Hz, 1H); 5.35-5.50 (m, 2H); 5.85 (d, J=16.0 Hz, 1H); 7.05-7.30 (m, 4H); 8.08 (broad d, J=6.0 Hz, 1H).

EXAMPLE 2

N—[(S)-1-(biphenyl-4-ylmethyl)-2-oxoperhydroazepin-3-yl]-(E)-(2R,3R,4S,5R)-3,4,5-trihydroxy-2-methoxy-8,8-dimethylnon-6-enamide

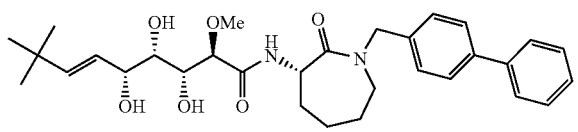

a) Step 1: Preparation of (S)-3-amino-1-(biphenyl-4-ylmethyl)perhydroazepin-2-one hydrochloride (7)

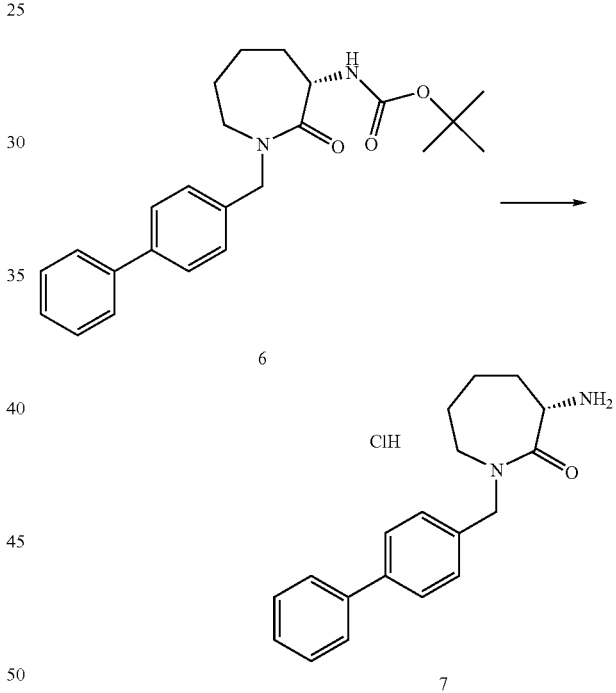

6.5 ml of a solution of HCl in EtOAc (5.5 N) at 0° C., and 2.00 g of 6 (which may be prepared according to the procedures described in WO 2001/068655, and the content of which is incorporated herein by reference) are successively added to a 25 ml round-bottomed flask with stirring, under an inert atmosphere and immersed in an ice bath. The solution is allowed to warm to r.t. with stirring over 3 hours. Evaporation of the solvent gives 1.93 g of white foam, which is triturated in 10 ml of $Et_2O$. The solid that precipitates out is filtered off. However, it is very hygroscopic and must therefore be recovered with MeOH and then evaporated to dryness. 1.666 g of product 7 are collected (Yld=99%).

TLC ($CH_2Cl_2$ 90/MeOH 10): Rf=0.16 $^1$H NMR (300 MHz, DMSO-d$^6$): δ (ppm)=8.2 (s, 2H, $NH_2$); 7.65 (m, 4H); 7.46 (m, 2H); 7.36 (m, 3H); 4.78 (d, 1H); 4.50 (d, 1H); 4.36 (d, 1H); 3.63 (d, 1H); 3.32 (d, 1H); 1.96 to 1.14 (m, 6H) LCMS (ES+, 50 V): $t_R$=2.64 mn|m/z=589$^+$ (2M+H$^+$); 295$^+$ (M+H$^+$); 167$^+$ (PhBn$^+$)

b) Step 2: Preparation of (R)—N—[(S)-1-(biphenyl-4-yl-methyl)-2-oxoperhydroazepin-3-yl]-2-[(4R,5S,6R)-6-((E)-3,3-dimethylbut-1-enyl)-5-hydroxy-2,2-dimethyl-1,3-dioxan-4-yl]-2-methoxyacetamide (8)

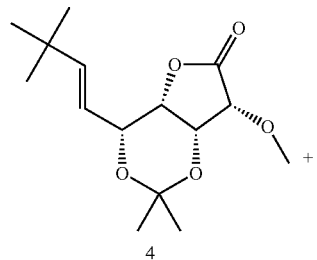

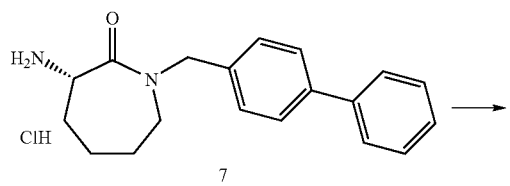

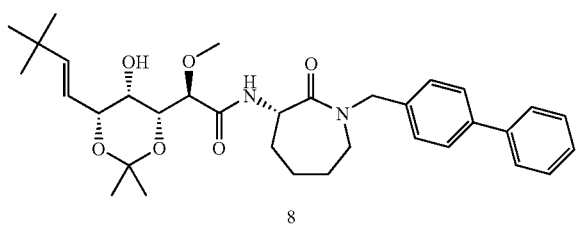

34.81 mg of 4 (0.122 mmol), 50.67 mg of 7 (0.153 mmol), 41.31 mg of sodium 2-ethylhexanoate (0.249 mmol) and 2 ml of THF are successively introduced into a 20 ml round-bottomed flask with stirring and under an argon atmosphere. Stirring is continued for 22 hours at r.t. The next day, 20.09 mg of 7 (0.061 mmol) and 10.54 mg of sodium 2-ethylhexanoate (0.063 mmol) are introduced into the reaction medium. After 3 days, 20 ml of EtOAc are added to the reaction medium, which is then washed successively with 20 ml of NaOH solution (0.1 N), 20 ml of water and 20 ml of saturated NaCl solution. The organic phase is dried, filtered and then evaporated to dryness. The crude product is purified by PCC with a 70/30 EtOAc/heptane mixture (Rf=0.23). 64.43 mg of product 8 are collected (Yld=91%).

LCMS (ES+/, 50 V): $t_R$=4.59 mn|m/z=1157$^+$ (2M+H$^+$); 579$^+$ (M+H$^+$); 521$^+$ (M+H$^+$[(H$_3$C)$_2$CO]); 1201 (2 MH+HCOOH); 623 (MH+HCOOH). $^1$H NMR (400 MHz, CDCl$_3$): δ (ppm)=7.74 (d, 1H); 7.58 (t, 4H); 7.45 (t, 2H); 7.36 (m, 1H); 7.33 (m, 2H); 5.80 (d, 1H, J=15.5 Hz); 5.55 (dd, 1H); 4.29 (m, 1H); 3.88 (m, 1H); 3.80 (m, 1H); 3.72 (d, 1H); 3.51 (s, 3H); 3.28 (m, 2H); 2.11 (m, 2H); 1.63 (m, 1H); 1.47 (m, 2H); 1.50 (s, 3H); 1.48 (s, 3H); 1.43 (m, 2H); 1.04 (s, 9H)

c) Step 3: Preparation of N—[(S)-1-(biphenyl-4-ylmethyl)-2-oxoperhydroazepin-3-yl]-(E)-(2R,3R,4S,5R)-3,4,5-trihydroxy-2-methoxy-8,8-dimethyl-non-6-enamide (Example 2)

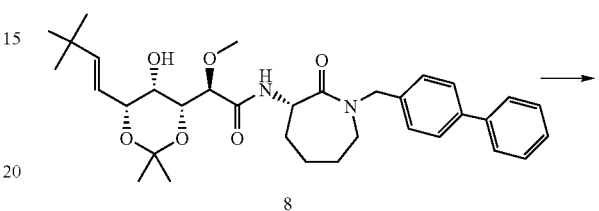

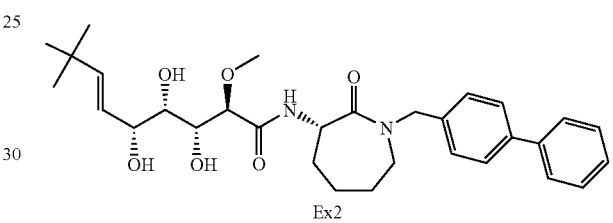

A mixture of 0.6 ml of TFA, 0.6 ml of THF and 0.4 ml of water at 0° C. is introduced into a 30 ml round-bottomed flask containing 59.79 mg of 8 (0.103 mmol), which is also cooled to 0° C. The flask is then stirred at 0° C. under an argon atmosphere for 2 hours 30 minutes. The reaction medium is filtered through a Millipore filter, the solvents are then evaporated off under vacuum at 0° C., and the product is then freeze-dried in 10 ml of pure water and 0.5 ml of MeOH. 50.75 mg of product Example 2 are collected (Yld=91%).

TLC (90/10 CH$_2$Cl$_2$/MeOH): Rf=0.16 LCMS (ES+/, 30 V): $t_R$=4.13 mn|m/z=1077$^+$ (2M+H$^+$); 539$^+$ (M+H$^+$); 521$^+$ (M+H$^+$H$_2$O); 1121 (2 MH+HCOOH); 583 (MH+HCOOH).

EXAMPLE 3

N-(2-Oxo-1-phenylazetidin-3-yl)-(E)-(2R,3R,4S,5R)-3,4,5-trihydroxy-2-methoxy-8,8-dimethylnon-6-enamide

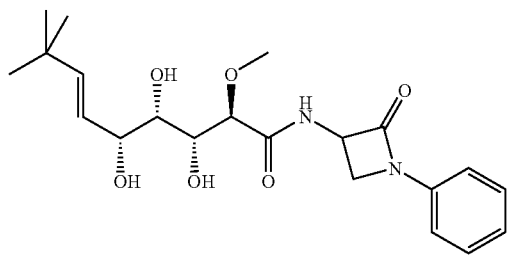

a) Step 1: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-(2-oxo-1-phenylazetidin-3-yl)acetamide (10)

b) Step 2: N-(2-Oxo-1-phenylazetidin-3-yl)-(E)-(2R,3R,4S,5R)-3,4,5-trihydroxy-2-methoxy-8,8-dimethylnon-6-enamide (Example 3)

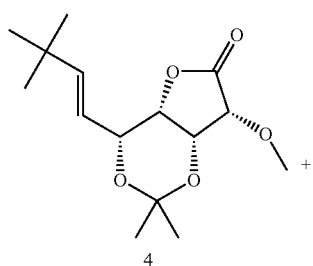

4

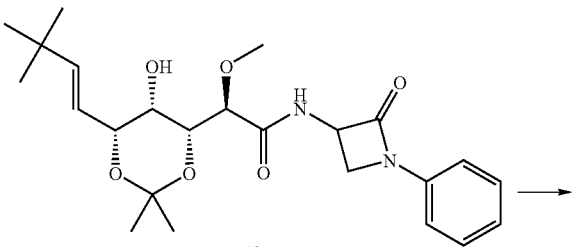

10

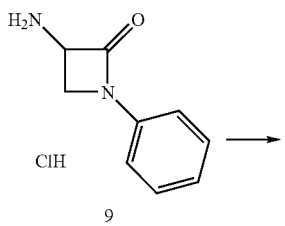

9

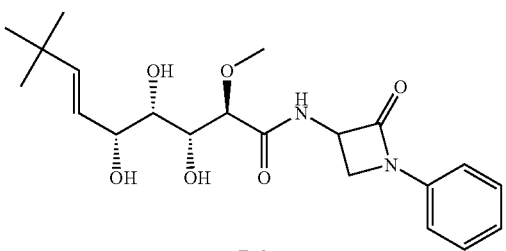

Ex3

10

25.39 mg of 4 (0.089 mmol), 44.36 mg of sodium 2-ethylhexanoate (0.267 mmol), 27.37 mg of 9 (0.150 mmol) (which may be prepared according to U.S. Pat. No. 6,031,094, and the content of which is incorporated herein by reference) and 2 ml of THF are successively introduced into a 20 ml round-bottomed flask with stirring and under an argon atmosphere. Stirring is continued for 3 days at r.t. 20 ml of EtOAc are added to the reaction medium, which is then washed with 10 ml of saturated NaCl solution. The organic phase is dried, filtered and then evaporated to dryness. The crude product is purified by PCC with a 93/7 $CH_2Cl_2$/MeOH mixture (Rf=0.21). 30.57 mg of product 10 are collected (Yld=80%).

TLC (97/3 $CH_2Cl_2$/MeOH): Rf=0.07 $^1$H NMR (300 MHz, CDCl3): δ (ppm)=7.37 & 7.16 (m, 5H); 5.81 (d, 1H); 5.54 (dd, 1H); 5.22 (t, 0.5H); 5.11 (t, 0.5H); 4.30 (d, 1H); 4.13 (t, 1H); 4.05 (m, 1H); 3.98 (m, 1H); 3.64 (m, 1H); 3.60 (m, 1H); 3.54 (d, 3H); 1.48 (s, 3H); 1.33 (s, 3H) 1.05 (s, 9H) LCMS (ES, 30 V): $t_R$=3.72 mn|m/z=491 (MH+HCOOH).

0.466 ml of THF, 38.7 mg (86.66 μmol) of product 10 and then 0.932 ml of HCl (1N) are successively introduced into a round-bottomed flask equipped with a magnetic stirrer. After 50 minutes, the reaction medium is evaporated to dryness. The residue obtained is purified by chromatography on 2 preparative silica plates (20×20 cm, e=0.5 mm, Merck), eluent: $CH_2Cl_2$/MeOH (96/4). 14 mg (40%) of product Example 3 are collected.

$^1$H NMR (400 MHz, CDCl$_3$): 50%-50% mixture of isomers: δ (ppm) 1.04 and 1.05 (2s, 9H); 3.55 and 3.56 (2s, 3H); from 3.51 to 3.71 (m, 2H); from 3.81 to 3.91 (m, 2H); 4.05 (m, 1H); 4.23 (m, 1H); 5.09 and 5.19 (2m, 1H); 5.44 (dd, J=7.5 and 16.5 Hz, 1H); 5.86 (broad d, J=16.5 Hz, 1H); 7.16 (m, 1H); 7.37 (m, 4H); 7.54 (broad t, J=8.5 Hz, 1H). ES: m/z=405 (M−H)$^-$

EXAMPLE 4

N-(2-oxopyrrolidin-3-yl)-(E)-(2R,3R,4S,5R)-3,4,5-trihydroxy-2-methoxy-8,8-dimethylnon-6-enamide

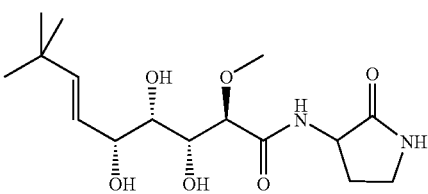

a) Step 1: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-(2-oxopyrrolidin-3-yl) acetamide (12)

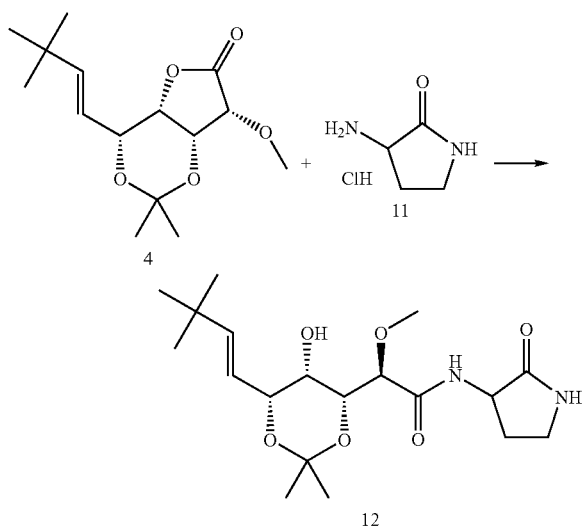

25.40 mg of 4 (0.089 mmol), 47.77 mg of sodium 2-ethylhexanoate (0.287 mmol), 18.49 mg of 11 (which may be prepared according to the procedures described in J. Org. Chem. 1961, 26, 1482-7 the content of which is incorporated herein by reference) (0.135 mmol) and 2 ml of THF are successively introduced into a 20 ml round-bottomed flask with stirring and under an argon atmosphere. Stirring is continued for 4 days at r.t. 20 ml of EtOAc are added to the reaction medium, which is then washed successively with 20 ml of NaOH solution (0.1 N), 20 ml of water and 20 ml of saturated NaCl solution. As product has visibly dissolved in the aqueous phase, this aqueous phase is extracted twice with a mixture of 50 ml of $CH_2Cl_2$ and 5 ml of MeOH. The 3 organic phases are combined, dried, filtered and then evaporated to dryness. The crude product is purified by PCC with a 93/7 $CH_2Cl_2$/MeOH mixture. 27.11 mg of product 12 are collected (Yld=79%).

TLC (90/10 $CH_2Cl_2$/MeOH): Rf=0.21 $^1$H NMR (400 MHz, $CDCl_3$): δ (ppm)=7.08 (d, 0.3H); 6.88 (d, 0.7H); 5.78 (d, 1H); 5.67 (m, 1H); 5.55 (dd, 1H); 4.40 (t, 1H); 4.26 (m, 1H); 4.10 (m, 1H); 3.93 (d, 1H); 3.52 (m, 1H); 3.40 (m, 2H); 3.53 (s, 3H); 2.84 (m, 1H); 1.94 (m, 1H); 1.49 (s, 3H); 1.47 (s, 3H); 1.03 (s, 9H) LCMS (ES+, 30 V): $t_R$=2.84 mn|m/z=769$^+$ (2M+H$^+$); 385$^+$ (M+H$^+$); 327$^+$ (M+H$^+$[(H$_3$C)$_2$CO]); 813 (2 MH+HCOOH); 429 (MH+HCOOH)

b) Step 2: Preparation of N-(2-oxopyrrolidin-3-yl)-(E)-(2R,3R,4S,5R)-3,4,5-trihydroxy-2-methoxy-8,8-dimethylnon-6-enamide (Example 4)

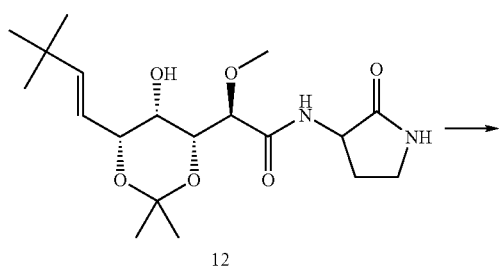

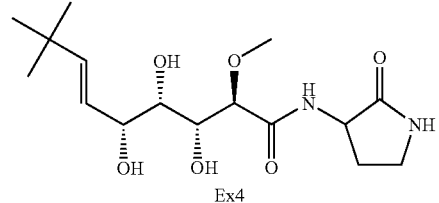

A mixture of 0.6 ml of TFA, 0.6 ml of THF and 0.4 ml of water at 0° C. is introduced into a 30 ml round-bottomed flask containing 24.37 mg of 12 (0.063 mmol), which is also cooled to 0° C. The flask is then stirred at 0° C. and under an argon atmosphere for 40 minutes. The solvents are then evaporated off under vacuum at 0° C., and the product is then freeze-dried in 10 ml of pure water. 22.67 mg of product Example 4 are collected (Yld=96%).

TLC (EtOAc 80/EtOH 15/H$_2$O5): Rf=0.20 $^1$H NMR (400 MHz, CDCl$_3$): δ (ppm)=7.29 (m, 1H); 5.85 (d, 1H, J=16 Hz); 5.43 (dd, 1H); 4.47 (m, 1H); 4.25 (dd, 1H); 3.88 (t, 1H); 3.82 (m, 1H); 3.65 (m, 1H); 3.53 (s, 3H); 3.45 (m, 2H); 2.73 (m, 1H); 2.07 (m, 1H); 1.03 (s, 9H) LCMS (ES+, 30 V): $t_R$=1.96 mn|m/z=689$^+$ (2M+H$^+$); 345$^+$ (M+H$^+$); 327$^+$ (M+H$^+$H$_2$O); 309$^+$ (M+H$^+$2H$_2$O); 291$^+$ (M+H$^+$3H$_2$O); 733 (2 MH+HCOOH); 389 (MH+HCOOH).

EXAMPLE 5

Methyl 5-oxo-4-((E)-(2R,3R,4S,5R)-3,4,5-tri-hydroxy-2-methoxy-8,8-dimethylnon-6-enoylamino) pyrrolidine-2-carboxylate

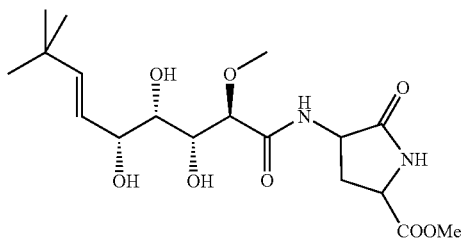

a) Step 1: Preparation of methyl 4-{(R)-2-[(4R,5S,6R)-6-((E)-3,3-dimethylbut-1-enyl)-5-hydroxy-2,2-dimethyl-1,3-dioxan-4-yl]-2-methoxyacetylamino}-5-oxopyrrolidine-2-carboxylate (14)

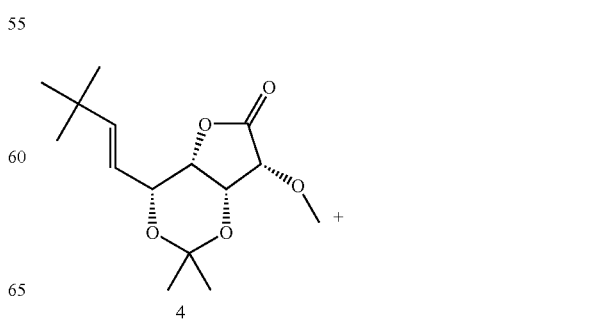

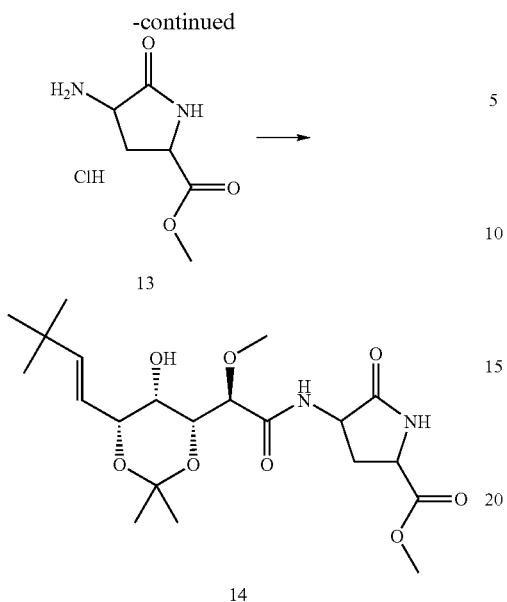

13

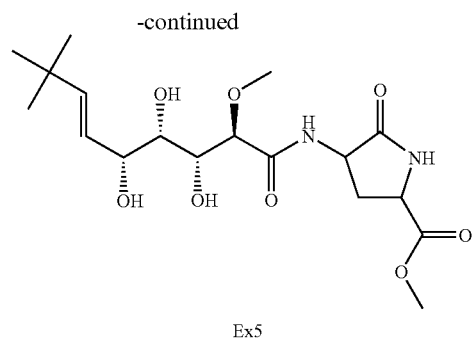

Ex5

A mixture of 0.6 ml of TFA, 0.6 ml of THF and 0.4 ml of water at 0° C. is introduced into a 30 ml round-bottomed flask containing 26.70 mg of 14 (0.055 mmol), which is also cooled to 0° C. The flask is then stirred at 0° C. under an argon atmosphere for 40 minutes. The solvents are then evaporated off under vacuum at 0° C., and the product is then freeze-dried in 10 ml of pure water. 23.20 mg of product Example 5 are collected (Yld=95%).

TLC (90/10 CH$_2$Cl$_2$/MeOH): Rf=0.40 $^1$H NMR (400 MHz, CDCl$_3$): δ (ppm)=7.36 (m, 1H); 7.27 (m, 1H); 5.84 (d, 1H); 5.42 (dd, 1H); 4.50 (m, 1H); 4.25 (m, 1H); 4.22 (m, 1H); 3.87 (dd, 1H); 3.80 (m, 1H); 3.80 (s, 3H); 3.63 (t, 1H); 3.50 (s, 3H); 1.95 (m, 2H); 1.03 (s, 9H) LCMS (ES+, 30 V): $t_R$=2.26 mn|m/z=1207$^+$ (3M+H$^+$); 805$^+$ (2M+H$^+$); 403$^+$ (M+H$^+$); 385$^+$ (M+H$^+$H$_2$O); 367$^+$ (M+H$^+$2H$_2$O); 349$^+$ (M+H$^+$3H$_2$O); 849

14

43.88 mg of sodium 2-ethylhexanoate (0.264 mmol), 25.00 mg of 4 (0.088 mmol), 25.69 mg of 13 (which may be prepared according to the procedures described in U.S. Pat. No. 4,428,960, and the content of which is incorporated herein by reference) (0.132 mmol) and 2 ml of THF are successively introduced into a 5 ml round-bottomed flask with stirring. Stirring is continued for 6 days at r.t. 0.4 ml of DMF is added and stirring is then continued for 5 days at 40° C. 20 ml of EtOAc are added to the reaction medium, which is then washed with 10 ml of saturated NaCl solution. The organic phase is dried, filtered and then evaporated to dryness. The crude product is purified by PCC with a 95/5 CH$_2$Cl$_2$/MeOH mixture. 28.07 mg of product 14 are collected (Yld=72%).

$^1$H NMR (400 MHz, CDCl$_3$): δ (ppm)=7.07 & 6.70 (d, 1H); 5.78 (d, 1H); 5.52 (dd, 1H); 4.50 (m, 1H); 4.27 (dd, 1H); 4.27 (m, 1H); 4.09 (m, 1H); 3.80 (s, 1H); 3.80 (s, 3H); 3.54 (s, 3H); 3.50 (d, 1H); 3.15 (m, 1H); 1.93 (m, 2H); 1.48 (s, 3H); 1.46 (s, 3H); 1.03 (s, 9H) LCMS (ES+/, 30V): $t_R$=2.98 mn|m/z=885$^+$ (2M+H$^+$); 443$^+$ (M+H$^+$); 385$^+$ (M+H$^+$[(H$_3$C)$_2$CO]); 929 (2MH+HCOOH); 487 (MH+HCOOH).

EXAMPLE 6

N-(2-oxopiperidin-3-yl)-(E)-(2R,3R,4S,5R)-3,4,5-trihydroxy-2-methoxy-8,8-dimethylnon-6-enamide

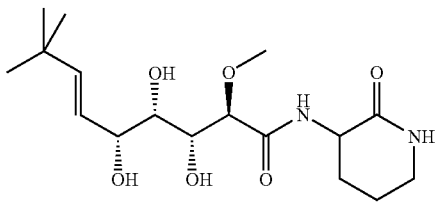

a) Step 1: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-(2-oxopiperidin-3-yl)acetamide 16 b) Step 2: Preparation of methyl 5-oxo-4-((E)-(2R,3R,4S,5R)-3,4,5-trihydroxy-2-methoxy-8,8-dimethylnon-6-enoylamino)pyrrolidine-2-carboxylate (Example 5)

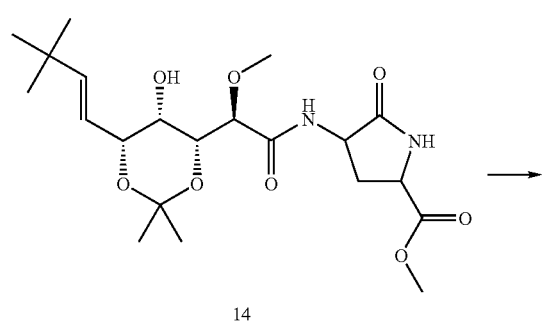

14

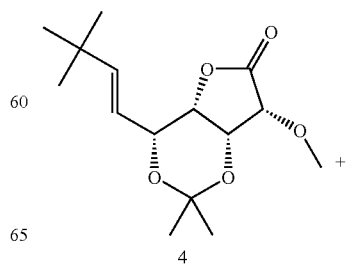

4

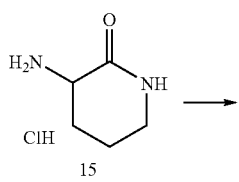

15

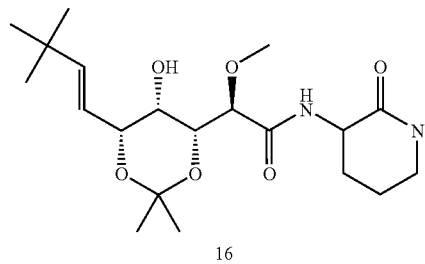

16

24.64 mg of 4 (0.087 mmol), 41.05 mg of sodium 2-ethylhexanoate (0.247 mmol), 20.16 mg of 15 (which may be prepared according to the procedures described in WO 2002/081480, and the content of which is incorporated herein by reference) (0.134 mmol) and 2 ml of THF are successively introduced into a 20 ml round-bottomed flask with stirring and under an argon atmosphere. Stirring is continued for 4 days at r.t. 20 ml of EtOAc are added to the reaction medium, which is then washed successively with 20 ml of NaOH solution (0.1 N), 20 ml of water and 20 ml of saturated NaCl solution. As product has visibly dissolved in the aqueous phase, this aqueous phase is extracted twice with a mixture of 50 ml of $CH_2Cl_2$ and 5 ml of MeOH. The 3 organic phases are combined, dried, filtered and then evaporated to dryness. The crude product is purified by PCC with a 93/7 $CH_2Cl_2$/MeOH mixture. 28.49 mg of product 16 are collected (Yld=83%).

TLC (90/10 $CH_2Cl_2$/MeOH): Rf=0.28 $^1$H NMR (400 MHz, CDCl$_3$): δ (ppm)=7.11 (d, 1H); 5.70 (d, 1H); 5.67 (m, 1H); 5.48 (dd, 1H); 4.72 (m, 1H); 4.20 (d, 1H); 4.02 (d, 1H); 3.80 (d, 1H); 3.50 (s, 1H); 3.49 (s, 3H); 3.36 (m, 2H); 2.54 (m, 2H); 1.96 (m, 2H); 1.47 (s, 6H); 1.02 (s, 9H) LCMS (ES+, 30 V): $t_R$=2.92 mn|m/z=797$^+$ (2M+H$^+$); 399$^+$ (M+H$^+$); 341$^+$ (M+H$^+$[(H$_3$C)$_2$CO]); 841 (2 MH+HCOOH); 443 (MH+HCOOH)

b) Step 2: Preparation of N-(2-oxopiperidin-3-yl)-(E)-(2R,3R,4S,5R)-3,4,5-trihydroxy-2-methoxy-8,8-dimethylnon-6-enamide (Example 6)

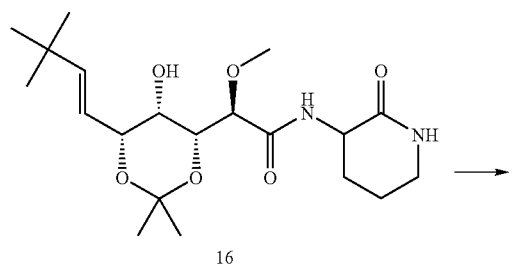

16

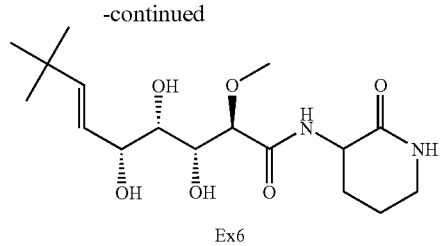

Ex6

A mixture of 0.6 ml of TFA, 0.6 ml of THF and 0.4 ml of water at 0° C. is introduced into a 30 ml round-bottomed flask containing 26.29 mg of 16 (0.066 mmol), which is also cooled to 0° C. The flask is then stirred at 0° C. under an argon atmosphere for 40 minutes. The solvents are then evaporated off under vacuum at 0° C., and the product is then freeze-dried in 10 ml of pure water. 24.56 mg of product Example 6 are collected (Yld=96%).

TLC (80/15/5 EtOAc/EtOH/H$_2$O): Rf=0.22 $^1$H NMR (400 MHz, CDCl$_3$): δ (ppm)=7.44 (d, 1H); 6.12 (m, 1H); 5.84 (d, 1H, J=16 Hz); 5.43 (dd, 1H); 4.39 (m, 1H); 4.25 (dd, 1H); 3.88 (dd, 1H); 3.82 (d, 1H); 3.65 (dd, 1H); 3.52 (s, 3H); 3.38 (m, 2H); 2.48 (m, 1H); 1.95 (m, 2H); 1.70 (m, 1H); 1.03 (s, 9H) LCMS (ES+/, 30 V): $t_R$=2.22 mn|m/z 717$^+$ (2M+H$^+$); 359$^+$ (M+H$^+$); 341$^+$ (M+H$^+$H$_2$O); 323$^+$ (M+H$^+$2H$_2$O); 305$^+$ (M+H$^+$3H$_2$O); 761 (2MH+HCOOH); 403 (MH+HCOOH).

EXAMPLE 7

N-(2-oxo-1,2,3,4-tetrahydroquinolin-3-yl)-(E)-(2R,3R,4S,5R)-3,4,5-trihydroxy-2-methoxy-8,8-dimethylnon-6-enamide

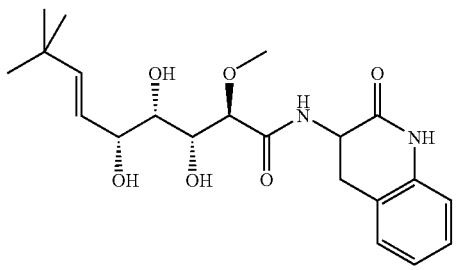

a) Step 1: Preparation of (R)-2-[(4R,5S,6R)-6-((E)-3,3-dimethylbut-1-enyl)-5-hydroxy-2,2-dimethyl-1,3-dioxan-4-yl]]-2-methoxy-N-(2-oxo-1,2,3,4-tetrahydroquinolin-3-yl)-acetamide (18)

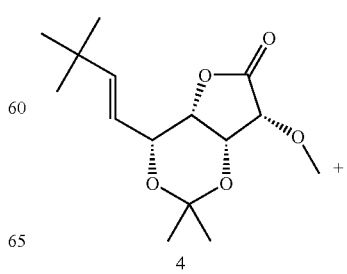

4

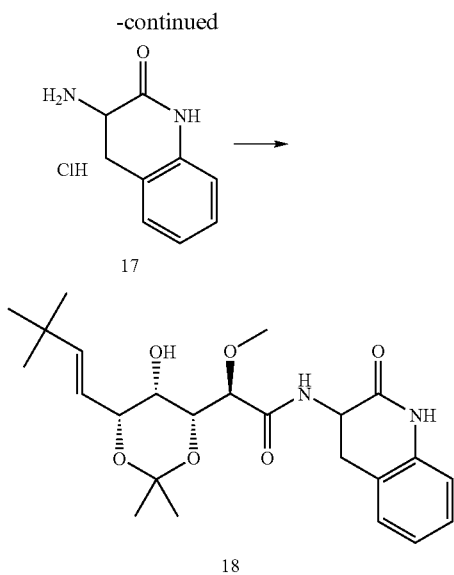

17

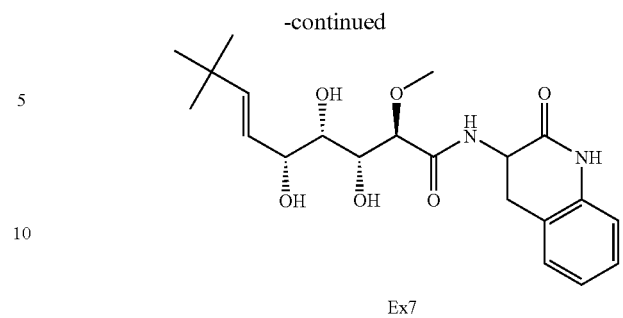

Ex7

0.714 ml of THF, 35.7 mg (80 μmol) of product 18 and then 0.357 ml of HCl (1N) are successively introduced into a round-bottomed flask equipped with a magnetic stirrer. After 2 hours, the reaction medium is cooled (ice/water bath), neutralized with 0.260 ml of NaOH (2N), saturated with NaCl and is then extracted with EtOAc. The organic phase is dried over MgSO₄, filtered and then concentrated under reduced pressure. The residue obtained is purified by chromatography on 2 preparative silica plates (20×20 cm, e=0.5 mm, Merck), eluent: $CH_2Cl_2$/MeOH (90/10). 16 mg (49%) of product Example 7 are collected.

¹H NMR (400 MHz, CDCl₃: 60%-40% mixture of isomers; δ (ppm)=1.02 and 1.04 (2s, 9H); from 2.88 to 3.60 (m, 7H); 3.68 (m, 1H); from 3.81 to 3.93 (m, 2H); from 4.11 to 4.41 (m, 2H); 4.67 (m, 1H); 5.43 (m, 1H); 5.84 (m, 1H); 6.83 (m, 1H); 7.04 (m, 1H); from 7.15 to 7.25 (m, 2H); 7.75 (broad m, 1H); from 7.98 to 8.29 (broad m, 1H).

43.88 mg of sodium 2-ethylhexanoate (0.264 mmol), 25.00 mg of 4 (0.088 mmol), 26.22 mg of 17 (0.132 mmol) (which may be prepared according to the procedures described in J. Med. Chem 1986, 29(12) 2427-32, and the content of which is incorporated herein by reference) and 2 ml of THF are successively introduced into a 5 ml round-bottomed flask with stirring. Stirring is continued for 6 days at r.t. 0.4 ml of DMF is added and stirring is then continued for 5 days at 40° C. 20 ml of EtOAc are added to the reaction medium, which is then washed with 10 ml of saturated NaCl solution. The organic phase is dried, filtered and then evaporated to dryness. The crude product is purified by PCC with a 95/5 $CH_2Cl_2$/MeOH mixture. 36.60 mg of product 18 are collected (Yld=93%).

¹H NMR (400 MHz, CDCl₃): δ (ppm)=7.19 to 6.79 (4H); 5.77 (d, 1H); 5.54 (m, 1H); 4.66 (m, 1H); 4.30 (t, 1H); 4.11 (t, 1H); 3.94 (m, 1H); 3.57 (m, 1H); 3.54 (m, 1H); 3.48 (s, 3H); 2.85 (m, 1H); 1.05 (s, 9H) LCMS (ES+/, 30 V): $t_R$=3.63 mn|m/z=893⁺ (2M+H⁺); 447⁺ (M+H⁺); 389⁺ (M+H⁺[(H₃C)₂CO]); 937 (2 MH+HCOOH); 491 (MH+HCOOH).

EXAMPLE 8

N-(5-oxoperhydro-1,4-thiazepin-6-yl)-(E)-(2R,3R,4S,5R)-3,4,5-trihydroxy-2-methoxy-8,8-dimethyl-non-6-enamide

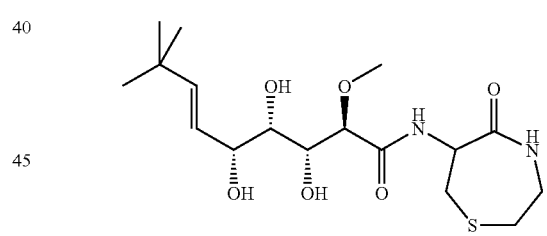

b) Step 2: Preparation of N-(2-oxo-1,2,3,4-tetra-hydroquinolin-3-yl)-(E)-(2R,3R,4S,5R)-3,4,5-trihydroxy-2-methoxy-8,8-dimethylnon-6-enamide (Example 7)

a) Step 1: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-(5-oxoperhydro-1,4-thiazepin-6-yl)acetamide (20)

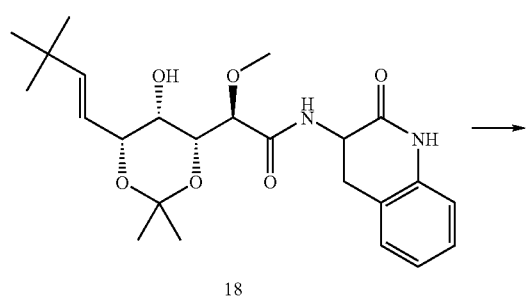

18

4

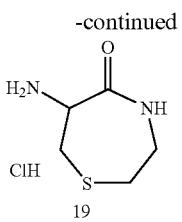

19

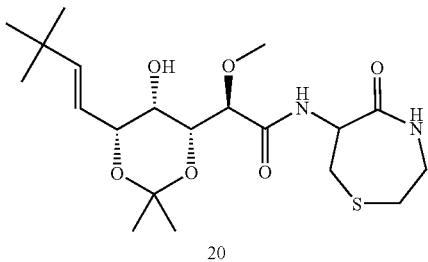

20

25.39 mg of 4 (0.089 mmol), 44.36 mg of sodium 2-ethyl-hexanoate (0.267 mmol), 27.37 mg of 19 (which may be prepared according to the procedures described in WO 2000/005246, and the content of which is incorporated herein by reference) (0.150 mmol) and 2 ml of THF are successively introduced into a 20 ml round-bottomed flask with stirring and under an argon atmosphere. Stirring is continued for 3 days at r.t. 20 ml of EtOAc are added to the reaction medium, which is then successively washed with 20 ml of NaOH solution (0.1 N), 20 ml of water and 20 ml of saturated NaCl solution. The organic phase is dried, filtered and then evaporated to dryness. The crude product is purified by PCC with a 93/7 $CH_2Cl_2$/MeOH mixture. 30.57 mg of product 20 are collected (Yld=80%).

TLC (90/10 $CH_2Cl_2$/MeOH): Rf=0.33 $^1$H NMR (300 MHz, $CDCl_3$): δ (ppm)=7.93 (d, 0.5H); 7.68 (d, 0.5H); 6.03 (m, 1H); 5.81 (d, 1H); 5.56 (m, 1H); 5.00 (m, 1H); 4.30 (t, 1H); 4.10 (d, 1H); 3.94 (d, 1H); 3.71 (m, 2H); 3.57 (m, 1H); 3.53 (s, 3H); 2.80 (m, 2H); 2.70 (m, 2H); 1.49 (s, 3H); 1.47 (s, 3H); 1.04 (s, 9H) LCMS (ES+/, 30 V): $t_R$=3.25 mn|m/z=861$^+$ (2M+H$^+$); 431$^+$ (M+H$^+$); 373$^+$ (M+H$^+$[(H$_3$C)$_2$CO]); 475 (MH+HCOOH).

b) Step 2: Preparation of N-(5-oxoperhydro-1,4-thiazepin-6-yl)-(E)-(2R,3R,4S,5R)-3,4,5-trihydroxy-2-methoxy-8,8-dimethylnon-6-enamide (Example 8)

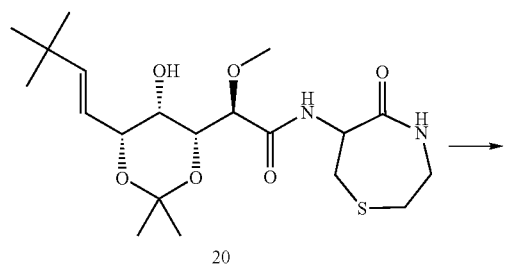

20

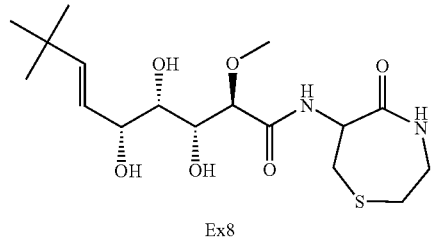

Ex8

A mixture of 0.6 ml of TFA, 0.6 ml of THF and 0.4 ml of water at 0° C. is introduced into a 30 ml round-bottomed flask containing 26.70 mg of 20 (0.062 mmol), which is also cooled to 0° C. The flask is then stirred at 0° C. under an argon atmosphere for 40 minutes. The solvents are then evaporated off under vacuum at 0° C., and the product is then freeze-dried in 10 ml of pure water. 25.75 mg of product Example 8 are collected (Yld=94%).

TLC (90/10 $CH_2Cl_2$/MeOH): Rf=0.23 $^1$H NMR (400 MHz, $CDCl_3$): δ (ppm)=8.12 (m, 1H); 7.27 (m, 1H); 5.83 (d, 1H); 5.43 (dd, 1H); 4.96 (m, 1H); 4.22 (t, 1H); 3.85 (m, 1H); 3.80 (m, 1H); 3.64 (m, 1H); 3.56 (s, 3H); 3.74 (m, 2H); 2.82 (m, 2H); 2.77 (m, 2H); 1.02 (s, 9H) LCMS (ES+/, 30 V): $t_R$=2.56 mn|m/z=1171$^+$ (3M+H$^+$); 781$^+$ (2M+H$^+$); 391$^+$ (M+H$^+$); 373$^+$ (M+H$^+$H$_2$O); 355$^+$ (M+H$^+$2H$_2$O); 337$^+$ (M+H$^+$3H$_2$O); 1215 (3MH+HCOOH); 825 (2 MH+HCOOH); 435 (MH+HCOOH).

EXAMPLE 9

N-((7S,12bR)-6-oxo-1,2,3,4,6,7,8,12b-octa-hydropyrido[2,1-a][2]benzazepin-7-yl)-(E)-(2R,3R,4S,5R)-3,4,5-trihydroxy-2-methoxy-8,8-dimethylnon-6-enamide

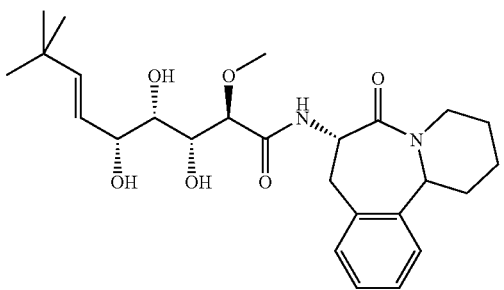

a) Step 1: Preparation of (R)-2-[(4R,5S,6R)-6-((E)-3,3-dimethylbut-1-enyl)-5-hydroxy-2,2-dimethyl-1,3-dioxan-4-yl]-2-methoxy-N-((7S,12bR)-6-oxo-1,2,3,4,6,7,8,12b-octa-hydropyrido[2,1-a][2]benzazepin-7-yl)acetamide (22)

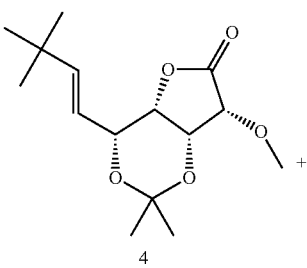

4

-continued

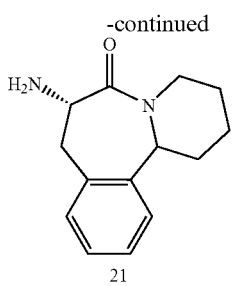

21

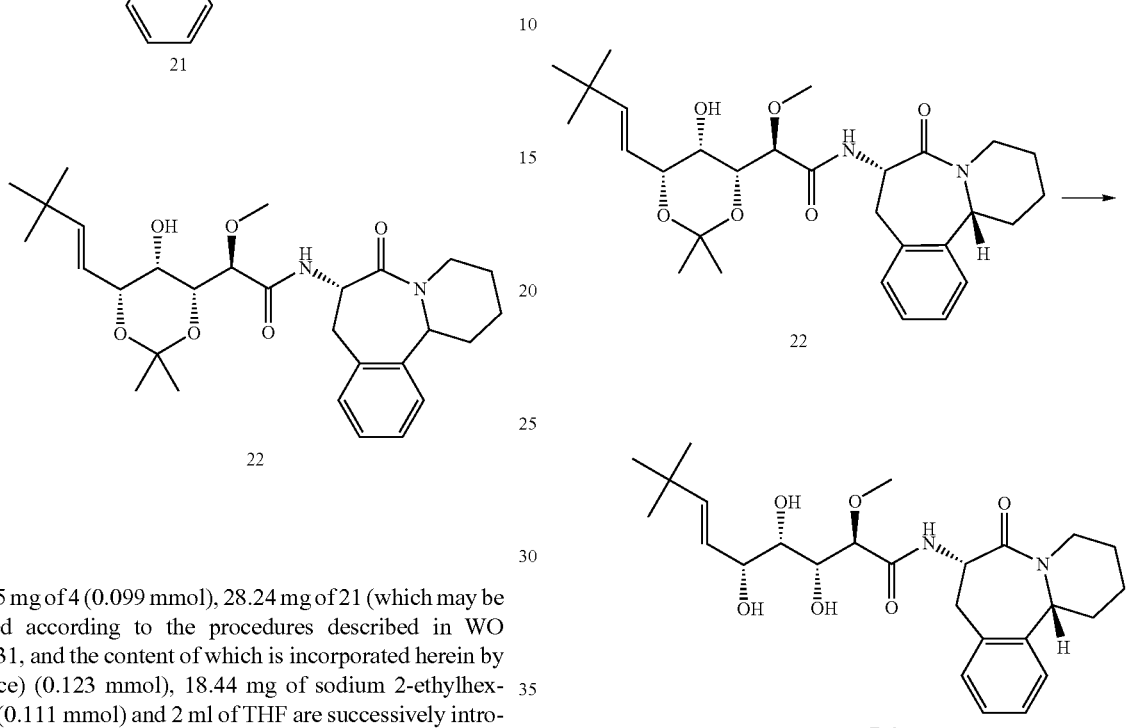

28.15 mg of 4 (0.099 mmol), 28.24 mg of 21 (which may be prepared according to the procedures described in WO 94/04531, and the content of which is incorporated herein by reference) (0.123 mmol), 18.44 mg of sodium 2-ethylhexanoate (0.111 mmol) and 2 ml of THF are successively introduced into a 30 ml round-bottomed flask with stirring and under an inert atmosphere (for example argon, nitrogen or any other acceptable rare gas). Stirring is continued for 3 days at r.t. 11.86 mg of 21 (0.051 mmol) and 9.80 mg of sodium 2-ethylhexanoate (0.059 mmol) are then introduced into the reaction medium. The next day, 20 ml of EtOAc are added to the reaction medium, which is then washed successively with 20 ml of NaOH solution (0.1 N), 20 ml of water and 20 ml of saturated NaCl solution. The organic phase is dried, filtered and then evaporated to dryness. The crude product is purified by PCC with a 70/30 EtOAc/heptane mixture. 43.53 mg of product 22 are collected (Yld=85%).

TLC (95/5 CH$_2$Cl$_2$/MeOH): Rf=0.32 $^1$H NMR (400 MHz, CDCl$_3$): δ (ppm)=7.60 (d, 1H); 7.24 (d, 1H); 7.11 (dt, 2H); 6.98 (d, 1H); 5.72 (d, 1H); 5.55 (dt, 1H); 5.45 (dd, 1H); 5.25 (t, 1H); 4.22 (m, 1H); 4.04 (m, 1H); 3.86 (d, 1H); 3.60 (m, 2H); 3.50 (m, 1H); 3.44 (s, 3H); 2.60 to 1.53 (m, 8H); 1.44 (s, 3H); 1.42 (s, 3H); 0.96 (s, 9H) LCMS (ES+/, 50 V): t$_R$=4.16 mn|m/z=1051$^+$ (2M+Na$^+$); 1029$^+$ (2M+H$^+$); 515$^+$ (M+H$^+$); 457$^+$ (M+H$^+$[(H$_3$C)$_2$CO]); 1073 (2MH+HCOOH) 559 (MH+HCOOH)

b) Step 2: Preparation of N-((7S,12bR)-6-oxo-1,2,3,4,6,7,8,12b-octahydropyrido[2,1-a][2]benzazepin-7-yl)-(E)-(2R,3R,4S,5R)-3,4,5-trihydroxy-2-methoxy-8,8-dimethylnon-6-enamide (Example 9)

A mixture of 0.6 ml of TFA, 0.6 ml of THF and 0.4 ml of water at 0° C. is introduced into a 30 ml round-bottomed flask containing 40.46 mg of 22 (0.079 mmol), which is also cooled to 0° C. The flask is then stirred at 0° C. under an argon atmosphere for 1 hour. The reaction medium is filtered through a Millipore filter, the solvents are then evaporated off under vacuum at 0° C., and the product is then freeze-dried in 10 ml of pure water and 0.5 ml of MeOH. 33.69 mg of product Example 9 are collected (Yld=90%).

TLC (90/10 CH$_2$Cl$_2$/MeOH): Rf=0.22 LCMS (ES+/, 30 V): t$_R$=3.61 mn|m/z=949$^+$ (2M+H$^+$); 475$^+$ (M+H$^+$); 457$^+$ (M+H$^+$H$_2$O); 993 (2MH+HCOOH); 519 (MH+HCOOH).

EXAMPLE 10

N—[(S)-1-(biphenyl-4-ylmethyl)-2-oxoperhydroazepin-3-yl](2R,3R,4S,5S)-6-benzyloxyimino-3,4,5-trihydroxy-2-methoxyhexylamide

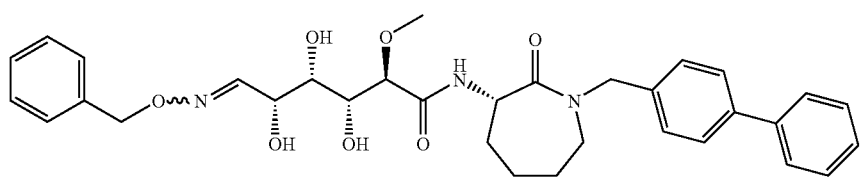

a) Step 1: Preparation of (4S,7R)-7-methoxy-2,2-dimethyl-6-oxotetrahydrofuro[3,2-d]-1,3-dioxan-4-carbaldehyde O-benzyloxime (24)

b) Step 2: Preparation of (R)-2-[(4R,5S,6R)-6-(benzyloxyiminomethyl)-5-hydroxy-2,2-dimethyl-1,3-dioxan-4-yl]-N—[(S)-1-(biphenyl-4-ylmethyl)-2-oxoperhydroazepin-3-yl]-2-methoxyacetamide (25)

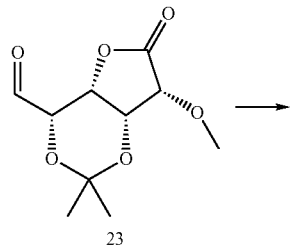

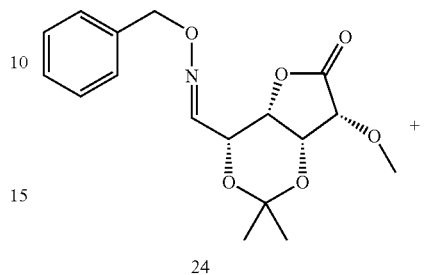

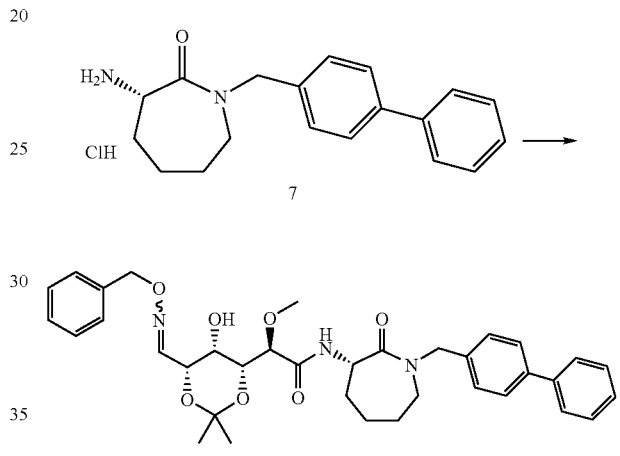

110 mg of O-benzylhydroxylamine hydrochloride (0.689 mmol), 144.6 mg of 23 (0.628 mmol) (which may be prepared according to the procedures described in J. Med. Chem, 2001, 44, 3692-3699, starting with the γ-lactone of α-glucoheptonic acid, and the content of which is incorporated herein by reference), 11.5 ml of $CH_2Cl_2$, 56.2 µl of pyridine (0.689 mmol) and 6 drops of water are successively introduced into a 100 ml round-bottomed flask with stirring and under an inert atmosphere. Stirring is continued for 17 hours at r.t. The solution is diluted by adding 11.5 ml of $CH_2Cl_2$, washed with 23 ml of saturated NaCl solution, dried, filtered and then evaporated to dryness. 215 mg of crude yellow product are collected. The crude product is purified by PCC with a 50/50 EtOAc/heptane mixture (Rf=0.14 & 0.26). 64.7 mg of a first isomer 24, which solidifies to a yellow solid, are collected (Yld=31%). 67.8 mg of the second isomer, which remains in oil form, are collected (Yld=32%).

TLC (80/15/5 EtOAc/EtOH/$H_2O$): Rf=0.28 $^1$H NMR (300 MHz, $CDCl_3$):
  isomer (E): δ (ppm)=7.56 (d, 1H, J=7 Hz); 7.37 (m, 5H); 5.13 (s, 2H); 4.71 (m, 2H); 4.11 (m, 1H); 4.10 (m, 1H); 3.66 (s, 3H); 1.53 (s, 3H); 1.50 (s, 3H)
  isomer (Z): δ (ppm)=7.37 (m, 5H, Ph); 6.84 (d, 1H, J=4 Hz, 6); 5.22 (m, 1H, 5); 5.15 (s, 2H, $OCH_2Ph$); 4.75 (m, 1H, 3); 4.46 (m, 1H, 4); 4.10 (m, 1H, 2); 3.68 (s, 3H, $OCH_3$); 1.57 (s, 3H, $C(CH_3)_2$); 1.55 (s, 3H, $C(CH_3)_2$)

LCMS (ES+/, 50 V): $t_R$=3.42 mn|m/z=671$^+$ (2M+H$^+$); 336$^+$ (M+H$^+$); 278$^+$ (M+H$^+$[(H$_3$C)$_2$CO]); 91$^+$ (Bn$^+$); 715 (2MH+HCOOH); 380 (MH+HCOOH)

35.45 mg of 24 (0.086 mmol), 28.94 mg of 7 (0.119 mmol), 29.45 mg of sodium 2-ethylhexanoate (0.177 mmol) and 1 ml of THF are successively introduced into a 10 ml round-bottomed flask with stirring and under an argon atmosphere. Stirring is continued for 20 hours at r.t. 10 ml of EtOAc are added to the reaction medium, which is then washed successively with 10 ml of NaOH solution (0.1 N), 10 ml of water and 10 ml of saturated NaCl solution. The organic phase is dried, filtered and then evaporated to dryness. The crude product is purified by PCC with a 70/30 EtOAc/heptane mixture. 52.1 mg of product 25 are collected (Yld=96%).

TLC (97/3 $CH_2Cl_2$/MeOH): Rf=0.12 $^1$H NMR (400 MHz, $CDCl_3$): δ (ppm)=7.86 (d, 0.33H, isomer (Z)); 7.81 (d, 0.67H, isomer (E)); 7.57 (d, 0.67H, isomer (E)); 6.79 (d, 0.33H, isomer (Z)); 5.13 (s, 2×0.33H, isomer (Z)); 5.10 (s, 2×0.67H, isomer (E)); 5.03 (m, 0.33, isomer (Z)); 4.81 (m, 1H); 4.72 (m, 1H); 4.56 (m, 1H); 4.47 (m, 0.67H, isomer (E)); 4.18 (m, 0.67H, isomer (E)); 4.16 (d, 0.33H, isomer (Z)); 4.04 (m, 0.33H, isomer (Z)); 3.87 (d, 0.33H, 2, isomer (Z)); 3.83 (d, 0.67H, 2, isomer (E)); 3.74 (m, 0.67H, isomer (E)); 3.50 (m, 1H); 3.30 (m, 1H); 2.10 (m, 1H); 1.85 (m, 1H); 1.75 (m, 1H); 1.49 (s, 3H); 1.48 (m, 2H); 1.47 (s, 3H); 1.35 (m, 1H) LCMS (ES+, 50V): $t_R$=4.41 mn|m/z=1281$^+$ (2M+Na$^+$); 1259$^+$ (2M+H$^+$); 630$^+$ (M+H$^+$); 572$^+$ (M+H$^+$[(H$_3$C)$_2$CO])

c) Step 3: Preparation of N—[(S)-1-(biphenyl-4-ylmethyl)-2-oxoperhydroazepin-3-yl](2R,3R,4S,5R)-6-(benzyloxyimino-3,4,5-trihydroxy-2-methoxyhexylamide (Example 10)

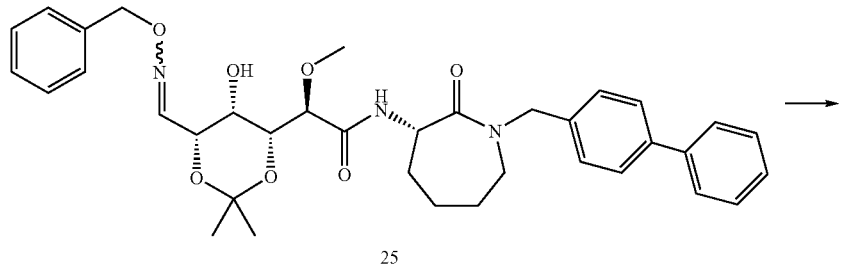

25

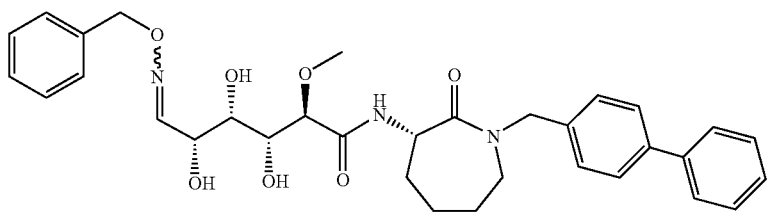

Ex10

A mixture of 0.6 ml of TFA, 0.6 ml of THF and 0.4 ml of water at 0° C. is introduced into a 20 ml round-bottomed flask containing 49.27 mg of 25 (0.078 mmol), which is also cooled to 0° C. The flask is then stirred under an argon atmosphere at 0° C. for 3 hours, and the ice bath is then removed. After 2 hours, the solvents are evaporated off under reduced pressure at 0° C., and the product is then freeze-dried in 10 ml of pure water and 2 drops of MeOH.

The product is purified by PCC with a 93/7 CH$_2$Cl$_2$/MeOH mixture (Rf=0.30). 15.19 mg of product Example 10 are collected (Yld=31%).

TLC (93/7 CH$_2$Cl$_2$/MeOH): Rf=0.30 LCMS (ES+/, 30 V): t$_R$=4.14 mn|m/z=1179$^+$ (2M+H$^+$); 590$^+$ (M+H$^+$); 1223 (2MH+HCOOH); 634 (MH+HCOOH).

EXAMPLE 11

N-(4-benzyl-5-oxoperhydro-1,4-thiazepin-6-yl)-(E)-(2R,3R,4S,5R)-3,4,5-trihydroxy-2-methoxy-8,8-dimethylnon-6-enamide

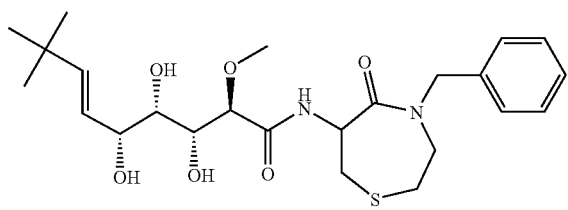

a) Step 1: Preparation of tert-butyl (5-oxoperhydro-1,4-thiazepin-6-yl)carbamate (26)

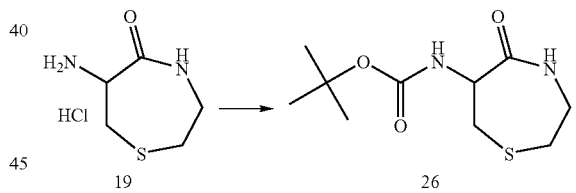

19              26

1.5 g of 19 (8.21 mmol) in 20 ml of chloroform are placed in a 100 ml three-necked flask with stirring, with a condenser and under an argon atmosphere. 2.54 ml of triethylamine (18.07 mmol) are injected in a single portion and the system is placed in an ice bath. 1.79 g of di-tert-butyl dicarbonate (8.21 mmol) in 25 ml of chloroform are then injected dropwise, while taking care to keep the temperature at below 5° C. Stirring is continued for 2 hours 30 minutes, 45 ml of CH$_2$Cl$_2$ are then added and the mixture is washed three times with 50 ml of water. The aqueous phase is extracted with 40 ml of CH$_2$Cl$_2$ and the organic phases are then combined, dried over magnesium sulfate, filtered and evaporated to dryness. 1.814 g of white solid 26 are recovered (yield=64%).

TLC (80/20 EtOAc/cyclohexane): Rf=0.33 $^1$H NMR (400 MHz, DMSO-d$_6$): δ (ppm)=8.03 (m, 1H); 6.54 (d, 1H); 4.48 (m, 1H); 3.48 (m, 2H); 2.6 (m, 4H); 1.37 (s, 9H). LCMS (ES+/−, 30 V): m/z=493$^+$ (2M+H); 247$^+$ (M+H); 146$^+$ (M+H-tBuOCO); 245$^-$ (M−H).

b) Step 2: Preparation of tert-butyl (4-benzyl-5-oxo-perhydro-1,4-thiazepin-6-yl)carbamate (27)

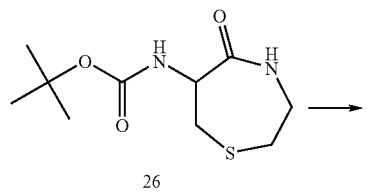

26

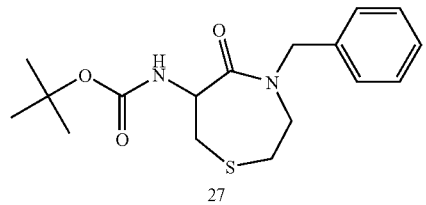

27

448 mg of 26 (1.82 mmol), 67.2 mg of tetrabutylammonium iodide (182 μmol), 216 μl of benzyl bromide (1.82 mmol) and 112 mg of potassium hydroxide (2 mmol) in 18 ml of THF are placed in a 50 ml round-bottomed flask, with stirring and under an argon atmosphere. The white suspension obtained is stirred for 4 days at room temperature. 20 ml of EtOAc are added to the reaction medium and the organic phase is then washed with 3 times 20 ml of water. The organic phase is dried, filtered and then evaporated. 663 mg of crude product are recovered, which product is chromatographed on silica with an 80/20 heptane/EtOAc mixture. 417 mg of product 27 are thus recovered (yield=68%).

TLC (80/20 heptane/EtOAc): Rf=0.25 $^1$H NMR (400 MHz, DMSO-$d_6$): δ (ppm)=7.3 (m, 5H); 6.78 (d, 1H); 4.77 (m, 1H); 4.74 and 4.38 (dd, 2H); 3.8 and 3.6 (m, 2H); 2.6 (m, 4H); 1.39 (s, 9H).

LCMS (ES+/−, 30 V): m/z=673$^+$ (2M+H); 337$^+$ (M+H); 236$^+$ (M+H-tBuOCO); 246$^+$ (M+H—Bn); 335$^-$ (M−H).

c) Step 3: Preparation of 6-amino-4-benzylperhydro-1,4-thiazepin-5-one hydrochloride (28)

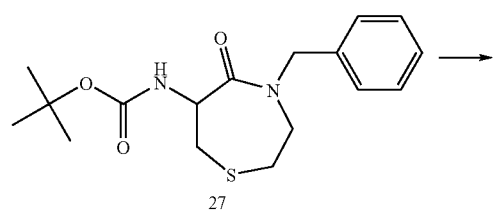

27

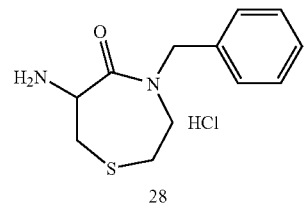

28

405 mg of 28 (1.22 mmol) are taken up in 1 ml of EtOAc and 28 ml of a solution of hydrogen chloride in dioxane (4M) are added. The mixture is stirred overnight at room temperature under argon. The solvents are then evaporated off and the residue is dried under vacuum. 327 mg of amine 28 are obtained in hydrochloride form, which product is used directly in the following step.

LCMS (ES+/−, 30 V): m/z=473$^+$ (2M+H); 237$^+$ (M+H); 146$^+$ (M+H—Bn); 235$^-$ (M−H) $^1$H NMR (400 MHz, DMSO-$d_6$): δ (ppm)=8.38 (broad s, 1H); 7.32 (m, 5H); 4.83 and 4.36 (dd, 2H); 4.72 (m, 1H); 3.85 and 3.7 (m, 2H); 2.9-2.5 (m, 4H).

d) Step 4: Preparation of (R)—N-(4-benzyl-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (29)

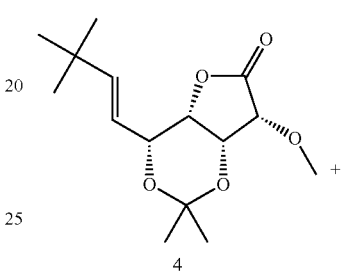

4

+

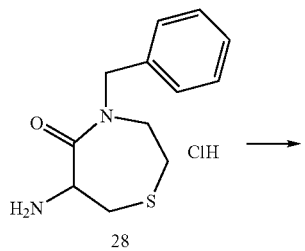

28

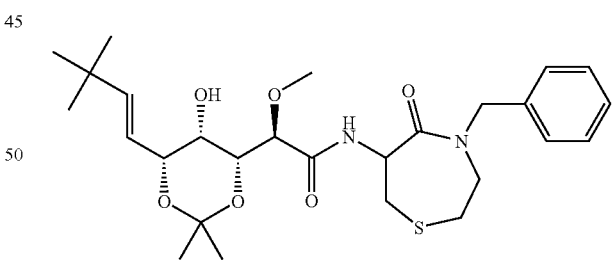

29

116 mg of 4 (407 μmol), 140 mg of 28 (513 μmol), 169 mg of sodium 2-ethylhexanoate (1.02 mmol) and 10 ml of THF are successively introduced into a 50 ml round-bottomed flask, with stirring and under an argon atmosphere. Stirring is continued at room temperature for 4 days. 40 ml of ethyl acetate are added to the reaction medium. The mixture is washed successively with 40 ml of 0.1M sodium hydroxide solution and then with 40 ml of water and 40 ml of saturated NaCl solution. The organic phase is dried over anhydrous magnesium sulfate, filtered and then evaporated to dryness. 340 mg of a yellowish gum are obtained, which product is chromatographed on silica (eluent: 97/3 CH$_2$Cl$_2$/MeOH). 184 mg of product 29 are collected (yield=87%).

TLC (97/3 CH$_2$Cl$_2$/MeOH): Rf=0.34 LCMS (ES+/−50 V): m/z=1043$^+$ (2M+H); 522$^+$ (M+H); 464$^+$ (M+H−CO(CH$_3$)$_2$); 1087$^-$ (2M−H+HCOOH); 566$^-$ (M−H+HCOOH); 520$^-$ (M−H). $^1$H NMR (400 MHz, DMSO-d$_6$): δ (ppm)=8.05 (dd, 1H); 7.35 (m, 5H); 5.69 (d, 1H); 5.45 (dd, 1H); 5.05 (m, 1H); 4.75 and 4.4 (dd, 2H); 4.53 (d, 1H); 4.29 (m, 1H); 4.0-3.6 (m, 4H); 3.28 (m, 4H); 2.6 (m, 4H); 1.3 (d, 6H); 1.0 (s, 9H).

e) Step 5: Preparation of N-(4-benzyl-5-oxoperhydro-1,4-thiazepin-6-yl)-(E)-(2R,3R,4S,5R)-3,4,5-trihydroxy-2-methoxy-8,8-dimethylnon-6-enamide (Example 11)

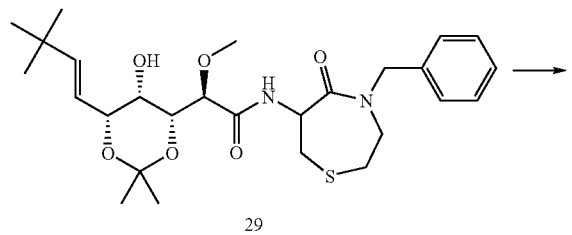

29

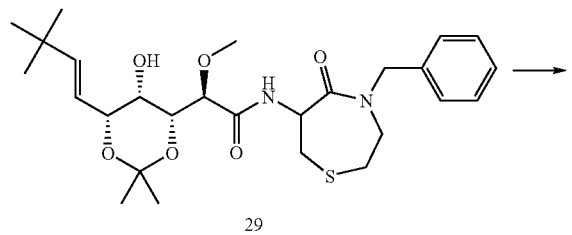

Ex11

340 mg of 29 (653 μmol) are mixed with 3.8 ml of THF and 6.8 ml of 1N hydrochloric acid, with stirring and under argon. Stirring is continued for 4 hours at room temperature. Next, the solution is cooled to 5° C. and neutralized to pH 7.0 with 2N sodium hydroxide. 2.5 g of NaCl are added. The mixture is warmed to room temperature. 5 ml of EtOAc are added. The organic phase is separated out, dried over magnesium sulfate, filtered and then evaporated to dryness. 228 mg of crude product are collected, which product is then chromatographed on silica with an elution gradient of from pure CH$_2$Cl$_2$ to 90/10 CH$_2$Cl$_2$/MeOH. 153 mg of product Example 11 are obtained (yield=49%).

TLC (90/10 CH$_2$Cl$_2$/MeOH): Rf=0.44 LCMS (ES+/−, 50 V): m/z=969$^+$ (2M+H); 482$^+$ (M+H); 464$^+$ (M+H−H$_2$O); 446$^+$ (M+H−2H$_2$O); 428$^+$ (M+H−3H$_2$O); 1007$^-$ (2M−H+HCOOH); 526$^-$ (M−H+HCOOH); 480$^-$ (M−H). $^1$H NMR (400 MHz, DMSO-d$_6$): δ (ppm)=8.05 (dd, 1H); 7.3 (m, 5H); 5.65 (d, 1H); 5.35 (dd, 1H); 5.02 (m, 1H); 4.75 and 4.40 (dd, 2H); 4.58 (m, 2H,); 4.3 (m, 1H); 4.02 and 3.74 (dd, 2H); 3.98 (m, 1H); 3.83 (m, 1H); 3.6 (m, 1H); 3.35 (m, 1H); 3.25 (s, 3H); 2.8-2.4 (m, 4H); 0.97 (s, 9H).

EXAMPLE 12

N-(4-(3,4-difluorobenzyl)-5-oxoperhydro-1,4-thiazepin-6-yl)-(E)-(2R,3R,4S,5R)-3,4,5-trihydroxy-2-methoxy-8,8-dimethylnon-6-enamide

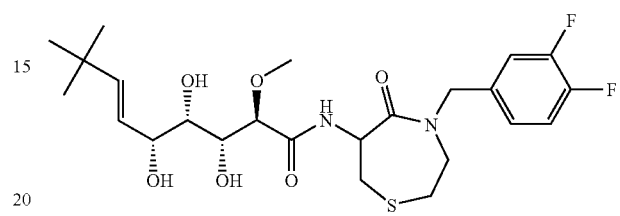

a) Step 1: Preparation of tert-butyl [4-(3,4-difluorobenzyl)-5-oxoperhydro-1,4-thiazepin-6-yl]-carbamate (30)

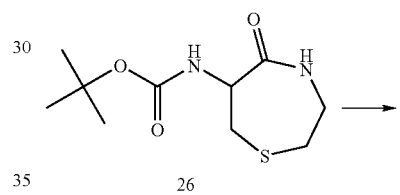

26

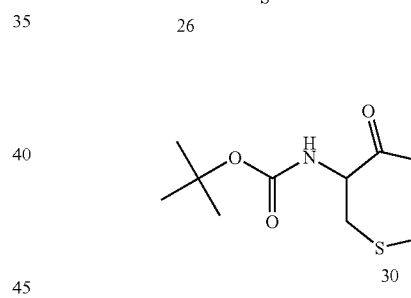

30

81 mg of sodium hydride as a 60% suspension in oil (2.03 mmol) are introduced at room temperature into a 50 ml round-bottomed flask, with stirring and under an argon atmosphere, containing 20 ml of THF and 500 mg of 26 (2.03 mmol). The medium is stirred for 1 hour and 420 mg (2.03 mmol) of 3,4-difluorobenzyl bromide are then added. The medium is stirred overnight, 20 ml of EtOAc and 20 ml of water are added to the reaction medium and, after separation of the phases by settling, the organic phase is washed once with 20 ml of water. The organic phase is dried, filtered and then evaporated to dryness. 1.5 g of crude product are recovered, which product is chromatographed on silica (eluent: 80/20 heptane/EtOAc). 460 mg of product 30 are recovered (yield=61%).

$^1$H NMR (400 MHz, CDCl$_3$), δ (ppm): 1.46 (s, 9H); from 2.42 to 2.58 (m, 2H); 2.72 (dd, J=9.5 and 14.5 Hz, 1H); 2.85 (d, J=14.5 Hz, 1H); 3.61 (broad d, J=16.0 Hz, 1H); 3.87 (broad dd, J=8.5 and 16.0 Hz, 1H); 4.31 (d, J=14.5 Hz, 1H); 4.83 (d, J=14.5 Hz, 1H); 4.86 (partially masked m, 1H); 6.10 (broad d, J=6.0 Hz, 1H); 6.98 (broad m, 1H from 7.05 to 7.17 (m, 2H).

b) Step 2: Preparation of 6-amino-4-(3,4-difluoro-benzyl)perhydro-1,4-thiazepin-5-one hydrochloride (31)

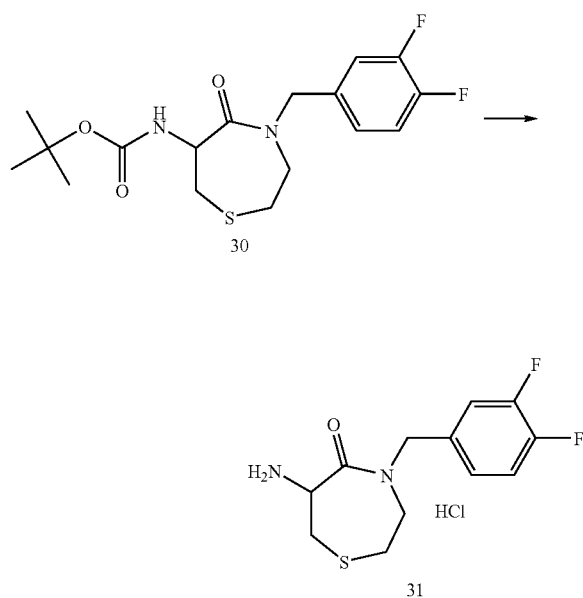

460 mg of 30 (1.235 mmol) are taken up in a 25 ml round-bottomed flask and 9.3 ml of a solution of hydrogen chloride in dioxane (4M) are added. The medium is stirred for 4 hours at room temperature under argon. After evaporating off the solvent, 460 mg of amine 31 are obtained in hydrochloride form, which product is used directly in the following step.

$^1$H NMR (300 MHz DMSO-d6), δ (ppm): from 2.53 to 2.73 (m, 2H); 2.75 (dd, J=9.0 and 14.5 Hz, 1H); 2.93 (dd, J=4.0 and 14.5 Hz, 1H); from 3.62 to 3.75 (masked m, 1H); from 3.80 to 3.95 (m, 1H); 4.30 (d, J=15.0 Hz, 1H); 4.75 (dd, J=4.0 and 9.0 Hz, 1H); 4.82 (d, J=15.0 Hz, 1H); 7.17 (m, 1H); from 7.32 to 7.47 (m, 2H); 8.49 (broad m, 3H).

c) Step 3: Preparation of (R)—N-(4-(3,4-difluorobenzyl)-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (32)

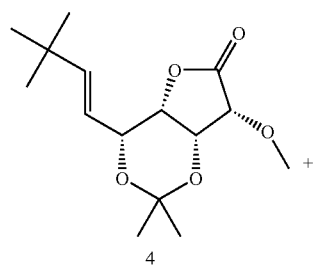

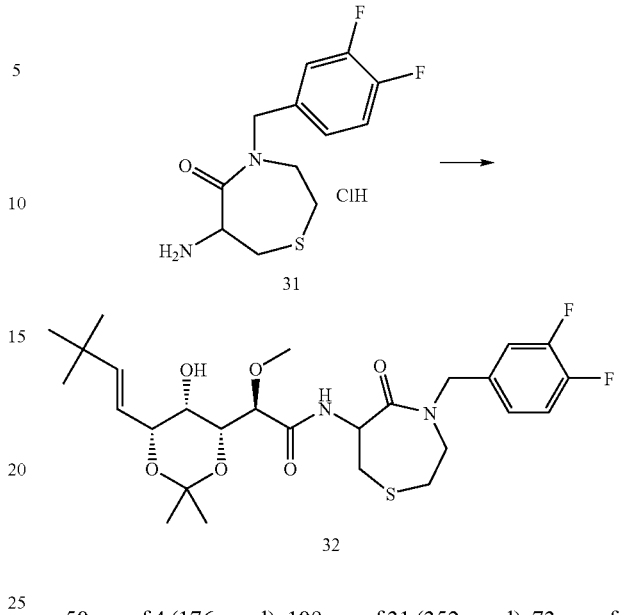

50 mg of 4 (176 μmol), 109 mg of 31 (352 μmol), 73 mg of sodium 2-ethylhexanoate (440 μmol) and 1 ml of THF are successively introduced into a Wheaton tube, with stirring and under an argon atmosphere. Stirring is continued at room temperature for 3 days. 3 ml of ethyl acetate are added to the reaction medium. The mixture is washed successively with 3 ml of HCl solution (1N) and then with 3 ml of saturated NaHCO$_3$ solution and 3 ml of water. The organic phase is dried over anhydrous magnesium sulfate, filtered and then evaporated to dryness. 100 mg of a yellow oil are obtained, which product is chromatographed on a cartridge of NH$_2$-grafted silica (3 g, eluent, 75/25 heptane/EtOAc). 54 mg of expected product 32 are collected (yield=50%).

$^1$H NMR (400 MHz DMSO-d6), a 50%-50% mixture of isomers with δ (ppm): 0.99 (s, 9H); 1.27 (s, 3H); 1.32 (s, 1.5H); 1.33 (s, 1.5H); from 2.51 to 2.75 (m, 4H); from 3.24 to 3.31 (partially masked m, 1H); 3.29 (s, 3H); 3.66 (m, 1H); 3.79 (d, J=8.5 Hz, 0.5H); 3.84 (d, J=8.5 Hz, 0.5H); 3.88 (m, 1H); 3.95 (m, 1H); 4.28 (m, 1H); 4.34 (m, 1H); 4.45 (d, J=8.5 Hz, 0.5H); 4.57 (d, J=8.5 Hz, 0.5H); 4.76 (m, 1H); 5.06 (m, 1H); 5.47 (dd, J=7.5 and 16.0 Hz, 1H); 5.69 (d, J=16.0 Hz, 1H); 7.14 (m, 1H); from 7.31 to 7.43 (m, 2H); 8.03 (d, J=6.5 Hz, 0.5H); 8.07 (d, J=6.5 Hz, 0.5H).

e) Step 4: Preparation of N-(4-(3,4-difluorobenzyl)-5-oxoperhydro-1,4-thiazepin-6-yl)-(E)-(2R,3R,4S,5R)-3,4,5-trihydroxy-2-methoxy-8,8-dimethylnon-6-enamide (Example 12)

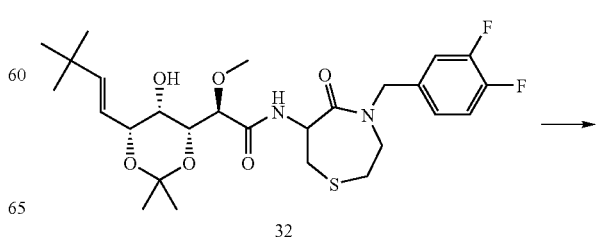

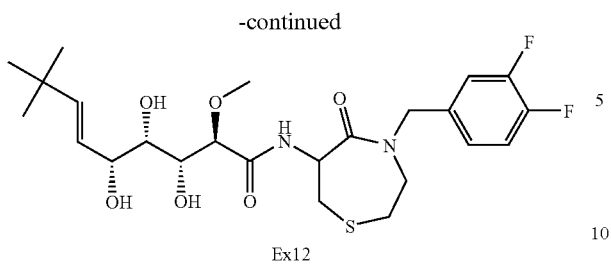

Ex12

54 mg of 32 (97 µmol) are mixed in 0.5 ml of THF and 0.97 ml of 1N hydrochloric acid, with stirring and under argon. Stirring is continued for 5 hours at room temperature. The solution is then neutralized to pH 7.0 with 1N sodium hydroxide. The mixture is extracted twice with 5 ml of EtOAc. The organic phases are combined, dried over magnesium sulfate and filtered, and then evaporated to dryness. 38.5 mg of product Example 12 are obtained (yield=77%).

ES: 517(+)=(M+H)(+); 499(+)=(M+H)(+) —H$_2$O $^1$H NMR (400 MHz, DMSO-d6), a 50/50 mixture of 2 isomers, with δ (ppm): 0.97 (s, 9H); from 2.52 to 2.77 (partially masked m, 4H); from 3.23 to 3.38 (partially masked m, 1H); 3.26 (s, 1.5H); 3.28 (s, 1.5H); from 3.54 to 3.72 (m, 2H); 3.73 (d, J=7.0 Hz, 0.5H); 3.74 (d, J=7.0 Hz, 0.5H); 3.88 (m, 1H); 3.98 (m, 1H); from 4.32 to 4.39 (m, 2H); 4.50 (d, J=7.5 Hz, 0.5H); 4.58 (m, 1.5H); 4.74 (d, J=15.0 Hz, 1H); 5.04 (m, 1H); 5.34 (m, 1H); 5.63 (broad d, J=16.0 Hz, 1H); 7.14 (m, 1H); from 7.29 to 7.44 (m, 2H); 8.03 (d, J=6.5 Hz, 0.5H); 8.07 (d, J=6.5 Hz, 0.5H).

EXAMPLE 13

N-(4-(3,5-difluorobenzyl)-5-oxoperhydro-1,4-thiazepin-6-yl)-(E)-(2R,3R,4S,5R)-3,4,5-trihydroxy-2-methoxy-8,8-dimethylnon-6-enamide

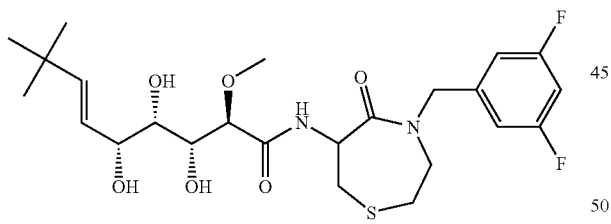

a) Step 1: Preparation of tert-butyl [4-(3,5-difluorobenzyl)-5-oxoperhydro-1,4-thiazepin-6-yl]carbamate (33)

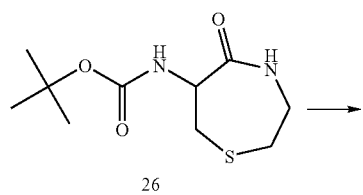

26

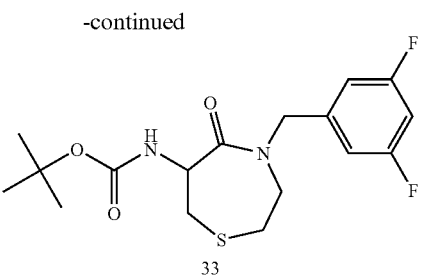

33

121 mg of sodium hydride as a 60% suspension in oil (3.05 mmol) are introduced at room temperature into a 50 ml round-bottomed flask, with stirring and under an argon atmosphere, containing 20 ml of DMF and 500 mg of 26 (2.03 mmol). The medium is stirred for 1 hour and 454 mg (2.03 mmol) of 3,5-difluorobenzyl bromide are then added. The medium is stirred for 3 hours, 50 ml of EtOAc and 50 ml of water are added to the reaction medium and, after separation of the phases by settling, the organic phase is washed with 50 ml of water. The organic phase is dried, filtered and then evaporated to dryness. 1.5 g of crude product are recovered, which product is chromatographed on a silica cartridge (20 g, eluent: 80/20 heptane/EtOAc). 600 mg of product 33 are recovered (yield=79%).

$^1$H NMR (300 MHz, DMSO-d6), δ (ppm): 1.39 (s, 9H); from 2.54 to 2.77 (m, 4H); 3.64 (m, 1H); 3.86 (m, 1H); 4.32 (d, J=15.5 Hz, 1H); 4.77 (masked m, 1H); 4.80 (d, J=15.5 Hz, 1H); 6.76 (d, J=6.5 Hz, 1H); 7.00 (m, 2H); 7.11 (tt, J=2.5 and 9.5 Hz, 1H).

b) Step 2: Preparation of 6-amino-4-(3,5-difluorobenzyl)-perhydro-1,4-thiazepin-5-one hydrochloride (34)

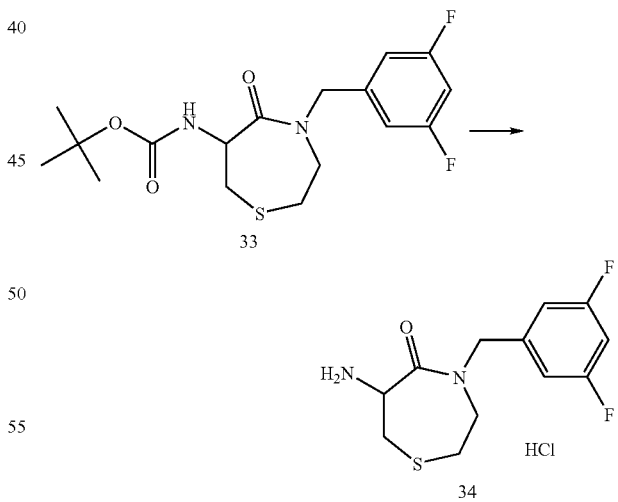

230 mg of 33 (1.235 mmol) are taken up in a 25 ml round-bottomed flask and 5 ml of a solution of hydrogen chloride in dioxane (4M) are added. The medium is stirred for 2 hours at room temperature under argon. After evaporating off the solvent, 230 mg of amine 34 are obtained in hydrochloride form, which product is used directly in the following step.

$^1$H NMR (400 MHz, DMSO-d6), δ (ppm): from 2.62 to 2.72 (m, 2H); 2.77 (dd, J=8.5 and 14.5 Hz, 1H); 2.90 (dd, J=4.0 and 14.5 Hz, 1H); 3.74 (m, 1H); 3.91 (m, 1H); 4.29 (d, J=15.5 Hz, 1H); 4.79 (m, 1H); 4.91 (d, J=15.5 Hz, 1H); 7.03 (m, 2H); 7.15 (tt, J=2.5 and 9.5 Hz, 1H); 8.44 (broad m, 3H).

c) Step 3: Preparation of (R)—N-(4-(3,5-difluorobenzyl)-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (35)

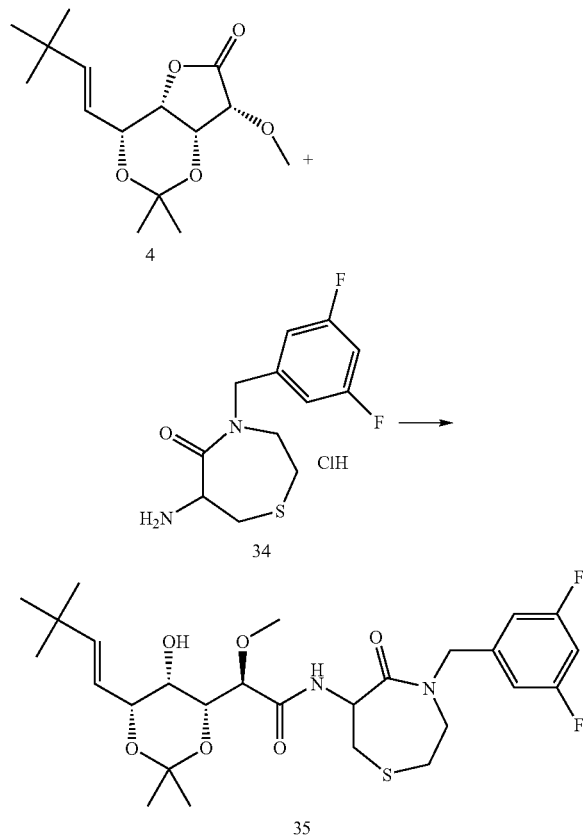

50 mg of 4 (176 μmol), 217 mg of 34 (352 μmol), 132 mg of sodium 2-ethylhexanoate (754 μmol) and 2.5 ml of THF are successively introduced into a Wheaton tube, with stirring and under an argon atmosphere. Stirring is continued at room temperature for 3 days. 10 ml of ethyl acetate are added to the reaction medium. The mixture is washed successively with 10 ml of HCl solution (1N) and then with 10 ml of saturated NaHCO₃ solution and 10 ml of saturated aqueous NaCl. The organic phase is dried over anhydrous magnesium sulfate, filtered and then evaporated to dryness. 120 mg of a yellow oil are obtained, which product is chromatographed on a cartridge of NH₂-grafted silica (3 g, eluent: CH₂Cl₂). 48 mg of expected product 35 are collected (yield=49%).

¹H NMR (400 MHz, CDCl₃), a 50/50 mixture of 2 isomers, with δ (ppm): 1.03 (s, 4.5H); 1.04 (s, 4.5H); 1.45 (s, 1.5H); 1.46 (s, 1.5H); 1.49 (s, 3H); from 2.49 to 2.62 (m, 2H); 2.68 (dd, J=9.5 and 14.5 Hz, 0.5H); 2.73 (dd, J=9.5 and 14.5 Hz, J=0.5H); 2.78 (d, J=9.5 Hz, 1H); 2.84 (dd, J=3.0 and 14.5 Hz, 0.5H); 2.90 (dd, J=3.0 and 14.5 Hz, 0.5H); 3.44 (d, J=3.5 Hz, 0.5H); from 3.50 to 3.58 (partially masked m, 0.5H); 3.51 (s, 1.5H); 3.55 (s, 1.5H); from 3.60 to 3.68 (m, 1H); from 3.87 to 3.98 (m, 2H); from 4.08 to 4.11 (m, 1H); 4.29 (m, 1H); 4.36 (broad d, J=15.5 Hz, 1H); 4.86 (d, J=15.5 Hz, 1H); 5.14 (m, 1H); 5.53 (dd, J=6.5 and 16.0 Hz, 0.5H); 5.57 (dd, J=6.5 and 16.0 Hz, 0.5H); 5.78 (d, J=16.0 Hz, 1H); from 6.72 to 6.83 (m, 3H); 7.77 (d, J=6.0 Hz, 0.5H); 8.00 (d, J=6.0 Hz, 0.5H).

e) Step 4: Preparation of N-(4-(3,5-difluorobenzyl)-5-oxoperhydro-1,4-thiazepin-6-yl)-(E)-(2R,3R,4S,5R)-3,4,5-trihydroxy-2-methoxy-8,8-dimethylnon-6-enamide (Example 13)

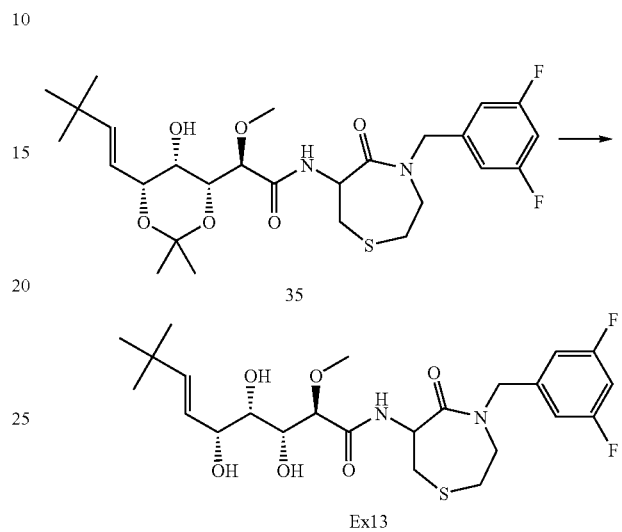

48 mg of 35 (97 μmol) are mixed with 0.42 ml of THF and 0.92 ml of 1N hydrochloric acid, with stirring and under argon. Stirring is continued for 4 hours at room temperature. The solution is then neutralized to pH 7.0 with 1N sodium hydroxide. The mixture is extracted twice with 2 ml of EtOAc. The organic phases are combined, dried over magnesium sulfate and filtered and then evaporated to dryness. 33.5 mg of product Example 13 are obtained (yield=55%).

ES: 517(+)=(M+H)(+); 499(+)=(M+H)(+) —H₂O ¹H NMR (400 MHz, CDCl₃), 60%-40% resolution of isomers with δ (ppm): 1.04 (s, 9H); from 2.48 to 3.04 (m, 4H); 3.20 (d, J=7.0 Hz, 0.4H); 3.35 (d, J=7.0 Hz, 0.6H); 3.59 (s, 3H); from 3.60 to 3.70 (m, 2H); from 3.77 to 3.87 (m, 2H); 3.93 (m, 1H); 4.08 (broad s, 0.6H); 4.19 (broad s, 0.4H); 4.25 (m, 1H); 4.41 (m, 1H); 4.83 (m, 1H); 5.11 (m, 1H); 5.44 (dd, J=8.0 et 16.5 Hz, 1H); 5.85 (d, J=16.5 Hz, 1H); from 6.76 to 6.84 (m, 3H); 8.24 (d, J=6.5 Hz, 0.6H); 8.29 (d, J=6.5 Hz, 0.4H).

EXAMPLE 14

N-(4-(2,6-dichloropyrid-4-ylmethyl)-5-oxo-perhydro-1,4-thiazepin-6-yl)-(E)-(2R,3R,4S,5R)-3,4,5-trihydroxy-2-methoxy-8,8-dimethylnon-6-enamide

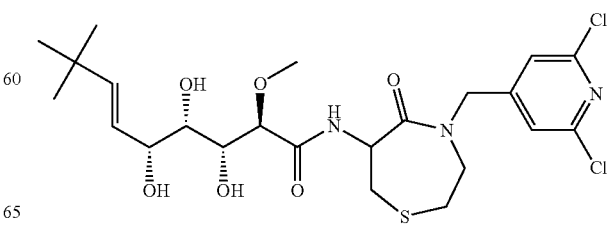

a) Step 1: Preparation of tert-butyl [4-(2,6-dichloro-pyrid-4-ylmethyl)-5-oxoperhydro-1,4-thiazepin-6-yl] carbamate (36)

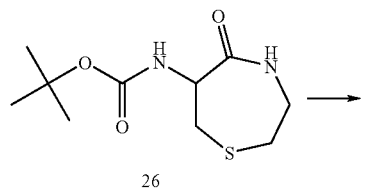

26

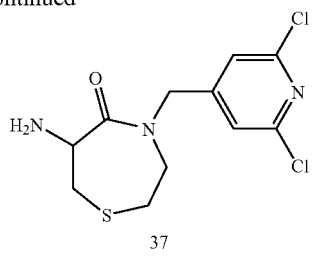

36

121 mg of sodium hydride as a 60% suspension in oil (3.05 mmol) are introduced at room temperature into a 50 ml round-bottomed flask, with stirring and under an argon atmosphere, containing 20 ml of DMF and 500 mg of 26 (2.03 mmol). The medium is stirred for 1 hour and 489 mg (2.03 mmol) of 4-bromomethyl-2,6-dichloropyridine are then added. The medium is stirred for 3 hours, 50 ml of EtOAc and 50 ml of water are added to the reaction medium and, after separation of the phases by settling, the organic phase is washed once with 50 ml of water. The organic phase is dried, filtered and then evaporated to dryness. 1.5 g of crude product are recovered, which product is chromatographed on a silica cartridge (20 g) with an 80/20 heptane/EtOAc mixture. 190 mg of product 36 are recovered (yield=23%).

$^1$H NMR (300 MHz, DMSO-d6), δ (ppm): 1.39 (s, 9H); from 2.59 to 2.79 (m, 4H); 3.67 (m, 1H); 3.94 (m, 1H); 4.32 (d, J=16.5 Hz, 1H); 4.81 (partially masked m, 1H); 4.87 (d, J=16.5 Hz, 1H); 6.80 (d, J=6.5 Hz, 1H); 7.46 (s, 2H).

b) Step 2: Preparation of 6-amino-4-(2,6-dichloropy-rid-4-ylmethyl)perhydro-1,4-thiazepin-5-one hydrochloride (37)

36

-continued

37

230 mg of 36 (0.57 mmol) are taken up in a 25 ml round-bottomed flask and 3 ml of a solution of hydrogen chloride in dioxane (4M) are added. The mixture is stirred for 2 hours at room temperature under argon. After evaporating off the solvent, 290 mg of amine 37 are obtained in hydrochloride form, which product is used directly in the following step.

$^1$H NMR (300 MHz, DMSO-d$_6$), δ(ppm): from 2.66 to 2.81 (m, 3H); 2.91 (dd, J=4.5 and 15.0 Hz, 1H); from 3.63 to 3.76 (masked m, 1H); 3.96 (m, 1H); 4.31 (d, J=16.5 Hz, 1H); 4.83 (m, 1H); 4.95 (d, J=16.5 Hz, 1H); 7.48 (s, 2H); 8.44 (broad s, 3H).

c) Step 3: Preparation of (R)—N-(4-(2,6-dichloropy-rid-4-ylmethyl)-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (38)

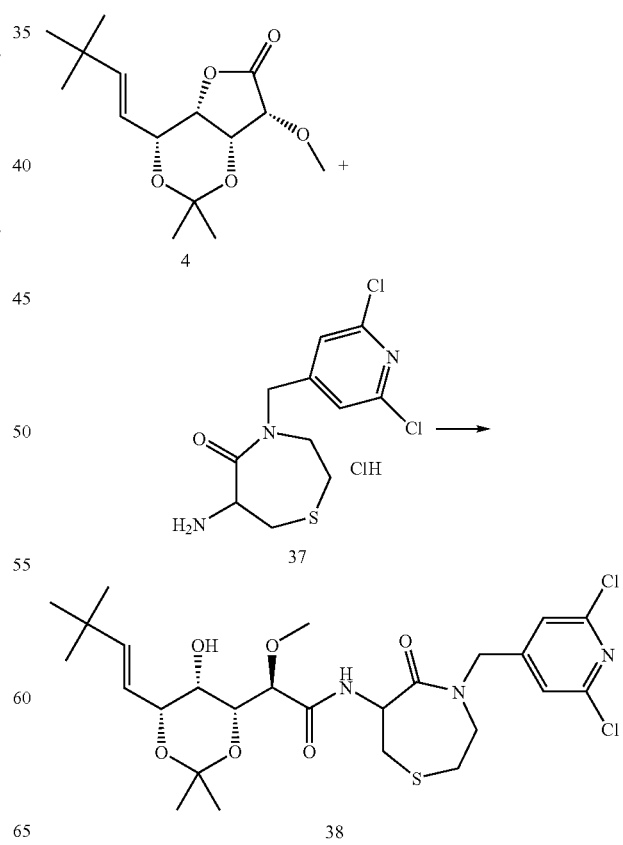

50 mg of 4 (176 µmol), 290 mg of 37 (339 µmol), 99 mg of sodium 2-ethylhexanoate (595 µmol) and 2.5 ml of THF are successively introduced into a Wheaton tube, with stirring and under an argon atmosphere. Stirring is continued at room temperature for 3 days. 10 ml of ethyl acetate are added to the reaction medium. The mixture is washed successively with 10 ml of HCl solution (1N) and then with 10 ml of saturated NaHCO₃ solution and 10 ml of saturated aqueous NaCl. The organic phase is dried over anhydrous magnesium sulfate, filtered and then evaporated to dryness. 120 mg of a yellow oil are obtained, which product is chromatographed on a silica cartridge (7 g, eluent: 90/10 CH₂Cl₂/EtOAc). 78 mg of expected product 38 are collected (yield=75%).

$^1$H NMR (400 MHz, DMSO-d$_6$), a 50/50 mixture of 2 isomers, with δ (ppm): 0.99 (s, 9H); 1.25 (s, 1.5H); 1.26 (1.5H); 1.31 (s, 1.5H); 1.32 (1.5H); from 2.57 to 2.78 (m, 4H); from 3.21 to 3.33 (partially masked m, 1H); 3.28 (s, 1.5H); 3.30 (s, 1.5H); from 3.64 to 3.73 (m, 1H); 3.79 (d, J=8.5 Hz, 0.5H); 3.84 (d, J=8.5 Hz, 0.5H); 3.94 (m, 1H); from 3.97 to 4.07 (m, 1H); from 4.26 to 4.36 (m, 2H); 4.44 (d, J=8.0 Hz, 0.5H); 4.55 (d, J=8.0 Hz, 0.5H); 4.90 (m, 1H); 5.14 (m, 1H); 5.47 (m, 1H); 5.69 (d, J=15.5 Hz, 1H); 7.47 (s, 1H); 7.48 (s, 1H); 8.00 (d, J=7.0 Hz, 0.5H); 8.04 (d, J=7.0 Hz, 0.5H).

e) Step 4: Preparation of N-(4-(2,6-dichloropyrid-4-ylmethyl)-5-oxoperhydro-1,4-thiazepin-6-yl)-(E)-(2R,3R,4S,5R)-3,4,5-trihydroxy-2-methoxy-8,8-dimethylnon-6-enamide (Example 14)

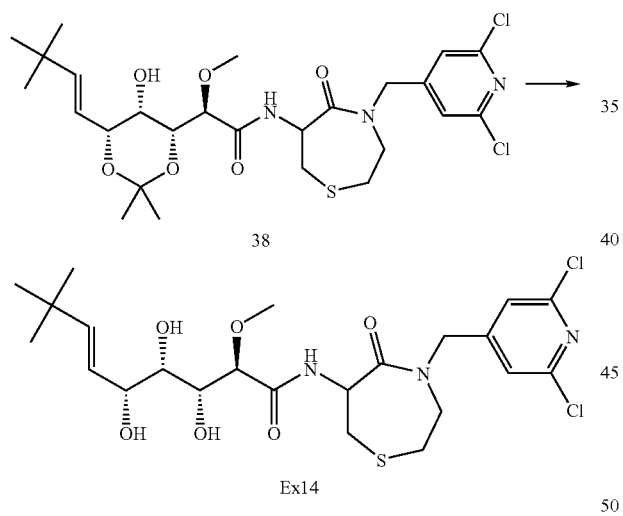

57 mg of 38 (97 µmol) are mixed with 0.52 ml of THF and 1 ml of 1N hydrochloric acid, with stirring and under argon. Stirring is continued for 4 hours at room temperature. The solution is then cooled to 0° C., and is neutralized to pH 7.0 with 1N sodium hydroxide. The mixture is extracted twice with 2 ml of EtOAc. The organic phases are combined, dried over magnesium sulfate and filtered, and then evaporated to dryness. 46 mg of product Example 14 are obtained (yield=85%).

ES: 550 (+)=(M+H)(+); 532(+)=(M+H)(+) —H₂O $^1$H NMR (400 MHz, DMSO-d$_6$), a 60/40 mixture of 2 isomers, with δ (ppm): 1.03 (s, 5.4H); 1.04 (s, 3.6H); from 2.57 to 2.70 (m, 2H); 2.75 (m, 1H); 2.86 (dd, J=3.0 and 14.5 Hz, 0.6H); 2.93 (dd, J=3.0 and 14.5 Hz, 0.4H); 3.58 (s, 3H); from 3.59 to 3.66 (m, 2H); 3.81 (m, 1H); 3.85 (m, 1H); 3.99 (m, 1H); from 4.21 to 4.29 (m, 2H); from 4.91 to 5.00 (m, 1H); 5.15 (m, 1H); 5.44 (m, 1H); 5.83 (d, J=15.5 Hz, 0.6H); 5.84 (d, J=15.5 Hz, 0.4H); 7.14 (s, 1.2H); 7.16 (s, 0.8H); 8.17 (d, J=7.0 Hz, 0.6H); 8.20 (d, J=7.0 Hz, 0.4H).

EXAMPLE 15

N-(4-(4-butoxybenzyl)-5-oxoperhydro-1,4-thiazepin-6-yl)-(E)-(2R,3R,4S,5R)-3,4,5-trihydroxy-2-methoxy-8,8-dimethylnon-6-enamide

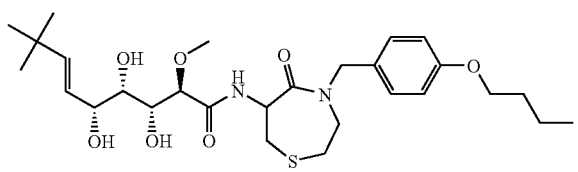

a) Step 1: Preparation of tert-butyl [4-(4-butoxybenzyl)-5-oxoperhydro-1,4-thiazepin-6-yl]carbamate (39)

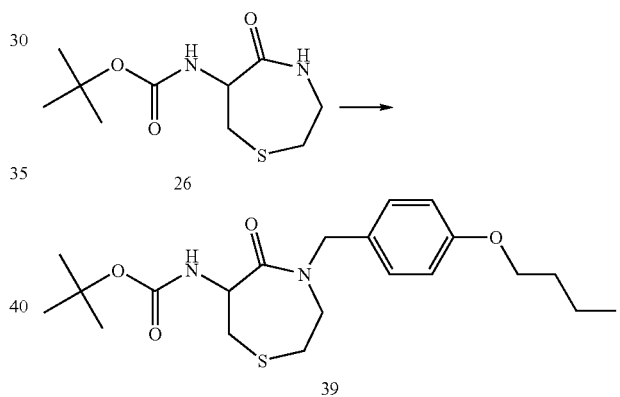

81 mg of sodium hydride as a 60% suspension in oil (2.03 mmol) are introduced at room temperature into a 25 ml round-bottomed flask, with stirring and under an argon atmosphere, containing 20 ml of THF and 500 mg of 26 (2.03 mmol). The medium is stirred for 1 hour and 1.1 g (2.34 mmol) of 4-butoxybenzyl bromide are then added. The medium is stirred for 16 hours, 20 ml of EtOAc and 20 ml of water are added to the reaction medium and, after separation of the phases by settling, the organic phase is washed with 10 ml of water. The organic phase is dried, filtered and then evaporated to dryness to give 1.3 g of crude product, which product is chromatographed on a silica cartridge (25 g) with a 90/10 heptane/EtOAc mixture. 420 mg of product 39 are recovered (yield=53%).

$^1$H NMR (400 MHz, DMSO-d$_6$), δ(ppm): 0.92 (t, J=7.5 Hz, 3H) 1.39 (s, 9H); 1.42 (m, 2H); 1.67 (m, 2H); 2.39 (m, 1H); from 2.51 to 2.71 (m, 3H); 3.60 (m, 1H); 3.74 (m, 1H); 3.94 (t, J=6.5 Hz, 2H); 4.33 (d, J=14.5 Hz, 1H); 4.59 (d, J=14.5 Hz, 1H); 4.72 (broad m, 1H); 6.73 (broad d, J=7.5 Hz, 1H); 6.89 (d, J=8.5 Hz, 2H); 7.19 (d, J=8.5 Hz, 2H).

b) Step 2: Preparation of 6-amino-4-(4-butoxyben-zyl)-perhydro-1,4-thiazepin-5-one hydrochloride (40)

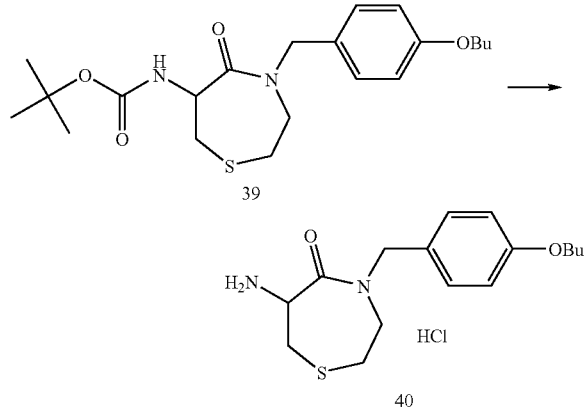

260 mg of 39 (0.64 mmol) are taken up in a 25 ml round-bottomed flask and 4 ml of a solution of hydrogen chloride in dioxane (4M) are added. The mixture is stirred for 4 hours at room temperature under argon. After evaporating off the solvent, 280 mg of amine 40 are obtained in hydrochloride form, which product is used directly in the following step.

$^1$H NMR (400 MHz, DMSO-d$_6$), δ(ppm): 0.92 (t, J=7.5 Hz, 3H) 1.42 (m, 2H); 1.67 (m, 2H); from 2.46 to 2.55 (partially masked m, 1H); from 2.61 to 2.75 (m, 2H); 2.83 (m, 1H); 3.65 (partially masked m, 1H); 3.79 (m, 1H); 3.94 (t, J=6.5 Hz, 2H); 4.30 (d, J=14.5 Hz, 1H); 4.68 (partially masked m, 1H); 4.71 (d, J=14.5 Hz, 1H); 6.89 (d, J=8.5 Hz, 2H); 7.22 (d, J=8.5 Hz, 2H); 8.25 (broad m, 3H).

c) Step 3: Preparation of (R)—N-(4-(4-butoxyben-zyl)-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (41)

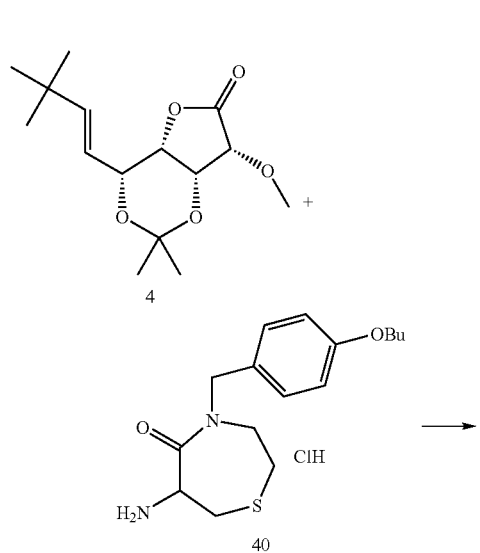

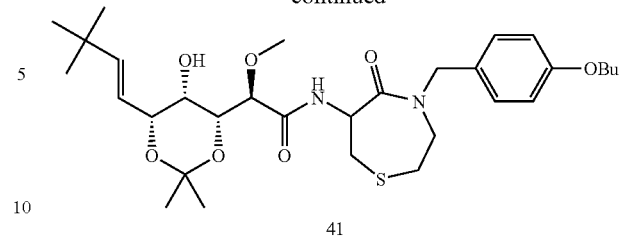

50 mg of 4 (176 μmol), 121 mg of 40 (351 μmol), 73 mg of sodium 2-ethylhexanoate (440 μmol) and 1 ml of THF are successively introduced into a Wheaton tube, with stirring and under an argon atmosphere. Stirring is continued at room temperature for 3 days. 2 ml of ethyl acetate are added to the reaction medium. The mixture is washed successively with 1 ml of HCl solution (1N) and then with 1 ml of saturated NaHCO$_3$ solution and 1 ml of water. The organic phase is dried over anhydrous magnesium sulfate, filtered and then evaporated to dryness. 135 mg of a colorless resin are obtained, which product is chromatographed on a silica cartridge (5 g, eluent: 50/50 heptane/EtOAc). 97 mg of expected product 41 are collected (yield=95%).

$^1$H NMR (400 MHz, DMSO-d$_6$), a 50/50 mixture of 2 isomers, with δ(ppm): 0.92 (t, J=7.5 Hz, 3H); 0.99 (s, 9H); 1.28 (s, 3H); 1.33 (s, 3H); 1.42 (m, 2H); 1.68 (m, 2H); 2.42 (m, 1H); from 2.52 to 2.72 (m, 3H); 3.27 (partially masked m, 1H); 3.29 (s, 3H); 3.64 (partially masked m, 1H); from 3.77 to 3.86 (m, 2H); 3.93 (t, J=6.5 Hz, 2H); 3.95 (partially masked m, 1H); 4.29 (m, 1H); 4.36 (m, 1H); 4.45 (d, J=8.0 Hz, 0.5H); 4.57 (d, J=8.0 Hz, 0.5H); 4.63 (m, 1H); 5.01 (m, 1H); 5.45 (dd, J=7.0 and 16.0 Hz, 1H); 5.69 (d, J=16.0 Hz, 1H); 6.89 (d, J=8.5 Hz, 2H); 7.20 (d, J=8.5 Hz, 2H); 8.02 (d, J=6.5 Hz, 0.5H); 8.07 (d, J=6.5 Hz, 0.5H).

e) Step 4: Preparation of N-(4-(4-butoxybenzyl)-5-oxo-perhydro-1,4-thiazepin-6-yl)-(E)-(2R,3R,4S,5R)-3,4,5-trihydroxy-2-methoxy-8,8-dimethylnon-6-enamide (Example 15)

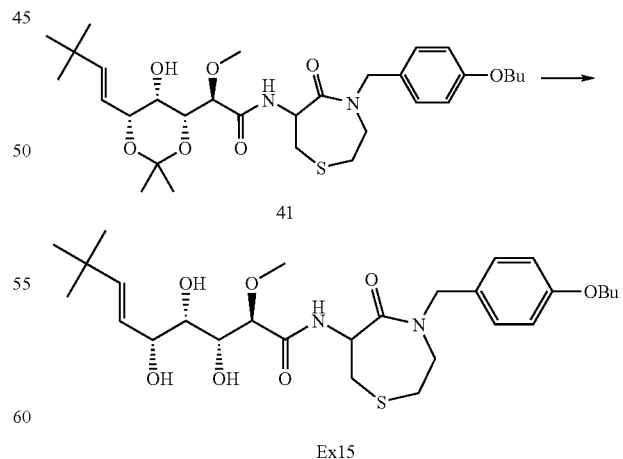

97 mg of 41 (164 μmol) are mixed with 0.82 ml of THF and 1.6 ml of 1N hydrochloric acid, with stirring and under argon. Stirring is continued for 5 hours at room temperature. The solution is then cooled to 0° C. and neutralized to pH 7.0 with 1N sodium hydroxide. The mixture is extracted twice with 3 ml of EtOAc. The organic phases are combined, dried over magnesium sulfate and filtered, and then evaporated to dryness. 71 mg of product are obtained, which product is purified on a preparative silica plate (eluent: 90/10 $CH_2Cl_2$/MeOH) to give 13 mg of expected product Example 15 (yield=14%).

ES: 570(+)=(M+H)(+); 553(+)=(M+H)(+) —$H_2O$ $^1$H NMR (500 MHz, DMSO-$d_6$), a 60/40 mixture of 2 isomers, with δ (ppm): 0.90 (t, J=7.5 Hz, 3H); 0.98 (s, 9H); 1.42 (m, 2H); 1.68 (m, 2H); 2.38 (m, 1H); from 2.54 to 2.65 (m, 2H); 2.71 (m, 1H); 3.27 (s, 1.2H); 3.28 (s, 1.8H); 3.34 (partially masked m, 1H); from 3.55 to 3.71 (m, 2H); 3.74 (m, 1H); 3.80 (m, 1H); 3.94 (t, J=7.0 Hz, 2H); 3.98 (m, 1H); from 4.35 to 4.43 (m, 2H); 4.53 (d, J=7.5 Hz, 0.4H); from 4.58 to 4.53 (m, 2.6H); 4.99 (m, 1H); 5.34 (m, 1H); 5.64 (d, J=15.5 Hz, 1H); 6.88 (broad d, J=8.5 Hz, 2H); 7.20 (broad d, J=8.5 Hz, 2H); 8.05 (d, J=6.5 Hz, 0.4H); 8.07 (d, J=6.5 Hz, 0.6H).

EXAMPLE 16

N-(4-(naphthalen-2-ylmethyl)-5-oxoperhydro-1,4-thiazepin-6-yl)-(E)-(2R,3R,4S,5R)-3,4,5-trihydroxy-2-methoxy-8,8-dimethylnon-6-enamide

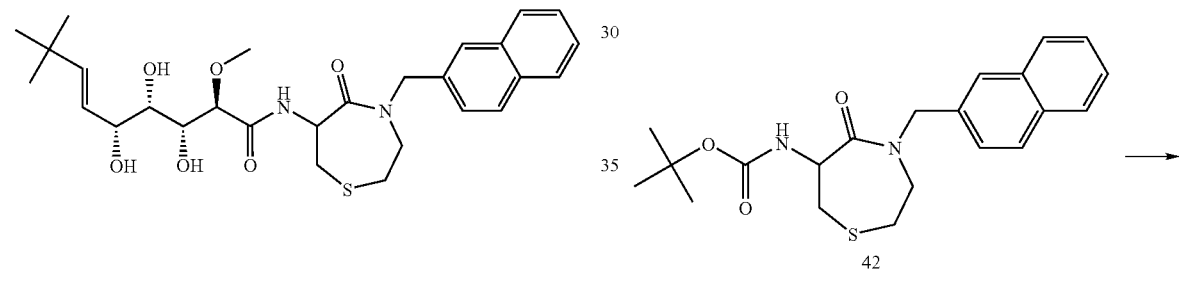

a) Step 1: Preparation of tert-butyl [4-(naphthalen-2-ylmethyl)-5-oxoperhydro-1,4-thiazepin-6-yl]carbamate (42)

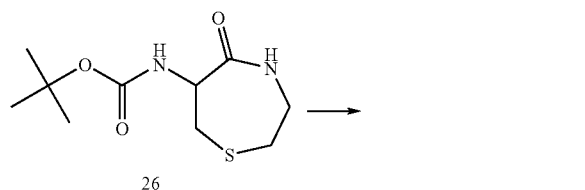

81 mg of sodium hydride as a 60% suspension in oil (2.03 μmol) are introduced at room temperature into a 25 ml round-bottomed flask, with stirring and under an argon atmosphere, containing 20 ml of THF and 500 mg of 26 (2.03 mmol). The medium is stirred for 1 hour and 449 mg (2.03 mmol) of 2-(bromomethyl)naphthalene are then added. The medium is stirred for 16 hours, 20 ml of EtOAc and 20 ml of water are added to the reaction medium and, after separation of the phases by settling, the organic phase is washed with 10 ml of water. The organic phase is dried, filtered and then evaporated to dryness to give 1.5 g of crude product, which product is chromatographed on a silica cartridge (25 g) with a 90/10 heptane/EtOAc mixture. 510 mg of product 42 are recovered (yield=65%).

$^1$H NMR (300 MHz, DMSO-$d_6$): δ(ppm): 1.40 (s, 9H); from 2.40 to 2.75 (partially masked m, 4H); 3.68 (m, 1H); 3.84 (m, 1H); 4.54 (d, J=14.5 Hz, 1H); 4.80 (m, 1H); 4.91 (d, J=14.5 Hz, 1H); 6.71 (d, J=7.0 Hz, 1H); 7.41 (d, J=8.5 Hz, 1H); from 7.45 to 7.55 (m, 2H); 7.80 (s, 1H); from 7.83 to 7.93 (m, 3H).

b) Step 2: Preparation of 6-amino-4-(naphthalen-2-yl-methyl)perhydro-1,4-thiazepin-5-one hydrochloride (43)

510 mg of 42 (1.32 mmol) are taken up in a 25 ml round-bottomed flask and 10 ml of a solution of hydrogen chloride in dioxane (4M) are added. The mixture is stirred for 3 hours at room temperature under argon. After evaporating off the solvent, 510 mg of amine 43 are obtained in hydrochloride form, which product is used directly in the following step.

$^1$H NMR (400 MHz, DMSO-$d_6$), δ(ppm): from 2.53 to 2.70 (m, 2H); 2.79 (dd, J=8.5 and 14.5 Hz, 1H); 3.00 (dd, J=3.5 and 14.5 Hz, 1H); 3.73 (m, 1H); 3.90 (m, 1H); 4.52 (d, J=15.0 Hz, 1H); 4.78 (dd, J=3.5 and 8.5 Hz, 1H); 5.00 (d, J=15.0 Hz, 1H); 7.45 (dd, J=2.0 and 7.5 Hz, 1H); from 7.45 to 7.55 (m, 2H); 7.84 (s, 1H); from 7.85 to 7.92 (m, 3H); 8.62 (broad s, 3H).

c) Step 3: Preparation of (R)—N-(4-(naphthalen-2-ylmethyl)-5-oxoperhydro-1,4-thiazepin-6-yl)-2-[(4R,5S,6R)-6-((E)-3,3-dimethylbut-1-enyl)-5-hydroxy-2,2-dimethyl-1,3-dioxinan-4-yl]-2-methoxyacetamide (44)

e) Step 4: Preparation of N-(4-(naphthalen-2-ylmethyl)-5-oxoperhydro-1,4-thiazepin-6-yl)-(E)-(2R,3R,4S,5R)-3,4,5-trihydroxy-2-methoxy-8,8-dimethylnon-6-enamide Example 16

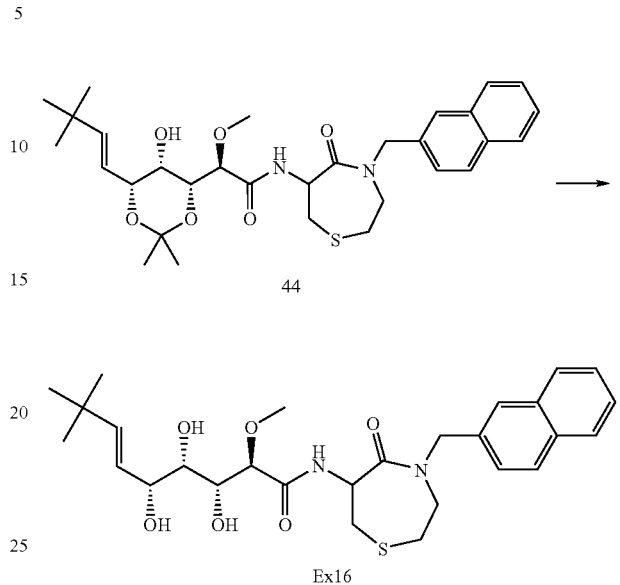

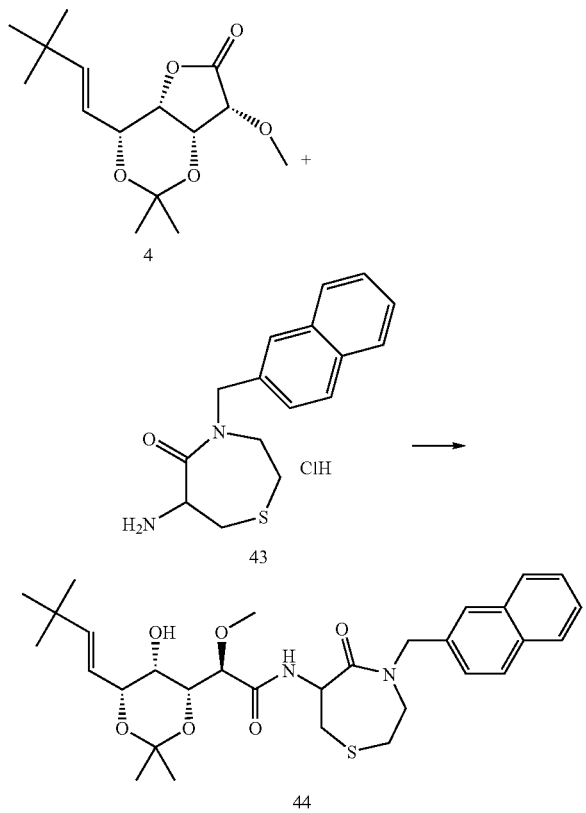

40 mg of 44 (70 μmol) are mixed with 0.38 ml of THF and 0.75 ml of 1N hydrochloric acid, with stirring and under argon. Stirring is continued for 5 hours at room temperature. The solution is then cooled to 0° C. and neutralized to pH 7.0 with 1N sodium hydroxide. The mixture is extracted twice with 2 ml of EtOAc. The organic phases are combined, dried over magnesium sulfate and filtered and then evaporated to dryness. 25 mg of expected product Example 16 are obtained (yield=67%).

ES: 531(+)=(M+H)(+); 513(+)=(M+H)(+) —H$_2$O $^1$H NMR (400 MHz, DMSO-d$_6$), a 50/50 mixture of 2 isomers, with δ (ppm): 0.98 (s, 9H); from 2.42 to 2.61 (partially masked m, 2H); from 2.65 to 2.79 (m, 2H); 3.29 (s, 1.5H); 3.30 (s, 1.5H); from 3.30 to 3.40 (partially masked m, 1H); 3.61 (m, 1H); from 3.68 to 3.71 (m, 2H); 3.90 (m, 1H); 3.99 (m, 1H); 4.39 (d, J=5.5 Hz, 1H); 4.52 (d, J=7.5 Hz, 0.5H); from 4.56 to 4.63 (m, 2.5H); 4.90 (d, J=16.0 Hz, 1H); 5.07 (m, 1H); 5.35 (broad dd, J=7.0 and 16.0 Hz, 1H); 5.65 (broad d, J=16.0 Hz, 1H); 7.41 (d, J=8.5 Hz, 1H); 7.50 (partially masked m, 2H); 7.82 (broad s, 1H); from 7.85 to 7.92 (m, 3H); 8.08 (d, J=6.5 Hz, 0.5H); 8.12 (d, J=6.5 Hz, 0.5H).

50 mg of 4 (176 μmol), 114 mg of 43 (352 μmol), 73 mg of sodium 2-ethylhexanoate (440 μmol) and 1 ml of THF are successively introduced into a Wheaton tube, with stirring and under an argon atmosphere. Stirring is continued at room temperature for 24 hours. 3 ml of ethyl acetate are added to the reaction medium. The mixture is washed successively with 3 ml of HCl solution (1N) and then with 3 ml of saturated NaHCO$_3$ solution and 3 ml of saturated NaCl solution. The organic phase is dried over anhydrous magnesium sulfate, filtered and then evaporated to dryness. 140 mg of an oil are obtained, which product is chromatographed on a cartridge of NH$_2$-grafted silica (11 g, eluent: 50/50 heptane/EtOAc). 40 mg of expected product 44 are collected (yield=44%).

$^1$H NMR (400 MHz, CDCl$_3$), a 60/40 mixture of 2 isomers, with δ(ppm): 1.04 (s, 9H); 1.48 (s, 3H); 1.51 (s, 3H); from 2.38 to 2.51 (m, 2H); from 2.66 to 2.92 (m, 2.6H); from 3.47 to 3.61 (partially masked m, 1.4H); 3.53 (s, 1.8H); 3.56 (s, 1.2H); from 3.62 to 3.77 (m, 1H); from 3.88 to 3.97 (m, 2H); 4.11 (broad d, J=6.5 Hz, 1H); 4.29 (m, 1H); 4.67 (d, J=15.5 Hz, 0.4H); 4.72 (d, J=15.5 Hz, 0.6H); 4.93 (d, J=15.5 Hz, 0.6H); 4.97 (d, J=15.5 Hz, 0.4H); 5.15 (m, 1H); 5.54 (dd, J=6.5 and 16.0 Hz, 0.4H); 5.58 (dd, J=6.5 and 16.0 Hz, 0.6H); 5.79 (d, J=16.0 Hz, 1H); 7.37 (m, 1H); from 7.43 to 7.59 (m, 2H); from 7.64 to 7.72 (m, 2H); from 7.78 to 7.89 (m, 3.6H); 8.10 (d, J=7.0 Hz, 0.4H).

EXAMPLE 17

N-(4-(naphthalen-2-ylmethyl)-5-oxoperhydro-1,4-thiazepin-6-yl)-(E)-(2R,3R,4S,5R)-3,4,5-trihydroxy-2-methoxy-8,8-dimethylnon-6-enamide

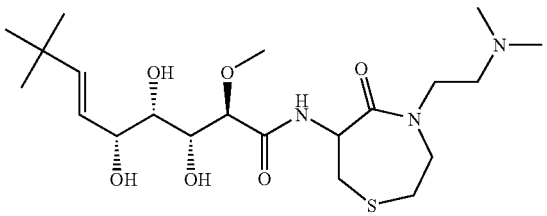

a) Step 1: Preparation of tert-butyl [4-(2-dimethyl-aminoethyl)-5-oxoperhydro-1,4-thiazepin-6-yl]carbamate (45)

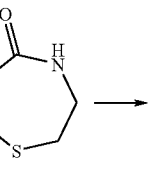

26

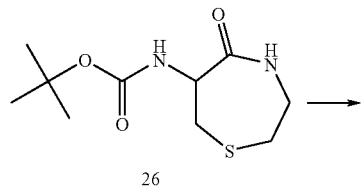

45

53 mg of sodium hydride as a 60% suspension in oil (1.3 mmol) are introduced at 0° C. into a 25 ml round-bottomed flask, with stirring and under an argon atmosphere, containing 5 ml of DMF and 123 mg of 26 (0.5 mmol). The medium is allowed to return to room temperature over 1 hour, and a solution of DMF (2 ml) containing 128 mg (0.55 mmol) of 2-bromoethyldimethylamine hydrobromide and 165 mg of NaI (1.1 mmol) is then added. The medium is stirred for 1.5 hours, 20 ml of EtOAc and 20 ml of water are added to the reaction medium and, after separation of the phases by settling, the organic phase is washed 3 times with 20 ml of water, once with 20 ml of HCl (1N) and finally once with 20 ml of aqueous ammonia. The organic phase is then dried, filtered and evaporated to dryness to give 82 mg of product 45 (yield=52%).

b) Step 2: Preparation of 6-amino-4-(2-dimethylamino-ethyl)perhydro-1,4-thiazepin-5-one dihydrochloride (46)

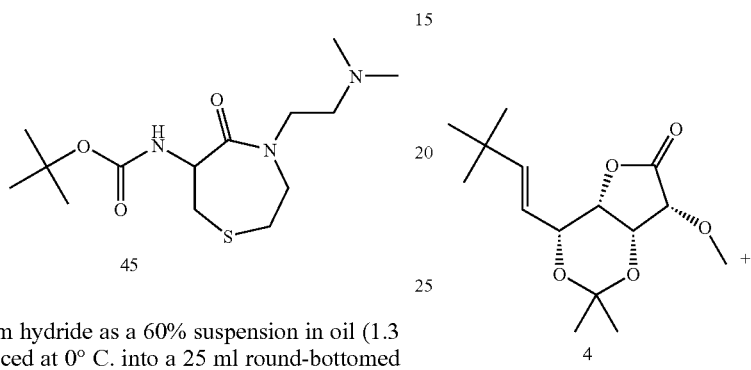

114 mg of 45 (0.359 mmol) are placed in a 20 ml round-bottomed flask and 4 ml of a solution of hydrogen chloride in dioxane (4M) are added. The mixture is stirred for 3 hours at room temperature under argon. After evaporating off the solvent, 113 mg of amine 46 are obtained in dihydrochloride form, which product is used directly in the following step.

c) Step 3: Preparation of (R)—N-(4-(2-dimethylaminoethyl)-5-oxoperhydro-1,4-thiazepin-6-yl)-2-[(4R, 5S,6R)-6-((E)-3,3-dimethylbut-1-enyl)-5-hydroxy-2,2-dimethyl-1,3-dioxinan-4-yl]-2-methoxyacetamide (47)

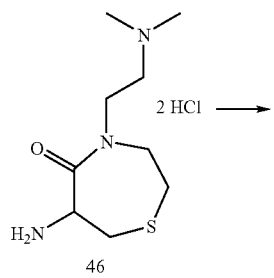

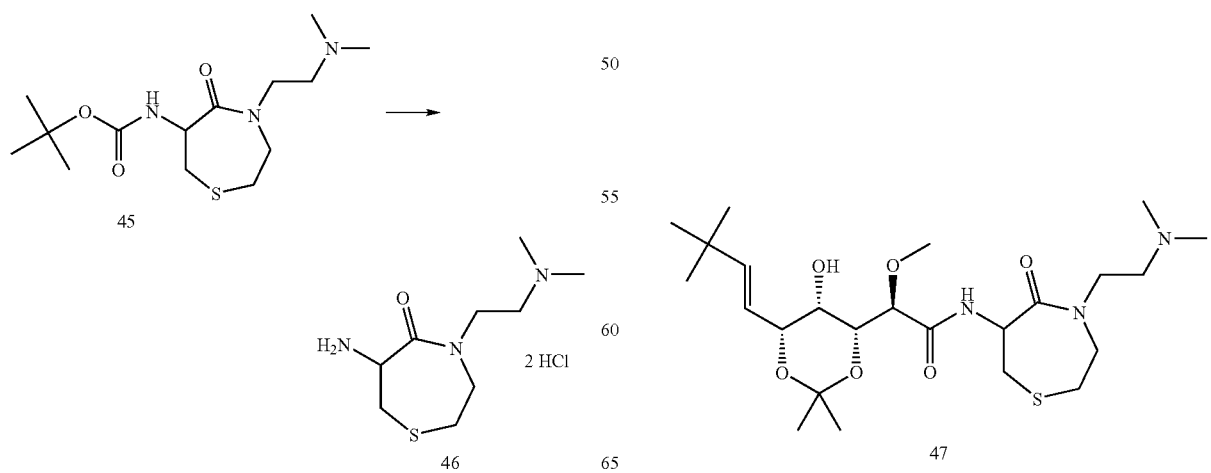

45 mg of 4 (158 µmol), 50 mg of 46 (198 µmol), 66 mg of sodium 2-ethylhexanoate (396 µmol) and 2.5 ml of THF are successively introduced into a 20 ml round-bottomed flask with stirring and under an argon atmosphere. Stirring is continued at room temperature for 6 days. 10 ml of EtOAc are added. The organic phase is successively washed with 10 ml of 0.1M sodium hydroxide solution, 10 ml of saturated NaCl solution and 10 ml of saturated NH₄Cl solution. The organic phase is dried over MgSO₄, filtered and evaporated. 31.3 mg of a viscous yellow oil 47 are collected (yield=40%).

TLC (97/3 CH$_2$Cl$_2$/MeOH): Rf=0.4 LCMS (ES+/−, 50 V): m/z=1005$^+$ (2M+H); 503$^+$ (M+H); 445$^+$ (M+H−CO(CH$_3$)$_2$); 1049$^−$ (2M−H+HCOOH); 547$^−$ (M−H+HCOOH); 501$^−$ (M−H).

d) Step 4: Preparation of N-(4-(2-dimethylaminoethyl)-5-oxoperhydro-1,4-thiazepin-6-yl)-(E)-(2R,3R, 4S,5R)-3,4,5-trihydroxy-2-methoxy-8,8-dimethyl-non-6-enamide (Example 17)

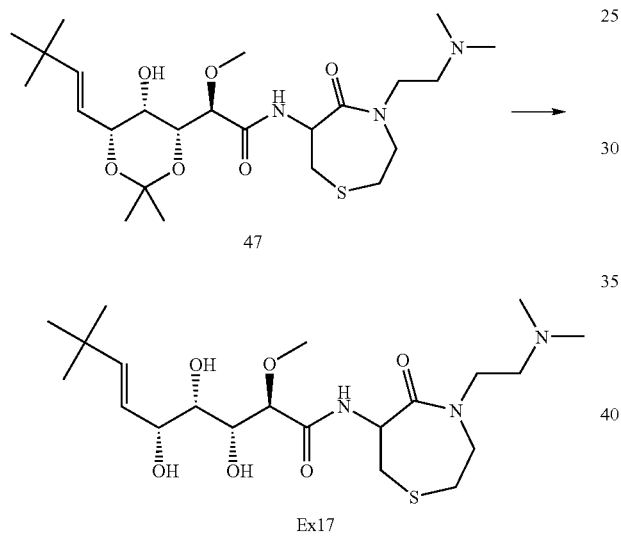

31 mg of 47 (62 µmol) are dissolved in 0.6 ml of THF in a 50 ml round-bottomed flask and the medium is cooled to 0° C. 0.4 ml of water at 0° C. are then added, followed by addition of 0.6 ml of TFA at 0° C. The flask is maintained at 0° C. for 2 hours with stirring. The solvents are evaporated off under high vacuum at 0° C. 5 ml of methanol cooled to 0° C. are added and the mixture is then evaporated to dryness. 35 mg of an amorphous solid are collected, which product is chromatographed on silica with 80/20 CH$_2$Cl$_2$/EtOAc. 20 mg of expected product Example 17 are recovered (yield=70%).

TLC (80/20 CH$_2$Cl$_2$/MeOH): Rf=0.58 LCMS (ES+/−50 V): m/z=925$^+$ (2M+H); 463$^+$ (M+H); 445$^+$ (M+H−H$_2$O); 427$^+$ (M+H−2H$_2$O); 409$^+$ (M+H−3H$_2$O); 969$^−$ (2M−H+HCOOH); 507$^−$ (M−H+HCOOH); 461$^−$ (M−H). $^1$H NMR (400 MHz, DMSO-d$_6$): δ(ppm)=7.98 (dd, 1H); 5.65 (d, 1H); 5.35 (dd, 1H); 4.92 (m, 1H); 4.5 (d, 2H); 4.33 (m, 1H); 3.98 (m, 1H); 3.71 (d, 1H); 3.58 (m, 1H); 3.33 (m, 1H); 3.25 (s, 3H); 2.4-2.8 (m, 4H); 2.20 (broad s, 6H); 1.0-1.4 (m, 6H); 0.97 (s, 9H).

EXAMPLE 18 benzyl 5-oxo-6-((E)-(2R,3R,4S,5R)-3,4,5-tri-hydroxy-2-methoxy-8,8-dimethylnon-6-enoylamino)perhydro-1,4-diazepine-1-carboxylate

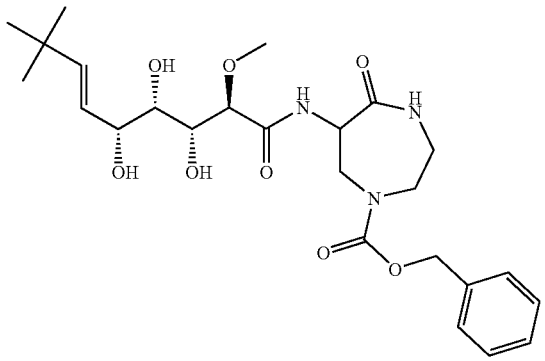

a) Step 1: Preparation of benzyl 6-{(R)-2-[(4R,5S, 6R)-6-((E)-3,3-dimethylbut-1-enyl)-5-hydroxy-2,2-dimethyl-1,3-dioxinan-4-yl]-2-methoxyacetylamino}-5-oxoperhydro-1,4-diazepine-1-carboxylate (49)

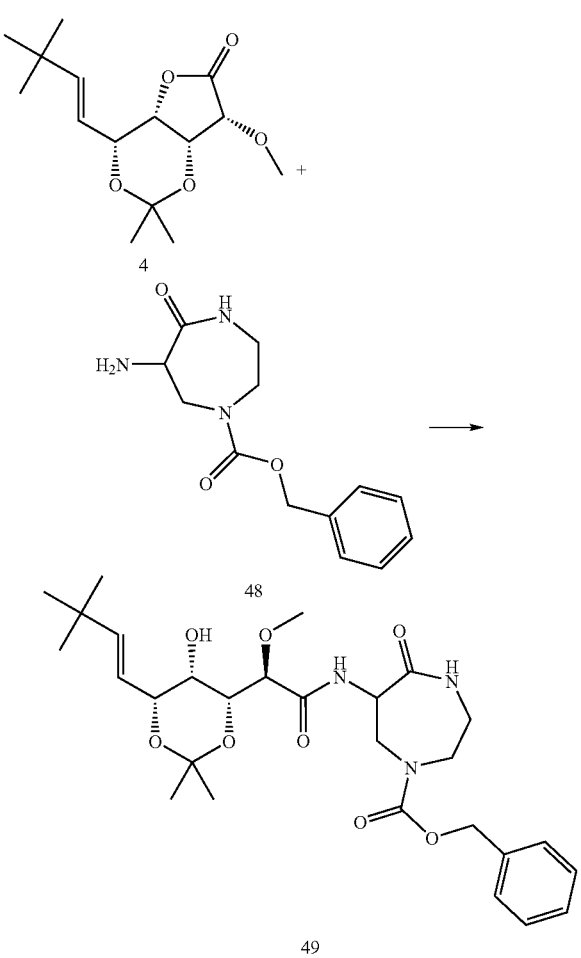

100 mg of 4 (352 µmol), 370 mg of benzyl 6-amino-5-oxo-[1,4]diazepane-1-carboxylate 48 (1.4 mmol) (sold by AstraTech. Inc), 292 mg of sodium 2-ethylhexanoate (1.76 mmol) and 2.5 ml of THF are successively introduced into a Wheaton tube, with stirring and under an argon atmosphere. Stirring is continued at room temperature for 6 days. 5 ml of ethyl acetate are added to the reaction medium. The mixture is washed successively with 5 ml of HCl solution (1N) and then with 5 ml of saturated NaHCO$_3$ solution and 5 ml of water. The organic phase is dried over anhydrous magnesium sulfate, filtered and then evaporated to dryness. 190 mg of an oil are obtained, which oil is chromatographed on a cartridge of NH$_2$-grafted silica (7 g, eluent: 40/60 heptane/EtOAc). 81 mg of expected product 49 are collected (yield=42%).

$^1$H NMR (300 MHz DMSO-d6), a 60/40 mixture of 2 isomers, with δ (ppm): 0.99 (s, 9H); from 1.15 to 1.39 (broad m, 6H); 2.99 (broad m, 2H); from 3.10 to 3.55 (partially masked m, 3H); 3.27 (s, 1.8H); 3.28 (s, 1.2H); 3.79 (d, J=11.5 Hz, 0.4H); 3.82 (d, J=11.5 Hz, 0.6H); from 3.90 to 4.15 (m, 3H); 4.27 (m, 1H); from 4.36 to 4.60 (m, 2H); from 5.03 to 5.14 (m, 2H); 5.45 (m, 1H); 5.69 (d, J=16.0 Hz, 1H); from 7.25 to 7.44 (m, 5H); 7.82 (broad m, 0.6H); 7.91 (d, J=7.0 Hz, 0.4H); 8.08 (broad m, 1H)

b) Step 2: Preparation of benzyl 5-oxo-6-((E)-(2R, 3R,4S,5R)-3,4,5-trihydroxy-2-methoxy-8,8-dimethylnon-6-enoylamino)perhydro-1,4-diazepine-1-carboxylate (Example 18)

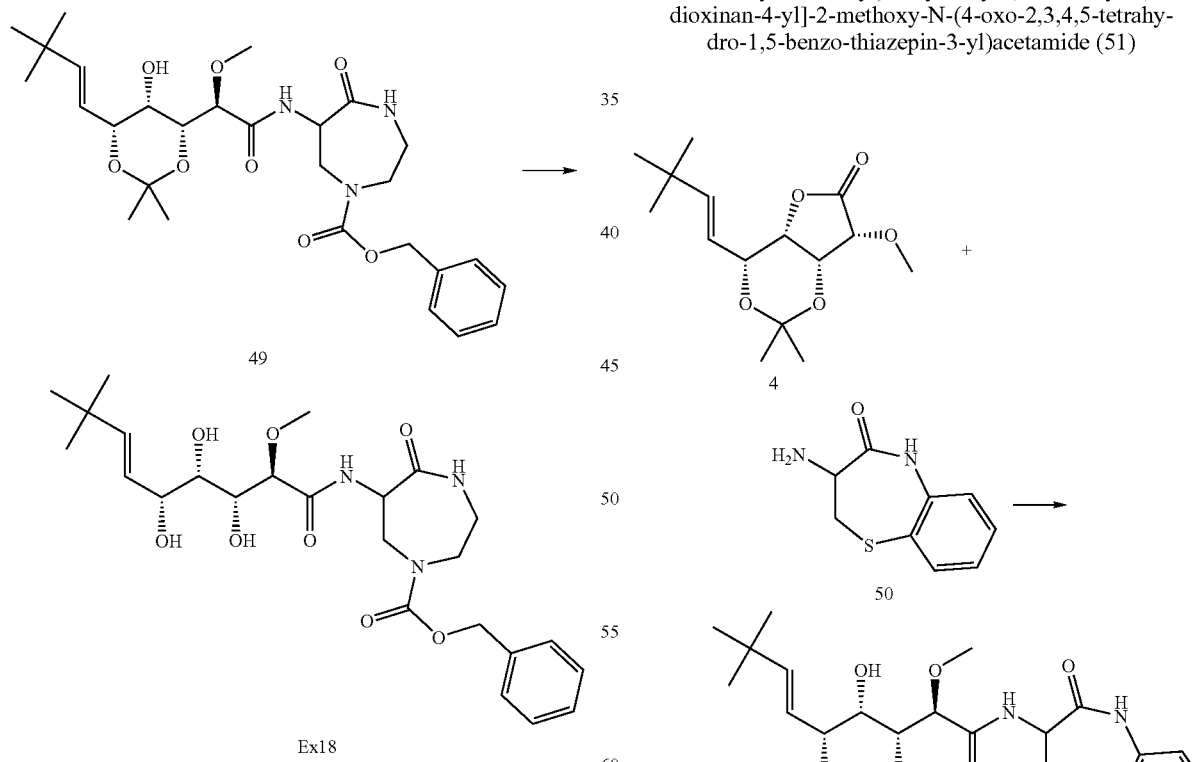

49

Ex18

81 mg of 49 (148 µmol) are mixed with 0.75 ml of THF and 1.5 ml of 1N hydrochloric acid (750 µmol), with stirring and under argon. Stirring is continued for 5 hours at room temperature. The solution is then cooled to 0° C. and neutralized to pH 7.0 with 1N sodium hydroxide. The mixture is extracted twice with 2 ml of EtOAc. The organic phases are combined, dried over magnesium sulfate and filtered, and then evaporated to dryness. 49 mg of expected product Example 18 are obtained (yield=66%).

ES: 508(+)=(M+H)(+); 490(+)=(M+H)(+) —H$_2$O $^1$H NMR (400 MHz, CDCl3), δ (ppm): 1.03 (s, 9H); 3.01 (broad m, 2H); from 3.24 to 3.72 (broad m, 5H); 3.56 (s, 3H); from 3.75 to 3.87 (m, 2H); 4.23 (broad m, 1H); from 4.27 to 4.53 (broad m, 2H); 4.63 (broad m, 1H); from 5.09 to 5.26 (broad m, 2H); 5.43 (m, 1H); 5.84 (d, J=16.0 Hz, 1H); 6.16 (broad m, 1H); from 7.29 to 7.49 (m, 5H); 7.93 (broad m, 1H).

EXAMPLE 19

N-(4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide

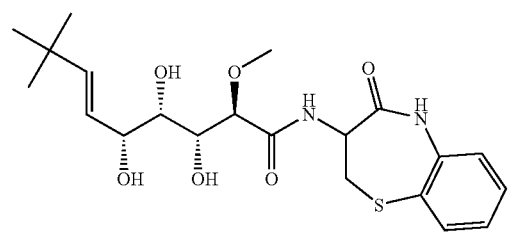

a) Step 1: Preparation of (R)-2-[(4R,5S,6R)-6-((E)-3,3-dimethylbut-1-enyl)-5-hydroxy-2,2-dimethyl-1,3-dioxinan-4-yl]-2-methoxy-N-(4-oxo-2,3,4,5-tetrahydro-1,5-benzo-thiazepin-3-yl)acetamide (51)

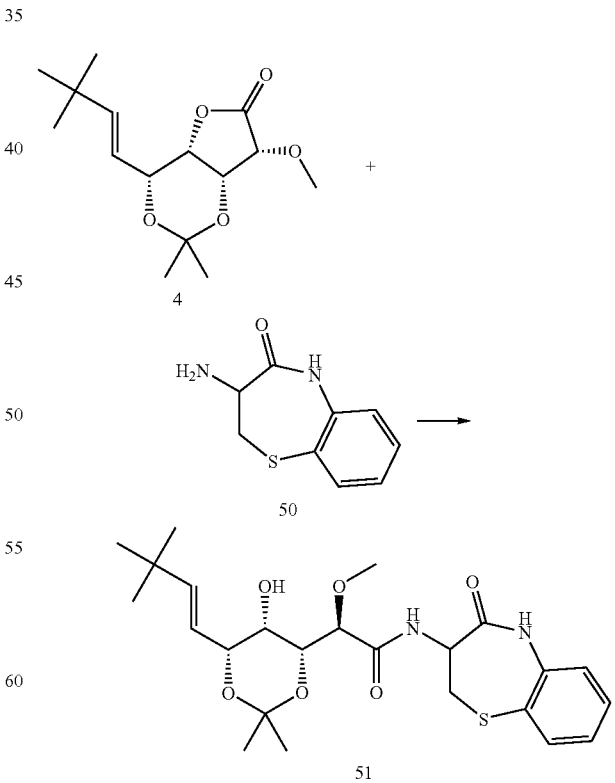

4

50

51

50 mg of 4 (176 µmol), 68 mg of 3-amino-2,3-dihydro-5H-1,5-benzothiazepin-4-one 50 (0.35 mmol) (sold by Interchim), 73 mg of sodium 2-ethylhexanoate (0.44 mmol) and 1 ml of THF are successively introduced into a Wheaton tube, with stirring and under an argon atmosphere. Stirring is continued at room temperature for 2 days. 3 ml of ethyl acetate are added to the reaction medium. The mixture is washed with 3 ml of HCl solution (1N) and insoluble matter in gel form is formed, which matter, after filtering through a sinter funnel, gives 78 mg of expected product 51 (yield=93%, white solid).

$^1$H NMR (400 MHz DMSO-d6), δ (ppm): 0.98 (s, 9H); 1.22 (s, 3H); 1.28 (s, 3H); 3.12 (m, 1H); 3.23 (broad s, 4H); 3.52 (partially masked m, 1H); 3.78 (d, J=8.5 Hz, 1H); 3.89 (broad d, J=8.5 Hz, 1H); 4.25 (broad d, J=7.0 Hz, 1H); 4.41 (m, 1H); 5.43 (dd, J=7.0 and 16.0 Hz, 1H); 5.67 (d, J=16.0 Hz, 1H); 7.17 (dd, J=1.5 and 8.0 Hz, 1H); 7.21 (dt, J=1.5 and 8.0 Hz, 1H); 7.46 (dt, J=1.5 and 7.5 Hz, 1H); 7.61 (dd, J=1.5 and 8.0 Hz, 1H); 8.36 (d, J=8.5 Hz, 1H); 10.15 (s, 1H).

b) Step 2: Preparation of N-(4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide (Example 19)

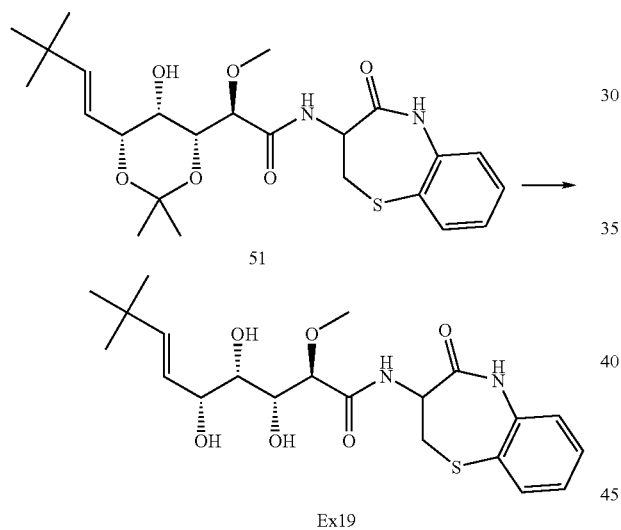

78 mg of 51 (163 µmol) are mixed with 0.8 ml of THF and 1.6 ml of 1N hydrochloric acid (1.6 mmol), with stirring and under argon. Stirring is continued for 5 hours at room temperature. The solution is then cooled to 0° C. and neutralized to pH 7.0 with 1N sodium hydroxide. The mixture is extracted twice with 5 ml of EtOAc. The organic phases are combined, dried over magnesium sulfate and filtered, and then evaporated to dryness. 19.5 mg of expected product Example 19 are obtained (yield=27%).

ES: 439(+)=(N+H)(+); 421(+)=(N+H)(+)—H$_2$O $^1$H NMR (400 MHz DMSO-d6), δ (ppm): 0.95 (s, 9H); 3.14 (m, 1H); 3.20 (s, 3H); from 3.45 to 3.57 (m, 2H); 3.67 (d, J=7.5 Hz, 1H); 3.92 (m, 1H); from 4.23 to 4.34 (m, 2H); 4.42 (m, 1H); 4.54 (d, J=5.0 Hz, 1H); 5.28 (dd, J=7.0 and 16.0 Hz, 1H); 5.62 (broad d, J=16.0 Hz, 1H); 7.16 (dd, J=1.5 and 8.0 Hz, 1H); 7.21 (dt, J=1.5 and 8.0 Hz, 1H); 7.45 (dt, J=1.5 and 8.0 Hz, 1H); 7.61 (dd, J=1.5 and 8.0 Hz, 1H); 8.21 (d, J=8.0 Hz, 1H); 10.15 (s, 1H).

EXAMPLE 20

N-(5-(3,5-difluorobenzyl)-4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide

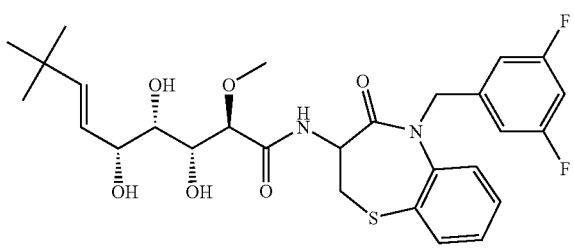

a) Step 1: Preparation of tert-butyl (5-oxoperhydro-1,4-thiazepin-6-yl)carbamate (52)

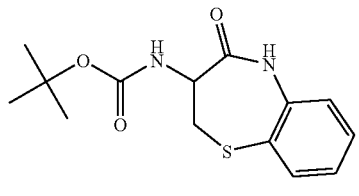

0.4 g of 50 (2.06 mmol) in 10 ml of chloroform is placed in a 50 ml three-necked flask with stirring, under an argon atmosphere. 289 µl of triethylamine (2.06 mmol) are injected in a single portion, and the mixture is placed in an ice bath. 449 mg of di-tert-butyl dicarbonate (2.06 mmol) in 10 ml of chloroform are then injected dropwise, while taking care to keep the temperature below 5° C. Stirring is continued for 3 hours, and the reaction medium is washed with 20 ml of HCl (0.5N). The organic phase is dried over magnesium sulfate, filtered and evaporated to dryness. 0.43 g of a white solid 52 is recovered (yield=71%).

b) Step 2: Preparation of tert-butyl [5-(3,5-difluoro-benzyl)-4-oxo-2,3,4,5-tetrahydro-1,5-benzothiaz-epin-3-yl]carbamate (53)

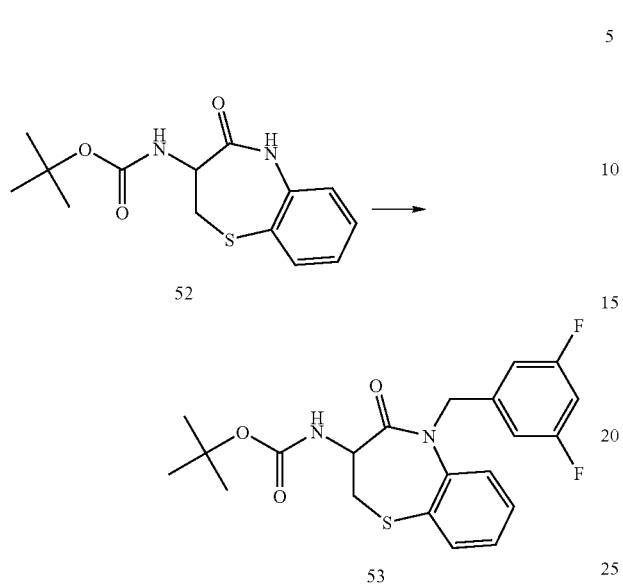

112 mg of sodium hydride as a 60% suspension in oil (2.82 mmol) are introduced at room temperature into a 50 ml round-bottomed flask, with stirring and under an argon atmosphere, containing 20 ml of DMF and 610 mg of 52 (2.07 mmol). The medium is stirred for 1 hour and 858 mg (4.14 mmol) of 3,5-difluorobenzyl bromide are then added. The medium is stirred overnight, 20 ml of EtOAc and 00 ml of water are added to the reaction medium and, after separation of the phases by settling, the organic phase is washed with 20 ml of water. The organic phase is dried, filtered and then evaporated to dryness. After chromatography on a silica cartridge (70 g) with a heptane/EtOAc mixture (gradient: 6 to 50% EtOAc), 470 mg of product 53 are recovered (yield=54%).

$^1$H NMR (400 MHz, DMSO-$d_6$), δ(ppm): 1.35 (s, 9H); 3.11 (t, J=11.5 Hz, 1H); 3.48 (dd, J=7.0 and 11.5 Hz, 1H); 4.15 (m, 1H); 5.03 (d, J=16.0 Hz, 1H); 5.13 (d, J=16.0 Hz, 1H); from 6.98 to 7.10 (m, 3H); 7.28 (broad t, J=8.0 Hz, 1H); 7.39 (broad d, J=8.0 Hz, 1H); from 7.47 to 7.53 (m, 2H); 7.63 (broad d, J=7.5 Hz, 1H).

c) Step 3: Preparation of 3-amino-5-(3,5-difluo-robenzyl)-2,3-dihydro-5H-1,5-benzothiazepin-4-one hydrochloride (54)

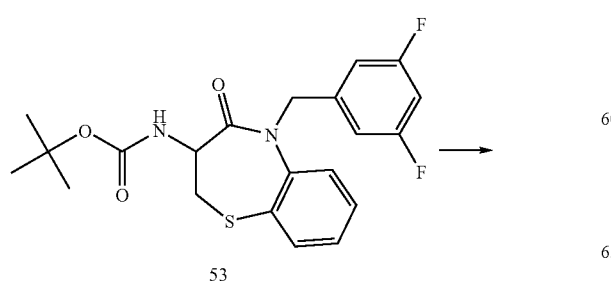

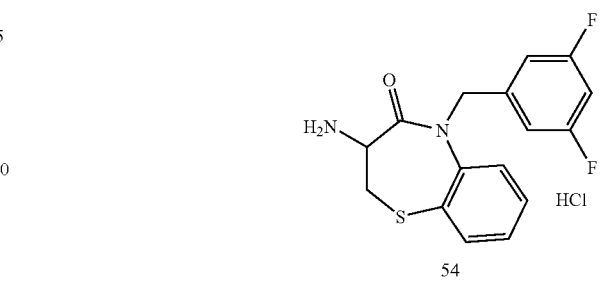

520 mg of 53 (1.24 mmol) are taken up in a 25 ml round-bottomed flask and 10 ml of a solution of hydrogen chloride in dioxane (4M) are added. The mixture is stirred for 3 hours at room temperature under argon. After evaporating off the solvent, 470 mg of amine 54 are obtained in hydrochloride form, which product is used directly in the following step.

$^1$H NMR (400 MHz, DMSO-$d_6$), δ(ppm): 3.25 (t, J=11.5 Hz, 1H); 3.75 (dd, J=7.0 and 11.5 Hz, 1H); 3.94 (dd, J=7.0 and 11.5 Hz, 1H); 5.09 (d, J=16.0 Hz, 1H); 5.24 (d, J=16.0 Hz, 1H); from 6.97 to 7.15 (m, 3H); 7.33 (m, 1H); from 7.48 to 7.59 (m, 2H); 7.68 (dd, J=1.5 and 7.5 Hz, 1H); 8.63 (broad s, 3H).

d) Step 4: Preparation of (R)—N-[5-(3,5-difluoro-benzyl)-4-oxo-2,3,4,5-tetrahydro-1,5-benzothiaz-epin-3-yl]-2-[(4R,5S,6R)-6-((E)-3,3-dimethylbut-1-enyl)-5-hydroxy-2,2-dimethyl-1,3-dioxinan-4-yl]-2-methoxy-acetamide (55)

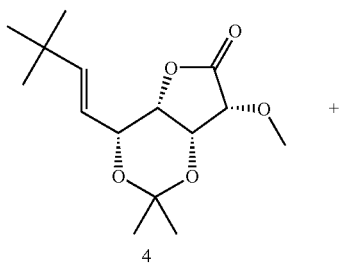

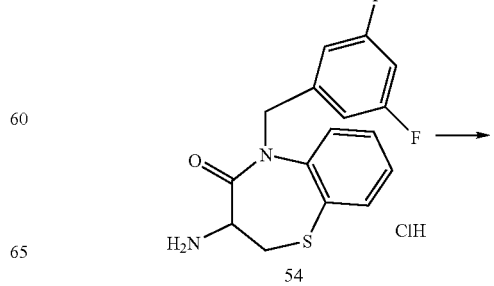

-continued

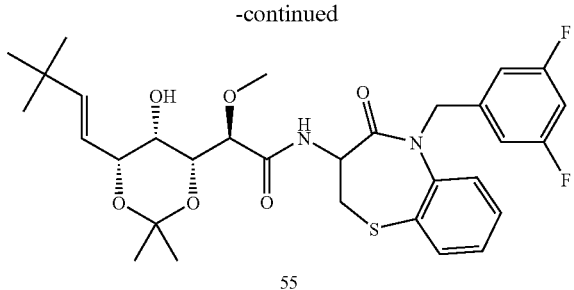

55

100 mg of 4 (352 µmol), 251 mg of 54 (0.70 mmol), 146 mg of sodium 2-ethylhexanoate (0.88 mmol) and 2.0 ml of THF are successively introduced into a Wheaton tube, with stirring and under an argon atmosphere. Stirring is continued at room temperature for 24 hours. 3 ml of ethyl acetate are added to the reaction medium. The mixture is washed successively with 3 ml of HCl solution (1N) and then with 5 ml of saturated NaHCO₃ solution and 3 ml of water. The organic phase is dried over anhydrous magnesium sulfate, filtered and then evaporated to dryness. 350 mg of an oil are obtained, which product is chromatographed on a silica cartridge (10 g, eluent: heptane/EtOAc, gradient: 12 to 100% EtOAc). 149 mg of expected product 55 are collected (yield=70%).

$^1$H NMR (300 MHz, DMSO-d$_6$), δ(ppm): 0.98 (s, 9H); 1.21 (s, 3H); 1.27 (s, 3H); from 3.13 to 3.33 (partially masked m, 2H); 3.23 (s, 3H); 3.49 (dd, J=7.0 and 11.5 Hz, 1H); 3.79 (d, J=8.5 Hz, 1H); 3.91 (broad d, J=8.5 Hz, 1H); 4.25 (broad d, J=7.0 Hz, 1H); 4.35 (d, J=7.5 Hz, 1H); 4.46 (m, 1H); 5.04 (d, J=16.5 Hz, 1H); 5.18 (d, J=16.5 Hz, 1H); 5.43 (dd, J=7.0 and 16.0 Hz, 1H); 5.68 (d, J=16.0 Hz, 1H); from 6.97 to 7.11 (m, 3H); 7.30 (m, 1H); from 7.46 to 7.57 (m, 2H); 7.65 (dd, J=1.5 and 8.0 Hz, 1H); 8.59 (d, J=8.0 Hz, 1H).

e) Step 5: Preparation of N-(5-(3,5-difluorobenzyl)-4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide (Example 20)

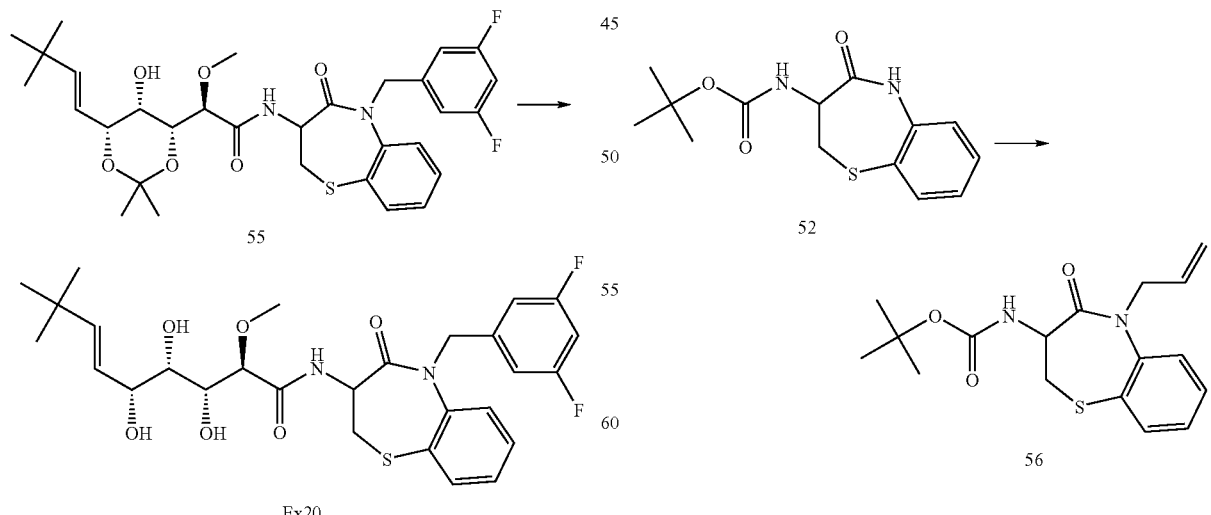

Ex20

149 mg of 55 (163 µmol) are mixed with 1.2 ml of THF and 2.4 ml of 1N hydrochloric acid, with stirring and under argon. Stirring is continued for 4 hours at room temperature. The solution is then cooled to 0° C. and neutralized to pH 7.0 with 1N sodium hydroxide. The mixture is extracted twice with 3 ml of EtOAc. The organic phases are combined, dried over magnesium sulfate, filtered and then evaporated to dryness. The crude product is then chromatographed on a silica cartridge (12 g, eluent: heptane/EtOAc, gradient: 6 to 50% EtOAc). 45 mg of expected product Example 20 are collected (yield=32%).

ES: 565(+)=(M+H)(+); 547(+)=(M+H)(+) —H₂O $^1$H NMR (400 MHz, DMSO-d$_6$), δ (ppm): 0.95 (s, 9H); 3.20 (s, 3H); 3.21 (t, J=12.0 Hz, 1H); from 3.32 to 3.47 (masked m, 1H); 3.48 (dd, J=7.0 and 12.0 Hz, 1H); 3.50 (partially masked m, 1H); 3.69 (d, J=8.0 Hz, 1H); 3.92 (m, 1H); 4.30 (broad m, 2H); 4.45 (m, 1H); 4.54 (d, J=4.5 Hz, 1H); 5.03 (d, J=16.0 Hz, 1H); 5.21 (d, J=16.0 Hz, 1H); 5.28 (dd, J=7.0 and 16.0 Hz, 1H); 5.61 (broad d, J=16.0 Hz, 1H); from 7.00 to 7.10 (m, 3H); 7.29 (m, 1H); from 7.45 to 7.55 (m, 2H); 7.61 (dd, J=1.5 and 7.5 Hz, 1H); 8.49 (d, J=8.0 Hz, 1H)

EXAMPLE 21

N-(5-allyl-4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide

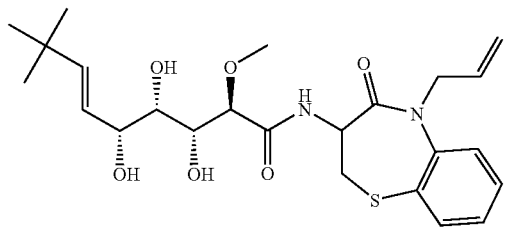

a) Step 1: Preparation of tert-butyl (5-allyl-4-oxo-2,3,4,5-tetrahydro-1,5-benzothiazepin-3-yl)-carbamate (56)

54 mg of sodium hydride as a 60% suspension (2.24 mmol) are introduced at room temperature into a 100 ml round-bottomed flask, with stirring and under an argon atmosphere, containing 25 ml of THF and 660 mg of 52 (2.24 mmol). The medium is stirred for 1 hour and 452 mg (2.24 mmol) of allyl bromide are then added. The medium is stirred overnight, 25 ml of EtOAc and 25 ml of water are added to the reaction medium and, after separation of the phases by settling, the organic phase is washed with 20 ml of water. The organic phase is dried, filtered and then evaporated to dryness. 0.7 g of crude product is recovered, which product is chromatographed on a silica cartridge (20 g) with a 75/25 heptane/EtOAc mixture. 610 mg of product 56 are recovered (yield=81%).

$^1$H NMR (400 MHz, DMSO-$d_6$), δ (ppm): 1.32 (s, 9H); 3.04 (t, J=11.5 Hz, 1H); 3.41 (dd, J=7.5 and 11.5 Hz, 1H); 4.08 (td, J=7.5 and 11.5 Hz, 1H); 4.30 (dd, J=6.0 and 16.0 Hz, 1H); 4.60 (dd, J=4.5 and 16.0 Hz, 1H); 5.04 (d, J=10.5 Hz, 1H); 5.17 (d, J=18.0 Hz, 1H); from 5.69 to 5.81 (m, 1H); from 7.25 to 7.37 (m, 2H); 7.52 (m, 2H); 7.63 (d, J=7.5 Hz, 1H).

b) Step 2: Preparation of 3-amino-5-allyl-2,3-dihydro-5H-1,5-benzothiazepin-4-one hydrochloride (57)

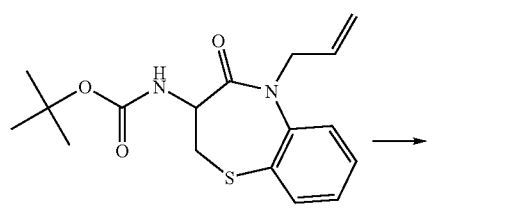

56

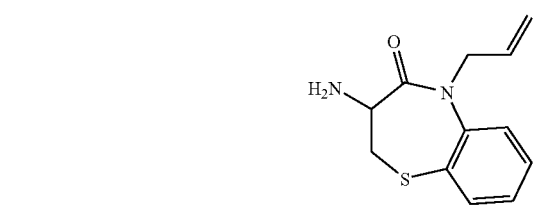

57

610 mg of 56 (1.82 mmol) are taken up in a 25 ml round-bottomed flask and 15 ml of a solution of hydrogen chloride in dioxane (4M) are added. The mixture is stirred for 3 hours at room temperature under argon. After evaporating off the solvent, a gummy residue is obtained, which is triturated from isopropyl ether to give, after filtration, 441 mg of amine 57 in hydrochloride form (cream-colored solid).

$^1$H NMR (300 MHz, DMSO-$d_6$), δ (ppm): 3.18 (t, J=11.5 Hz, 1H); 3.72 (dd, J=7.0 and 11.5 Hz, 1H); 3.83 (dd, J=7.0 and 11.5 Hz, 1H); 4.37 (tdd, J=1.5-6.5 and 16.0 Hz, 1H); 4.68 (tdd, J=1.5-5.0 and 16.0 Hz, 1H); 5.10 (qd, J=1.5 and 10.5 Hz, 1H); 5.24 (qd, J=1.5 and 17.5 Hz, 1H); 5.78 (m, 1H); from 7.30 to 7.40 (m, 1H); from 7.55 to 7.62 (m, 2H); 7.69 (broad d, J=7.5 Hz, 1H); 8.61 (broad m, 3H).

c) Step 3: Preparation of (R)—N-(5-allyl-4-oxo-2,3,4,5-tetrahydro-1,5-benzothiazepin-3-yl)-2-[(4R,5S,6R)-6-((E)-3,3-dimethylbut-1-enyl)-5-hydroxy-2,2-dimethyl-1,3-dioxinan-4-yl]-2-methoxyacetamide (58)

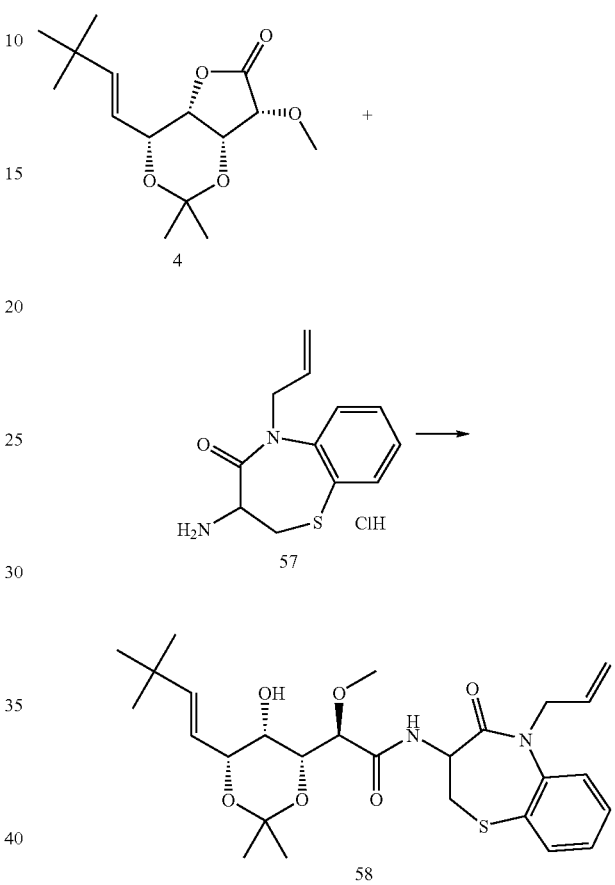

100 mg of 4 (352 μmol), 191 mg of 57 (0.70 mmol), 146 mg of sodium 2-ethylhexanoate (0.88 mmol) and 2.0 ml of THF are successively introduced into a Wheaton tube, with stirring and under an argon atmosphere. Stirring is continued at room temperature for 24 hours. 3 ml of ethyl acetate are added to the reaction medium. The mixture is washed successively with 3 ml of HCl solution (1N) and then with 5 ml of saturated NaHCO$_3$ solution and 3 ml of water. The organic phase is dried over anhydrous magnesium sulfate, filtered and then evaporated to dryness. 350 mg of an oil are obtained, which product is chromatographed on a silica cartridge (10 g, eluent: heptane/EtOAc, gradient: 12 to 100% EtOAc). 131 mg of expected product 58 are collected (yield=72%).

$^1$H NMR (300 MHz, DMSO-$d_6$), δ(ppm): 0.98 (s, 9H); 1.22 (s, 3H); 1.27 (s, 3H); 3.08 (t, J=11.5 Hz, 1H); from 3.19 to 3.33 (partially masked m, 1H); 3.22 (s, 3H); 3.43 (m, 1H); 3.78 (d, J=8.5 Hz, 1H); 3.89 (broad d, J=8.5 Hz, 1H); 4.25 (d, J=7.0 Hz, 1H); from 4.28 to 4.47 (m, 3H); from 4.53 to 4.64 (m, 1H); 5.05 (broad d, J=10.5 Hz, 1H); 5.19 (broad d, J=17.5 Hz, 1H); 5.43 (dd, J=7.5 and 16.0 Hz, 1H); 5.68 (d, J=16.0 Hz, 1H); 5.77 (m, 1H); from 7.25 to 7.35 (m, 2H); from 7.51 to 7.59 (m, 2H); 7.66 (m, 1H); 8.43 (d, J=8.0 Hz, 1H).

d) Step 4: Preparation of N-(5-allyl-4-oxo-2,3,4,5-tetrahydro-1,5-benzothiazepin-3-yl)-(E)-(2R,3R,4S,5R)-3,4,5-trihydroxy-2-methoxy-8,8-dimethylnon-6-enamide (Example 21)

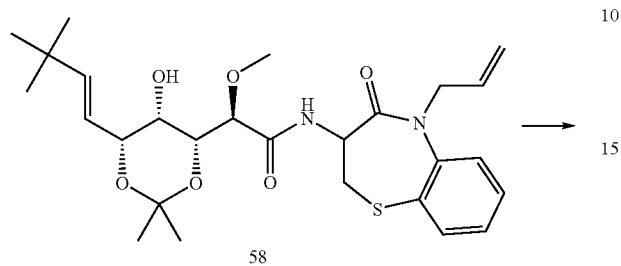

58

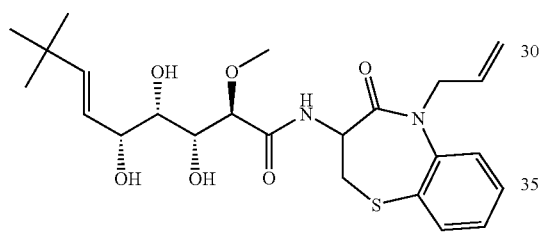

Ex21

131 mg of 58 (252 µmol) are mixed with 1.25 ml of THF and 2.5 ml of hydrochloric acid (1N), with stirring and under argon. Stirring is continued for 4 hours at room temperature. The solution is then cooled to 0° C. and neutralized to pH 7.0 with 1N sodium hydroxide. The mixture is extracted twice with 3 ml of EtOAc. The organic phases are combined, dried over magnesium sulfate and filtered, and then evaporated to dryness. The crude product is then chromatographed on a silica cartridge (12 g, eluent: heptane/EtOAc, gradient: 6 to 50% EtOAc). 44 mg of expected product Example 21 are collected (yield=44%).

ES: 479(+)=(M+H)(+); 461(+)=(M+H)(+) —H$_2$O $^1$H NMR (400 MHz, DMSO-d$_6$), δ (ppm): 0.95 (s, 9H); 3.11 (t, J=11.5 Hz, 1H); 3.19 (s, 3H); from 3.25 to 3.32 (partially masked m, 1H); from 3.40 to 3.50 (m, 2H); 3.66 (d, J=8.0 Hz, 1H); 3.91 (m, 1H); from 4.25 to 4.36 (m, 3H); 4.41 (td, J=7.0 and 11.5 Hz, 1H); 4.54 (d, J=4.5 Hz, 1H); 4.62 (broad dd, J=5.5 and 16.5 Hz, 1H); 5.04 (broad d, J=10.5 Hz, 1H); 5.19 (broad d, J=17.5 Hz, 1H); 5.27 (dd, J=7.0 and 16.0 Hz, 1H); 5.61 (broad d, J=16.0 Hz, 1H); 5.77 (m, 1H); from 7.26 to 7.34 (m, 1H); from 7.51 to 7.57 (m, 2H); 7.65 (broad d, J=7.5 Hz, 1H); 8.32 (d, J=8.0 Hz, 1H).

EXAMPLES 22a & b

N-(2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide

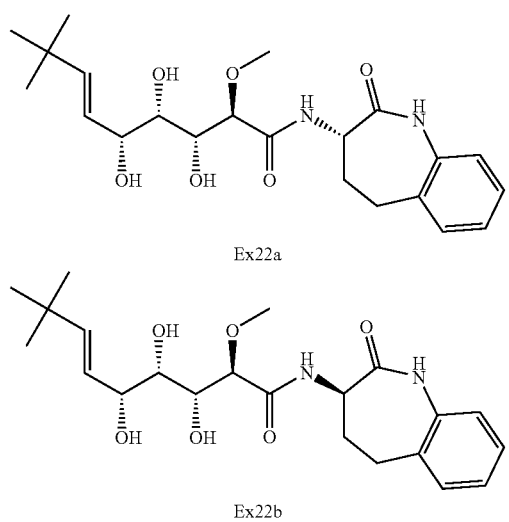

a) Step 1: Preparation of (R)-2-[(4R,5S,6R)-6-((E)-3,3-dimethylbut-1-enyl)-5-hydroxy-2,2-dimethyl-1,3-dioxinan-4-yl]-2-methoxy-N-(2-oxo-2,3,4,5-tetrahydro-1H-1-benzazepin-3-yl)acetamide (60a & b)

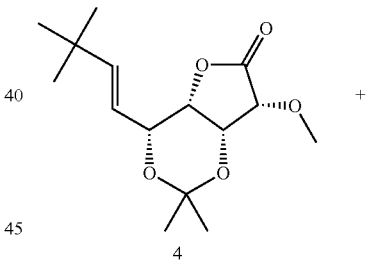

4

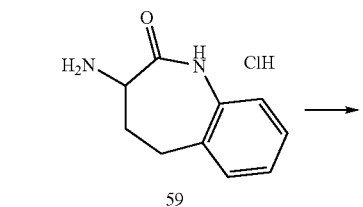

59

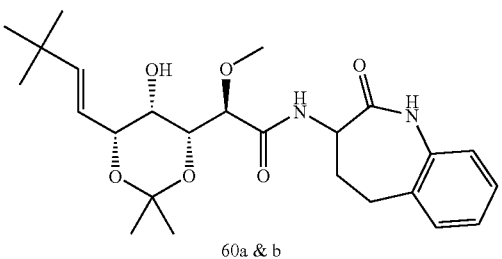

60a & b 100 mg of 4 (352 μmol), 150 mg of 59 (0.70 mmol) (sold by Interchim), 146 mg of sodium 2-ethylhexanoate (0.88 mmol) and 2.5 ml of THF are successively introduced into a Wheaton tube, with stirring and under an argon atmosphere. The mixture is stirred at room temperature for 2 days. 3 ml of ethyl acetate are added to the reaction medium. The mixture is washed with 3 ml of HCl solution (1N) and insoluble matter in gel form is formed, which matter, after filtering through a sinter funnel, gives 53 mg of expected product 60a & b (ratio 85:15) (yield=33%, white solid). The filtrate is separated by settling, the organic phase is then washed with 3 ml of saturated NaHCO₃ solution and 3 ml of water, dried over magnesium sulfate, filtered and then concentrated to dryness. After chromatography on a cartridge of NH₂-grafted silica (3 g, eluent: 50/50 heptane/EtOAc), 57 mg of 60a & b (ratio 15:85) are obtained (yield=35%)

¹H NMR (400 MHz, DMSO-d6), δ (ppm) for 60a: 0.98 (s, 9H); 1.22 (s, 3H); 1.27 (s, 3H); 2.08 (m, 1H); 2.26 (m, 1H); from 2.65 to 2.78 (m, 2H); from 3.21 to 3.33 (masked m, 1H); 3.25 (s, 3H); 3.78 (d, J=8.5 Hz, 1H); 3.90 (broad d, J=8.5 Hz, 1H); 4.20 (m, 1H); 4.26 (d, J=7.0 Hz, 1H); 4.33 (d, J=8.5 Hz, 1H); 5.44 (dd, J=7.0 and 16.0 Hz, 1H); 5.68 (d, J=16.0 Hz, 1H); 7.08 (d, J=8.0 Hz, 1H); 7.13 (broad t, J=7.5 Hz, 1H); from 7.24 to 7.32 (m, 2H); 8.12 (d, J=8.0 Hz, 1H); 9.80 (s, 1H). ¹H NMR (400 MHz, DMSO-d6), δ (ppm) for 60b: 0.99 (s, 9H); 1.24 (s, 3H); 1.29 (s, 3H); 2.06 (m, 1H); 2.26 (m, 1H); from 2.63 to 2.79 (m, 2H); from 3.22 to 3.32 (masked m, 1H); 3.23 (s, 3H); 3.73 (d, J=8.5 Hz, 1H); 3.95 (broad d, J=8.5 Hz, 1H); from 4.21 to 4.32 (m, 2H); 4.41 (d, J=8.0 Hz, 1H); 5.44 (dd, J=7.0 and 16.0 Hz, 1H); 5.68 (d, J=16.0 Hz, 1H); 7.03 (d, J=8.0 Hz, 1H); 7.14 (t, J=8.0 Hz, 1H); from 7.24 to 7.32 (m, 2H); 8.06 (d, J=8.0 Hz, 1H); 9.34 (s, 1H).

b) Step 2: Preparation of N-(2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide (Examples 22a & b)

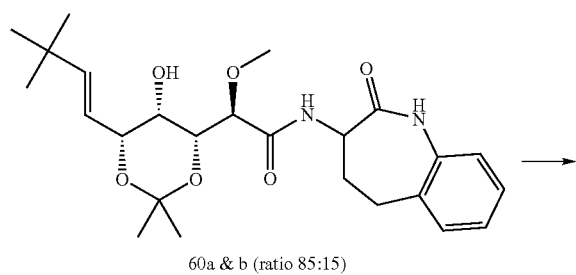

60a & b (ratio 85:15)

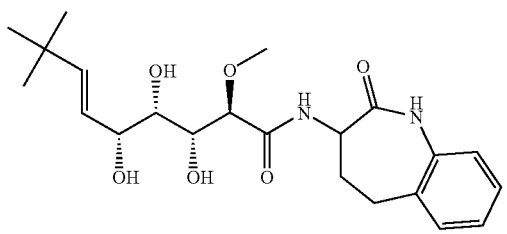

Ex22a & b (ratio 85:15)

53 mg of 60a & b (ratio 85:15) (115 μmol) are mixed with 0.6 ml of THF and 1.15 ml of 1N hydrochloric acid, with stirring and under argon. Stirring is continued for 5 hours at room temperature. The solution is then cooled to 0° C. and neutralized to pH 7.0 with 1N sodium hydroxide. The mixture is extracted twice with 5 ml of EtOAc. The organic phases are combined, dried over magnesium sulfate, filtered and then evaporated to dryness. 32.5 mg of expected product Examples 22a & b (ratio 85:15) are obtained (yield=67%).

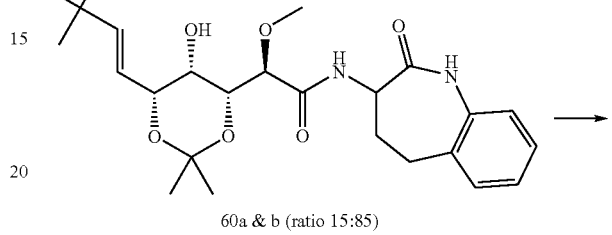

60a & b (ratio 15:85)

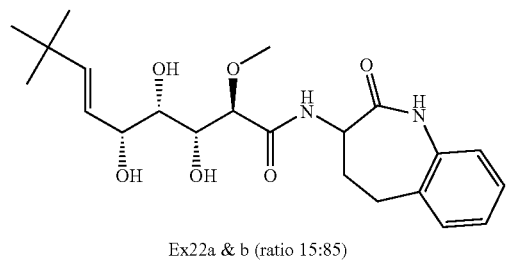

Ex22a & b (ratio 15:85)

57 mg of 60a & b (ratio 15:85) (124 μmol) are mixed with 0.65 ml of THF and 1.24 ml of 1N hydrochloric acid, with stirring and under argon. Stirring is continued for 5 hours at room temperature. The solution is then cooled to 0° C. and neutralized to pH 7.0 with 1N sodium hydroxide. The mixture is extracted twice with 5 ml of EtOAc. The organic phases are combined, dried over magnesium sulfate, filtered and then evaporated to dryness. 40.7 mg of expected product Examples 22a & b (ratio 15:85) are obtained (yield=78%).

ES: 421(+)=(M+H)(+); 403(+)=(M+H)(+) —H₂O ¹H NMR (300 MHz, DMSO-d6), δ (ppm) for Example 22a: 0.96 (s, 9H); 2.07 (m, 1H); 2.33 (m, 1H); from 2.63 to 2.80 (m, 2H); 3.23 (s, 3H); from 3.25 to 3.36 (masked m, 1H); 3.53 (m, 1H); 3.68 (d, J=7.5 Hz, 1H); 3.95 (m, 1H); from 4.17 to 4.32 (m, 2H); 4.40 (d, J=6.5 Hz, 1H); 4.53 (broad m, 1H); 5.31 (dd, J=7.0 and 16.0 Hz, 1H); 5.63 (broad d, J=16.0 Hz, 1H); 7.02 (d, J=7.5 Hz, 1H); 7.14 (t, J=7.5 Hz, 1H); from 7.23 to 7.32 (m, 2H); 8.97 (d, J=8.0 Hz, 1H); 9.89 (s, 1H). ¹H NMR (300 MHz, DMSO-d6), δ (ppm) for Example 22b: 0.96 (s, 9H); 2.07 (m, 1H); 2.32 (m, 1H); from 2.65 to 2.80 (m, 2H); 3.23 (s, 3H); from 3.24 to 3.36 (masked m, 1H); 3.53 (m, 1H); 3.67 (d, J=7.5 Hz, 1H); 3.93 (m, 1H); from 4.13 to 4.42 (m, 3H); 4.52 (broad m, 1H); 5.29 (dd, J=6.5 and 15.5 Hz, 1H); 5.62 (d, J=15.5 Hz, 1H); 7.02 (d, J=8.0 Hz, 1H); 7.13 (t, J=8.0 Hz, 1H); from 7.22 to 7.32 (m, 2H); 7.98 (d, J=7.5 Hz, 1H); 9.84 (s, 1H)

EXAMPLE 23

N-(1-dec-9-enyl-2-oxoperhydroazepin-3-yl)-(E)-(2R,3R,4S,5R)-3,4,5-trihydroxy-2-methoxy-8,8-dimethyl-non-6-enamide

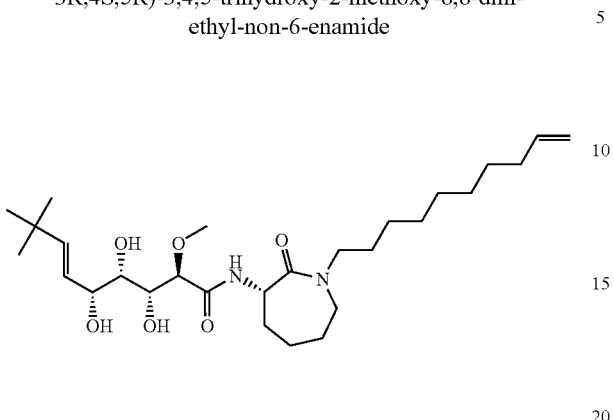

a) Step 1: Preparation of tert-butyl(S)-(1 Dec. 9-enyl-2-oxoperhydroazepin-3-yl)carbamate (62)

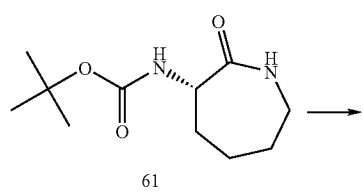

61

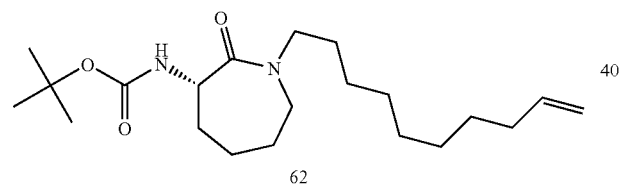

62

41.2 mg (1.2 mmol) of NaH as a suspension in oil are placed in 3 ml of DMF. 228.3 mg (1 mmol) of compound 61 (sold by Senn Chemical AG) dissolved in 2 ml of DMF are added to this solution. 1.05 g of 10 bromo-1-decene (4.8 mmol) are then added dropwise. The mixture is stirred at room temperature for 5 hours and then poured onto ice. The aqueous phase is extracted three times with EtOAc and the organic phases are washed with water and with saturated aqueous NaCl solution. The organic phases are dried over $Na_2SO_4$, filtered and evaporated to dryness. 1.6 g of crude product are obtained, which product is purified by chromatography on a silica column, eluting with an 80/20 heptane/EtOAc mixture. 1.31 g of product 62 are recovered in the form of a colorless oil (yield=80%).

ES: $(M+H)^+=367$ $^1H$ NMR (400 MHz, $CDCl_3$), δ (ppm): 6.42 (d, 1H); 5.70 (m, 1H); 4.97 (m, 2H); 4.22 (m, 1H); 3.50 to 3.20 (m, 4H); 2.00 (q, 2H); 1.85 to 1.15 (m, 18H), 1.38 (s, 9H)

b) Step 2: Preparation of (S)-3-amino-1-dec-9-enyl-perhydroazepin-2-one hydrochloride (63)

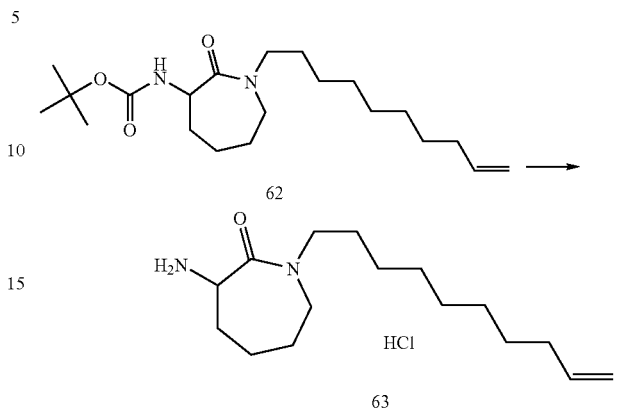

1.3 g of 62 (3.55 mmol) are taken up in a 250 ml round-bottomed flask and 90 ml of a solution of hydrogen chloride in dioxane (4M) are added. The mixture is stirred for 3 hours at room temperature under argon. After evaporating off the solvent, 1.23 g of amine 63 are obtained in hydrochloride form, which product is used directly in the following step.

ES: $(M+H)^+=303$ $^1H$ NMR (400 MHz, DMSO d6), δ (ppm: 8.13 (broad s, 1H); 5.80 (m, 1H); 4.95 (m, 2H); 4.22 (m, 1H); 3.70 to 3.25 (m, 4H); 2.00 (q, 2H); 1.90 to 1.20 (m, 18H)

c) Step 3: Preparation of (R)—N-(1-dec-9-enyl-2-oxoperhydroazepin-3-yl)-2-[(4R,5S,6R)-6-((E)-3,3-dimethyl-but-1-enyl)-5-hydroxy-2,2-dimethyl-1,3-dioxinan-4-yl]-2-methoxyacetamide (64)

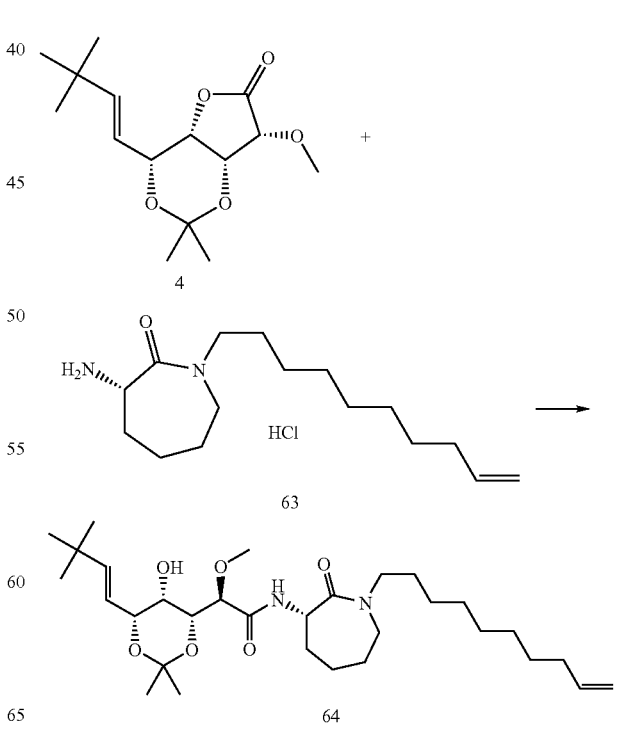

85 mg of 4 (300 µmol), 136 mg of 63 (445 µmol), 149 mg of sodium 2-ethylhexanoate (0.90 mmol) and 1.5 ml of THF are successively introduced into a Wheaton tube, with stirring and under an argon atmosphere. Stirring is continued at room temperature for 48 hours. 20 ml of ethyl acetate are added to the reaction medium. The mixture is washed successively with 20 ml of HCl solution (1N) and 20 ml of saturated aqueous NaCl. The organic phase is dried over anhydrous magnesium sulfate, filtered and then evaporated to dryness. 270 mg of an oil are obtained, which product is chromatographed on a silica cartridge (8 g, eluent: 98/2 $CH_2Cl_2$/MeOH). 140 mg of expected product 63 are collected (yield=85%; Rf: 0.2).

ES: $(M+H)^+=551^+$ d) Step 4: Preparation of N-(1-dec-9-enyl-2-oxoperhydroazepin-3-yl)-(E)-(2R,3R,4S,5R)-3,4,5-trihydroxy-2-methoxy-8,8-dimethylnon-6-enamide (Example 23)

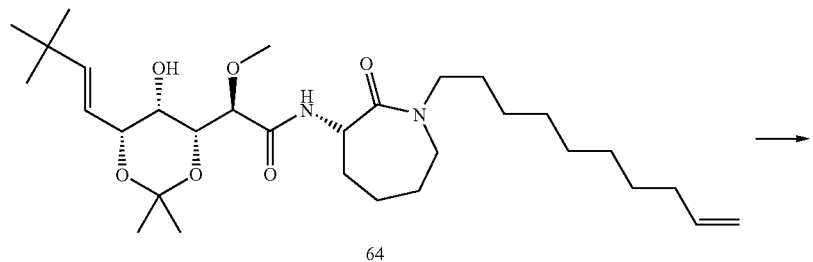

64

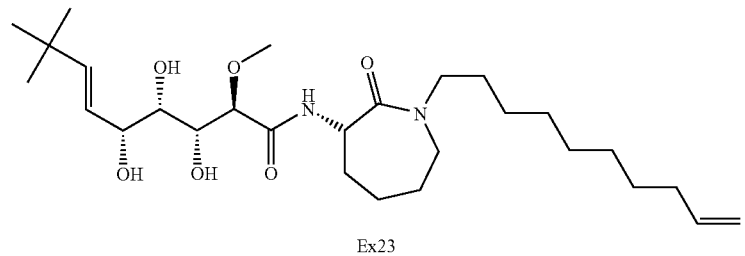

Ex23

140 mg of 64 (254 µmol) are mixed with 2.8 ml of THF and 2.8 ml of 1N hydrochloric acid, with stirring and under argon. Stirring is continued for 4 hours at room temperature. The solution is then cooled to 0° C. and neutralized to pH 7.0 with 1N sodium hydroxide. The mixture is extracted twice with 3 ml of EtOAc. The organic phases are combined, dried over magnesium sulfate, filtered and then evaporated to dryness to give 101 mg of crude product, which product is then chromatographed on a silica cartridge (12 g, eluent: 97/3 $CH_2Cl_2$/isopropanol). 69 mg of expected product Example 23 are collected (yield=53%, Rf: 0.15).

IC: 511(+)=(M+H)(+) $^1$H NMR (400 MHz, DMSO-d6), ppm (δ): 0.97 (s, 9H); from 1.17 to 1.39 (m, 12H); 1.44 (m, 2H); from 1.60 to 1.91 (m, 4H); 2.00 (m, 2H); from 3.20 to 3.36 (partially masked m, 4H); 3.26 (s, 3H); from 3.50 to 3.60 (m, 2H); 3.70 (d, J=7.0 Hz, 1H); 3.97 (m, 1H); 4.38 (broad m, 1H); from 4.46 to 4.54 (m, 2H); 4.57 (d, J=4.5 Hz, 1H); 4.93 (broad d, J=11.0 Hz, 1H); 4.99 (broad d, J=17.5 Hz, 1H); 5.33 (dd, J=6.5 and 16.0 Hz, 1H); 5.64 (d, J=16.0 Hz, 1H); 5.79 (m, 1H); 7.85 (d, J=6.5 Hz, 1H). IR ($CCl_4$): 3374; 2931; 2858; 1643; 1513; 1486; 1433; 1114; 974 & 912 cm$^{-1}$ Antiproliferative Activity of the Prepared Products The antitumoral activity of products 1 to 10 was determined by measuring the inhibition of cell proliferation of Hep-G2 cells. The cells are subcultured in a cell culture medium at a concentration of 1000 cells per well, and incubated for 4 hours at 37° C. and 5% $CO_2$.

Medium used for the Hep-G2 and HCT-116 cell culture: Dubelcco's modified Eagle's medium/Ham mixture F12 (Gibco); NEAA (10%; nonessential amino acids, Gibco); sodium pyruvate (1%, Gibco); L-glutamine (1%, Gibco); fetal calf serum (5%; PAA).

After 4 hours, the test products dissolved in a DMSO/cell culture medium mixture are added at various concentrations and the resulting mixtures are incubated for 72 hours at 37° C.

and 5% $CO_2$. The intracellular ATP content was measured using the CellTiterGlo test reagent (Promega).

The results of the cell proliferation tests are given in table 1 below:

TABLE 1

| Example | Structure | IC 50 (µM)/HEP G2 |
|---|---|---|
| Bengamide E | 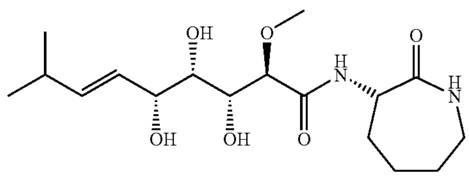 | 7.0 |
| Ex 1 | 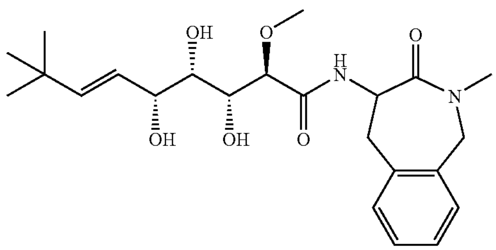 | 0.17 |
| Ex 2 | 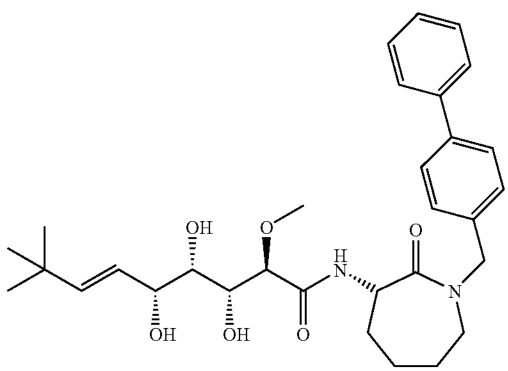 | 1.3 |
| Ex 3 | 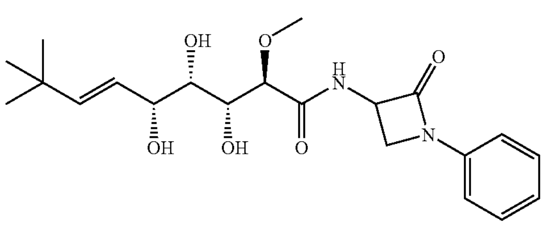 | 0.48 |
| Ex 4 | 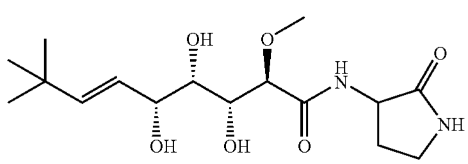 | 3.10 |
| Ex 5 | 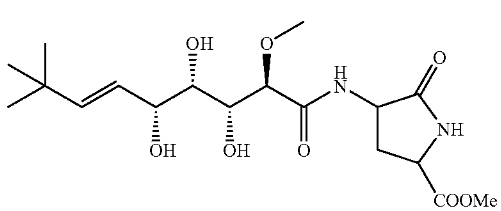 | 26.70 |

TABLE 1-continued

| Example | Structure | IC 50 (µM)/HEP G2 |
|---|---|---|
| Ex 6 | 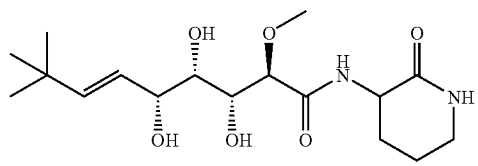 | 1.19 |
| Ex 7 | 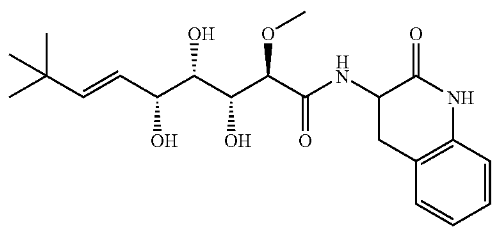 | 1.11 |
| Ex 8 | 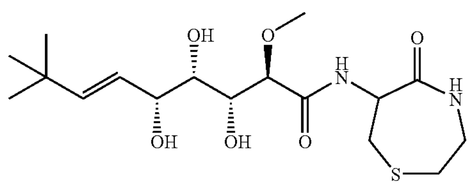 | 0.83 |
| Ex 9 | 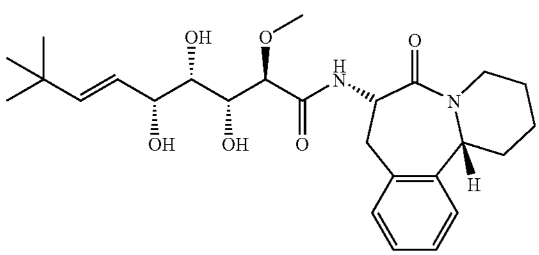 | 3.6 |
| Ex 10 | 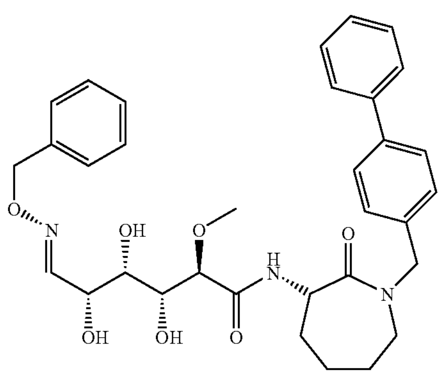 | 18.3 |

The antiproliferative activity of the products of the examples of table 2 was determined by measuring the inhibition of cellular proliferation of HCT116 cells. The cells are seeded in a cell culture medium at a concentration of 10 000 cells per well, in 0.17 ml of medium, and 20 µl of test product, at various concentrations, and 10 µl of thymidine [methyl-14C] (100 µCi/ml—specific activity 47.90 mCi/mmol; NEN Technologies reference NEC568 batch 3550-001) are added, and the cells are then incubated at 37° C. and 5% $CO_2$.

Medium used for culturing the HCT 116 cells: DMEM medium, 2 mM L-glutamine, 200 IU/ml penicillin, 200 µg/ml streptomycin and 10% (V/V) fetal calf serum (Life Technologies).

After 48 hours, the incorporation of $^{14}C$-thymidine is counted in a 1450 Microbeta Wallac Trilux liquid scintillation counter. The results R are expressed in cpm (counts per minute) and converted to a percentage of growth inhibition GI % by first subtracting from the mean of the number of cpm of the wells without B cells and then dividing by the number of cpm of the wells of the untreated cells C comprising 20 μl of product dilution medium containing 1% ethanol. (GI %=(R−B)×100/C %).

The IC50 values are calculated using equation 205 of the XLFit software (IDBS Company, UK) by nonlinear regression analysis using the Marquardt algorithm (Donald W. Marquardt, J. Soc. Industry appl. vol. 11, No. 2, June, 1963).

The products of table 2 have an IC50 on the HCT116 cells generally of less than 30 μM and preferably less than 100 nM.

TABLE 2

| Example | Structure |
|---------|-----------|
| Ex11 | 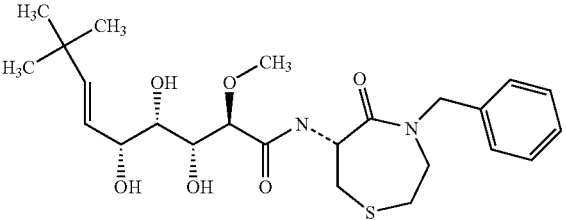 |
| Ex12 | 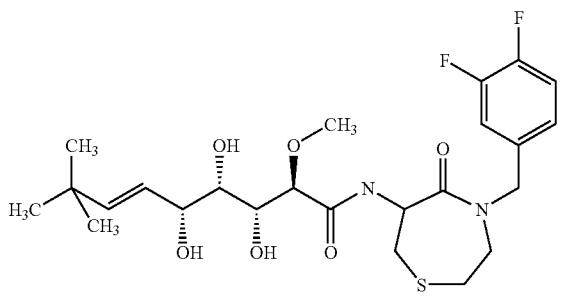 |
| Ex13 | 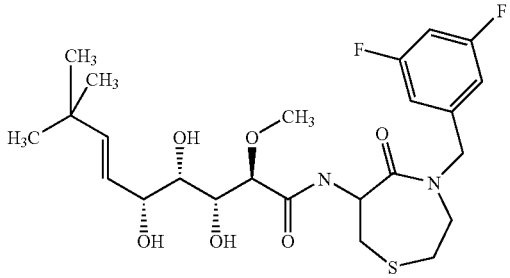 |
| Ex14 | 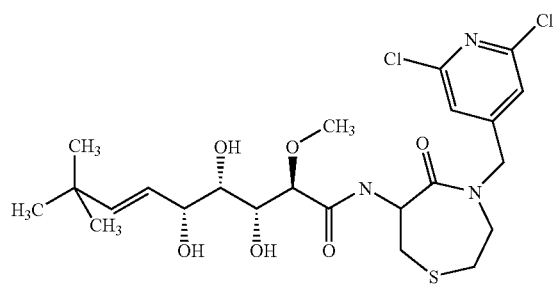 |
| Ex15 | 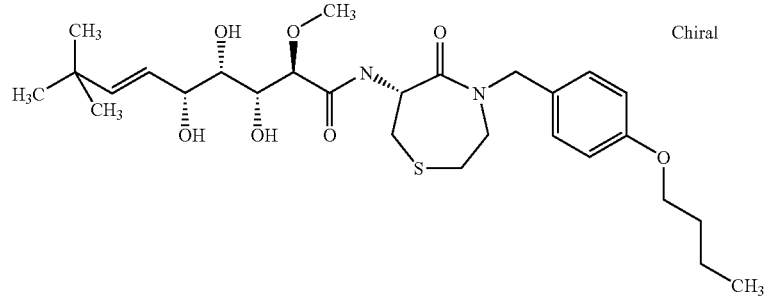 |

TABLE 2-continued

| Example | Structure |
|---|---|
| Ex16 | 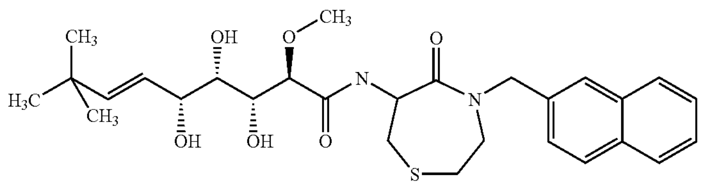 |
| Ex17 | 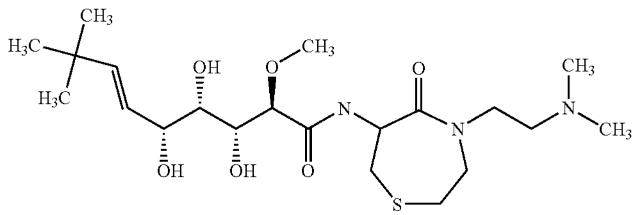 |
| Ex18 | 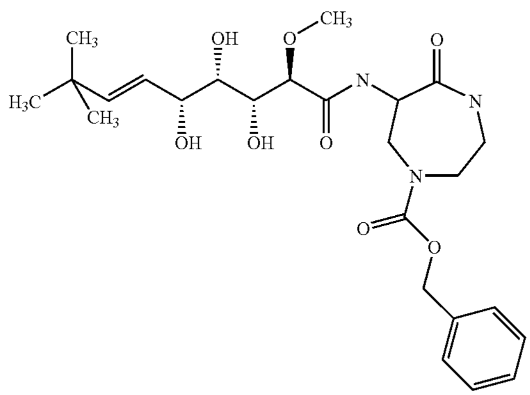 |
| Ex19 | 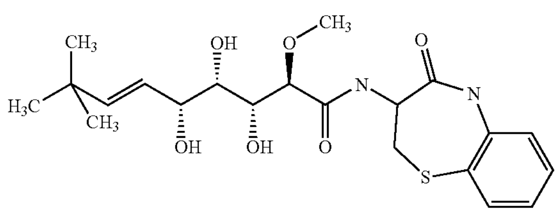 |
| Ex20 | 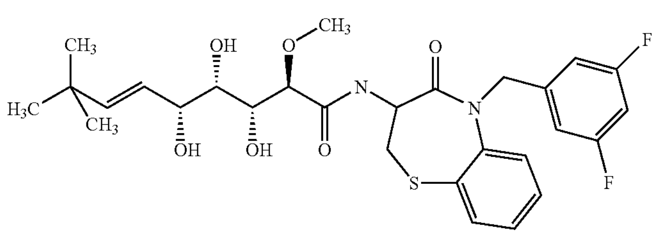 |
| Ex21 | 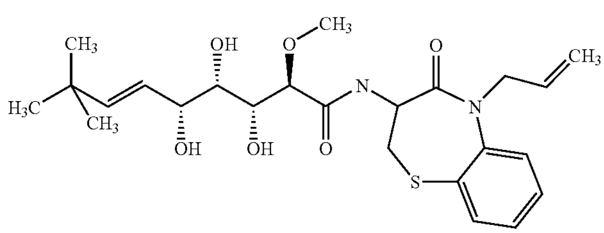 |

TABLE 2-continued

| Example | Structure |
|---|---|
| Ex22a | 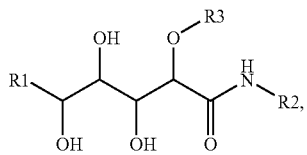 |
| Ex22b | 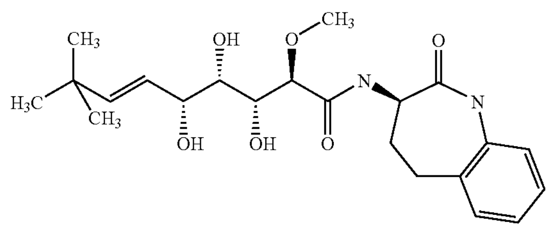 |
| Ex23 | 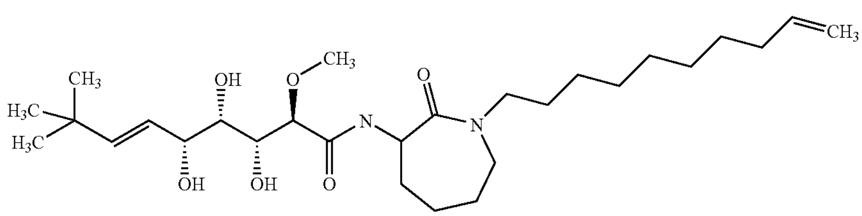 |

The invention claimed is:
1. A compound of formula (I)

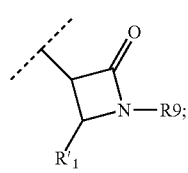

wherein:
(i) R1 is —CH═C(R11)(R12) where R11 and R12 are independently H or tert-butyl;
(ii) R2 is independently selected from the group consisting of:

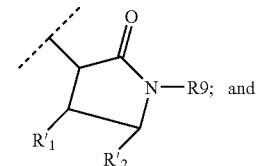

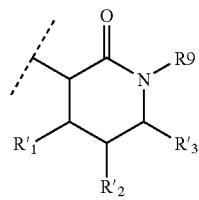

where R9 is selected from the group consisting of H and R10, where R10 is aryl, and R'$_1$, R'$_2$ and R'$_3$ are independently selected from the list consisting of H and COOalkyl, or R'$_2$ and R'$_3$ together form a phenyl ring; where aryl is a monocyclic or polycyclic aromatic substituent containing from 6 to 14 carbon atoms; and
(iii) R3 is methyl.

2. A compound of formula (I)

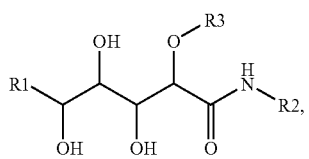

wherein:
(i) R1 is —CH═C(R11)(R12) where R11 and R12 are independently H or tert-butyl;
(ii) R2 is

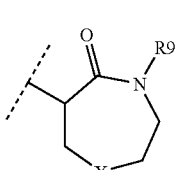 or 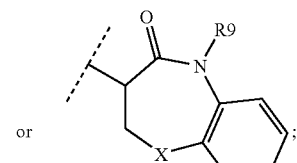

where R9 is selected from the group consisting of H and R10;

X is selected from the group consisting of $CH_2$, S, and N(Ry) where Ry is $COOR10$;

each R10 is independently selected from the group consisting of a nonbonding electron pair, H, -alkyl, -alkenyl, -alkylaryl and -alkylheteroaryl, in which each R10 is optionally substituted with at least one substituent selected from the group consisting of halogen, —O—(C1-C4)alkyl, -aryl and —$N(CH_3)_2$; where aryl is a monocyclic or polycyclic aromatic substituent containing from 6 to 14 carbon atoms; and where heteroaryl is a monocyclic or polycyclic heteroaromatic subsituent containing from 1 to 13 carbon atoms and from 1 to 14 heteroatoms selected from N, O, S and Se; and (iii) R3 is $CH_3$;

with the proviso that 1) when R2 is

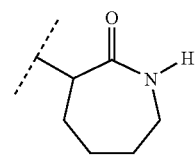

then R1 is not 3,3-dimethylbutenyl; and 2) when R2 is

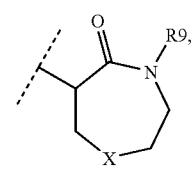

X is —$CH_2$— and R1 is —CH=CH—$C(CH_3)_3$, then R9 is not —(C1-C14)alkyl, —($CH_2$)-phenyl or —($CH_2$)-pyridine.

3. A compound of formula (I)

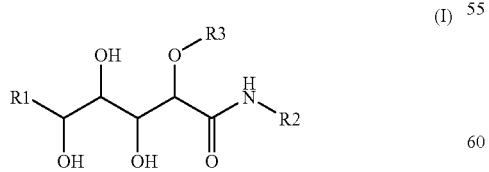

(I)

wherein:

R1 is —CH=C(R11)(R12) where R11 and R12 are independently H or tert-butyl;

R2 is a group of formula (III)

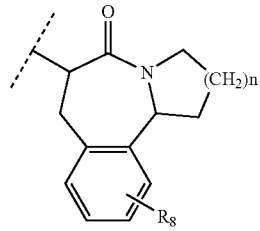

(III)

where n is 2; and $R_8$ is H.

4. A compound according to claim 2 wherein R2 is

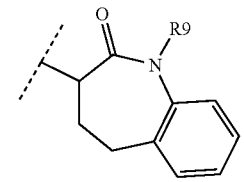 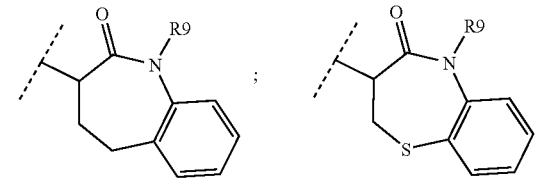

; or

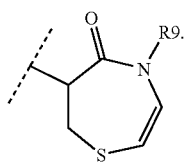

5. A compound according to claim 4 wherein R2 is

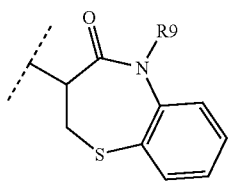 or 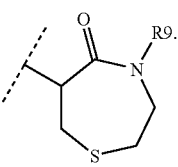

6. A compound of formula (I)

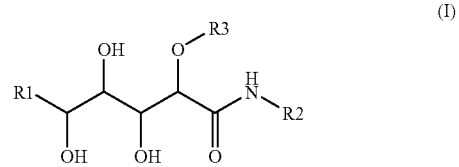

(I)

wherein:
R1 is —CH=C(R11)(R12) where R11 and R12 are independently H or tert-butyl;
R2 is

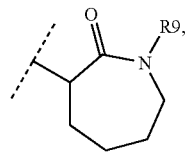

where R9 is alkenyl or phenyl substituted with 4 or 5 substituents independently chosen from halogen; and
R3 is methyl.

7. A compound of formula (I)

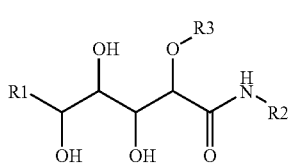

(I)

wherein:
R1 is —CH=C(R11)(R12) where R11 and R12 are independently H or tert-butyl;
R2 is

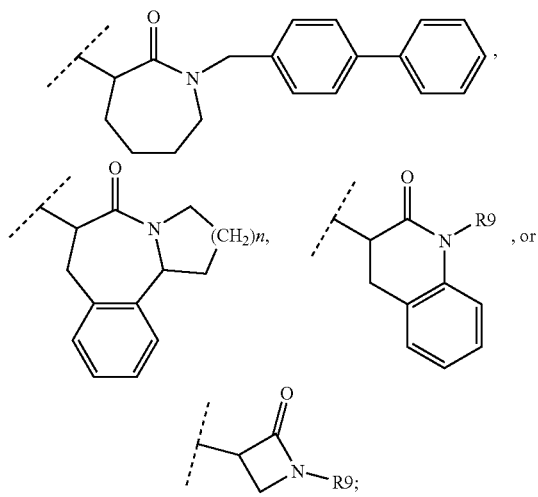

R3 is CH₃;
n is 2;
R9 is H or R10; and
R10 is independently selected from the group consisting of a nonbonding electron pair, H, (C1-C4)-alkyl, (C2-C10)-alkenyl, -aryl, -alkylaryl, and -alkylheteroaryl, where each R10 is optionally substituted with at least one substituent selected from the group consisting of halogen, —O—(C1-C4)alkyl, -aryl and —N(CH₃)₂;

where aryl is a monocyclic or polycyclic aromatic substituent containing from 6 to 14 carbon atoms; and where heteroaryl is a monocyclic or polycyclic heteroaromatic subsituent containing from 1 to 13 carbon atoms and from 1 to 4 heteroatoms selected from N, O, S and Se.

8. A compound which is:

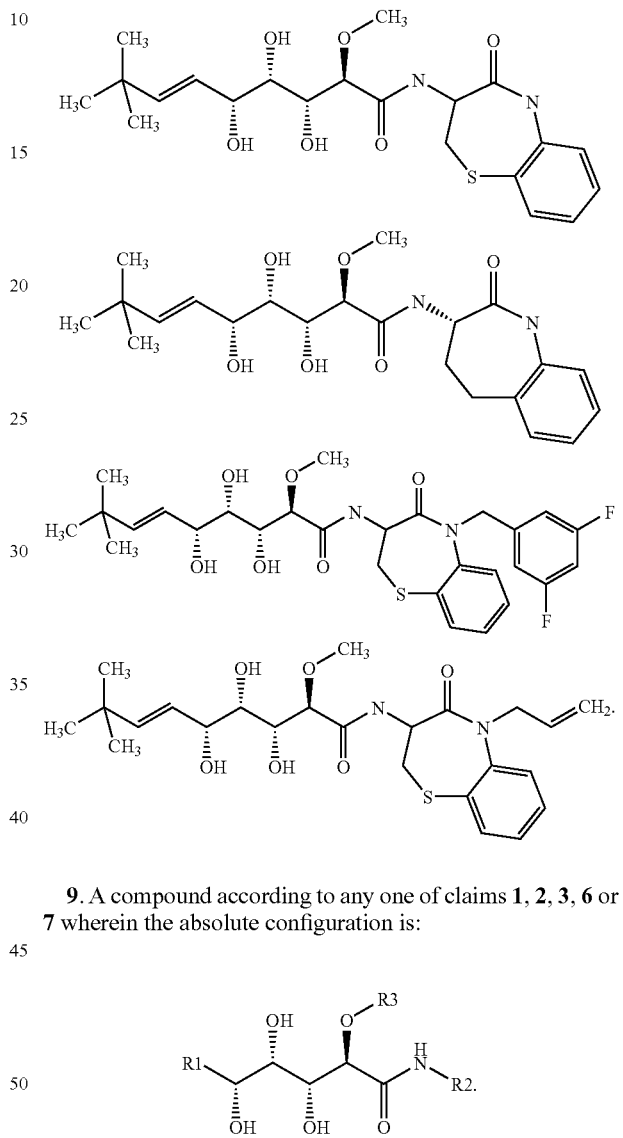

9. A compound according to any one of claims 1, 2, 3, 6 or 7 wherein the absolute configuration is:

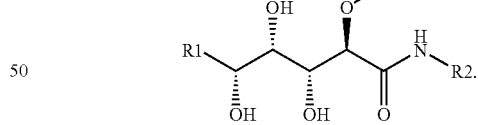

10. A pharmaceutical composition comprising a compound according to any one of claims 1, 2, 3, 6, 7 or 8 and a pharmaceutically acceptable excipient.

11. A method of treating hepatocellular carcinoma or carcinoma of the colon, in a patient in need thereof, a therapeutically effective dose of a compound according to any one of claim 1, 2, 3, 6, 7 or 8.

* * * * *